(12) United States Patent
Sharma et al.

(10) Patent No.: US 12,023,447 B2
(45) Date of Patent: Jul. 2, 2024

(54) HUMIDIFICATION PLATFORM FOR USE WITH A PORTABLE CPAP DEVICE

(71) Applicant: RESMED PTY LTD, Bella Vista (AU)

(72) Inventors: Skye Kimberley Sharma, Sydney (AU); Sung Hoon Mun, Sydney (AU); Ting Lee Teh, Sydney (AU); Samuel Thomas Horler, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 0 days.

(21) Appl. No.: 18/025,102

(22) PCT Filed: Sep. 8, 2021

(86) PCT No.: PCT/AU2021/051037
§ 371 (c)(1),
(2) Date: Mar. 7, 2023

(87) PCT Pub. No.: WO2022/051802
PCT Pub. Date: Mar. 17, 2022

(65) Prior Publication Data
US 2023/0241343 A1 Aug. 3, 2023

Related U.S. Application Data

(60) Provisional application No. 63/075,375, filed on Sep. 8, 2020.

(51) Int. Cl.
*A61M 16/16* (2006.01)
*A61M 16/06* (2006.01)
(Continued)

(52) U.S. Cl.
CPC ........ *A61M 16/16* (2013.01); *A61M 16/0616* (2014.02); *A61M 16/0633* (2014.02);
(Continued)

(58) Field of Classification Search
CPC .. A47J 27/004; A47J 27/2105; A47J 31/4439; A47L 11/30; A47L 11/34;
(Continued)

(56) References Cited

U.S. PATENT DOCUMENTS

| 4,782,832 A | 11/1988 | Trimble et al. |
| 4,944,310 A | 7/1990 | Sullivan |

(Continued)

FOREIGN PATENT DOCUMENTS

| EP | 3 539 601 A1 | 9/2019 |
| FR | 3 008 621 A1 | 1/2015 |

(Continued)

OTHER PUBLICATIONS

"*Respiratory Physiology*", by John B. West, Lippincott Williams & Wilkins, 9th edition published 2012 (8 pages).

(Continued)

*Primary Examiner* — Annette Dixon
(74) *Attorney, Agent, or Firm* — Nixon & Vanderhye P.C.

(57) ABSTRACT

A humidifier for humidifying a flow of pressurized breathable gas to be delivered to a patient includes a dock and a humidification tub. The dock includes a device compartment that is configured to at least partially removably receive an RPT device that is configured to supply the flow of pressurized breathable gas. The dock also includes a humidification compartment that is fluidly connected to the device compartment. The humidification tub is configured to contain a supply of water and is at least partially removably received within the humidification compartment so that, in an operational configuration, the humidification tub is arranged to receive the flow of pressurized breathable gas and output the flow of pressurized breathable gas with (Continued)

increased humidity. The dock also includes a heater fixed to the humidification tub. The heater is configured to heat the supply of water.

33 Claims, 25 Drawing Sheets

(51) Int. Cl.
*A61M 16/08* (2006.01)
*A61M 16/10* (2006.01)
(52) U.S. Cl.
CPC ...... *A61M 16/0875* (2013.01); *A61M 16/106* (2014.02); *A61M 16/109* (2014.02)
(58) Field of Classification Search
CPC ............. A47L 11/4013; A47L 11/4016; A47L 11/4027; A47L 11/4083; A47L 11/4097; A47L 7/0028; A47L 7/0038; A47L 7/0042; A47L 9/327; A61D 7/04; A61L 2/035; A61M 15/0085; A61M 16/00; A61M 16/0003; A61M 16/0009; A61M 16/0051; A61M 16/0057; A61M 16/0066; A61M 16/0069; A61M 16/0075; A61M 16/021; A61M 16/022; A61M 16/024; A61M 16/026; A61M 16/06; A61M 16/0616; A61M 16/0666; A61M 16/0683; A61M 16/08; A61M 16/0816; A61M 16/0833; A61M 16/0858; A61M 16/0875; A61M 16/10; A61M 16/1005; A61M 16/1045; A61M 16/105; A61M 16/1055; A61M 16/1065; A61M 16/107; A61M 16/1075; A61M 16/1085; A61M 16/109; A61M 16/1095; A61M 16/125; A61M 16/14; A61M 16/142; A61M 16/16; A61M 16/161; A61M 16/162; A61M 16/164; A61M 16/165; A61M 16/167; A61M 16/207; A61M 16/208; A61M 2016/0021; A61M 2016/0027; A61M 2016/003; A61M 2016/0033; A61M 2016/0036; A61M 2016/0039; A61M 2016/0042; A61M 2039/1022; A61M 2039/1033; A61M 2205/02; A61M 2205/121; A61M 2205/123; A61M 2205/127; A61M 2205/13; A61M 2205/14; A61M 2205/15; A61M 2205/18; A61M 2205/21; A61M 2205/276; A61M 2205/3306; A61M 2205/3317; A61M 2205/332; A61M 2205/3331; A61M 2205/3334; A61M 2205/3355; A61M 2205/3365; A61M 2205/3368; A61M 2205/3372; A61M 2205/3375; A61M 2205/3379; A61M 2205/3382; A61M 2205/3386; A61M 2205/3389; A61M 2205/3553; A61M 2205/3561; A61M 2205/3584; A61M 2205/3592; A61M 2205/36; A61M 2205/3606; A61M 2205/362; A61M 2205/3653; A61M 2205/42; A61M 2205/502; A61M 2205/505; A61M 2205/581; A61M 2205/582; A61M 2205/583; A61M 2205/702; A61M 2205/8206; A61M 2205/8212; A61M 2206/11; A61M 2206/14; A61M 2206/16; A61M 2207/10; A61M 2209/06; A61M 2209/08; A61M 2209/086; A61M 2210/0618; A61M 2210/0625; A61M 2230/005; A61M 2230/63; A61M 39/1055; A62B 7/02; A62B 9/003; B01D 47/02; B01D 5/0039; B05B 17/0615; B05B 7/0012; B05B 7/0081; C02F 1/46104; C02F 2001/46185; C02F 2303/04; F04B 45/043; F04B 45/045; F21V 33/0088; F22B 1/284; F24F 2006/006; F24F 2006/008; F24F 2140/30; F24F 2221/12; F24F 3/1405; F24F 6/00; F24F 6/025; F24F 6/043; F24F 6/06; F24F 6/10; F24F 6/12; G01F 23/02; G06F 3/011; G06F 3/017; G06N 20/00; G06V 40/28; H01L 21/67248; Y02A 20/00; Y10S 261/34; Y10S 261/46; Y10S 261/48; Y10S 261/65; Y10S 261/80; Y10T 137/8342; Y10T 29/49085

See application file for complete search history.

(56) References Cited

U.S. PATENT DOCUMENTS

| | | | |
|---|---|---|---|
| 5,061,405 A * | 10/1991 | Stanek | F24F 6/043 261/104 |
| 5,483,616 A * | 1/1996 | Chiu | F24F 6/043 392/404 |
| 5,687,715 A | 11/1997 | Landis | |
| 6,532,959 B1 | 3/2003 | Berthon-Jones | |
| 6,581,594 B1 | 6/2003 | Drew et al. | |
| 7,327,949 B1 * | 2/2008 | Cheng | A61M 16/109 219/443.1 |
| 7,866,944 B2 | 1/2011 | Kenyon et al. | |
| 8,636,479 B2 | 1/2014 | Kenyon et al. | |
| 8,638,014 B2 | 1/2014 | Sears et al. | |
| 8,733,349 B2 | 5/2014 | Bath et al. | |
| 2006/0055069 A1 * | 3/2006 | DiMatteo | A61M 16/16 261/DIG. 65 |
| 2007/0169776 A1 * | 7/2007 | Kepler | A61M 16/107 128/200.14 |
| 2008/0066751 A1 * | 3/2008 | Polacsek | A61M 16/16 128/204.17 |
| 2009/0038614 A1 * | 2/2009 | Kuo | A61M 16/1075 128/203.26 |
| 2009/0044808 A1 | 2/2009 | Guney et al. | |
| 2009/0050156 A1 | 2/2009 | Ng et al. | |
| 2010/0000534 A1 | 1/2010 | Kooij et al. | |
| 2010/0147299 A1 * | 6/2010 | Row | A61M 16/109 128/203.27 |
| 2012/0298099 A1 | 11/2012 | Lalonde | |
| 2013/0206140 A1 | 8/2013 | Kepler et al. | |
| 2017/0259019 A1 | 9/2017 | Cariola et al. | |
| 2019/0298964 A1 | 10/2019 | Bayer | |
| 2020/0188616 A1 | 6/2020 | Kenyon et al. | |

FOREIGN PATENT DOCUMENTS

| | | |
|---|---|---|
| WO | WO 98/004310 A1 | 2/1998 |
| WO | WO 98/034665 A1 | 8/1998 |
| WO | WO 2000/078381 A1 | 12/2000 |
| WO | WO 2004/073778 A1 | 9/2004 |
| WO | WO 2005/063328 A1 | 7/2005 |
| WO | WO 2006/074513 A1 | 7/2006 |
| WO | WO 2006/130903 A1 | 12/2006 |
| WO | 2007/101298 A1 | 9/2007 |
| WO | WO 2009/052560 A1 | 4/2009 |
| WO | WO 2010/135785 A1 | 12/2010 |
| WO | WO 2012/171072 A1 | 12/2012 |
| WO | WO 2013/020167 A1 | 2/2013 |

(56) References Cited

FOREIGN PATENT DOCUMENTS

WO           2016/089224 A1    6/2016
WO    WO 2019/189126 A1    10/2019

OTHER PUBLICATIONS

International Search Report dated Nov. 29, 2021 issued in International Application No. PCT/AU2021/051037 (8 pages).
Written Opinion of the International Searching Authority dated Nov. 29, 2021 issued in International Application No. PCT/AU2021/051037 (5 pages).
International Preliminary Report on Patentability dated Mar. 7, 2023 issued in International Application No. PCT/AU2021/051037 (6 pages).
Extended European Search Report dated Feb. 26, 2024 issued in European Application 21865384.8 (11 pages).

\* cited by examiner

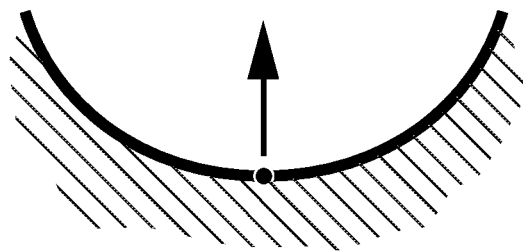
FIG. 3B — Relatively Large Positive Curvature
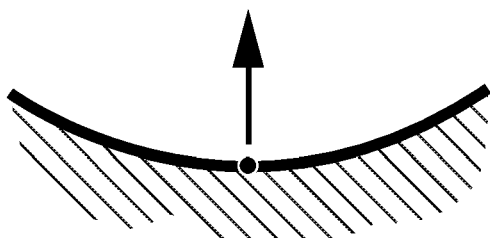
FIG. 3C — Relatively Small Positive Curvature
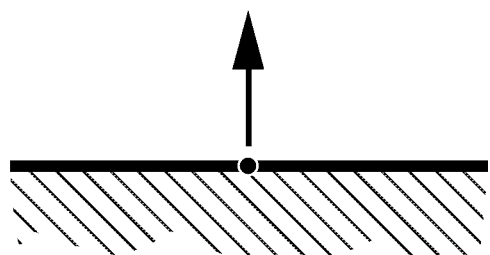
FIG. 3D — Zero Curvature
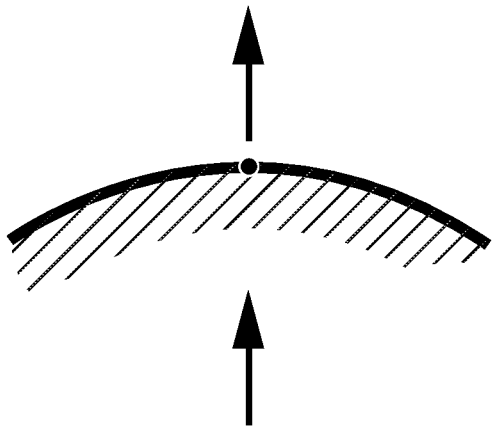
FIG. 3E — Relatively Small Negative Curvature
FIG. 3F — Relatively Large Negative Curvature

HUMIDIFICATION PLATFORM FOR USE WITH A PORTABLE CPAP DEVICE

1 CROSS-REFERENCE TO RELATED APPLICATION

This application is the U.S. national phase of International Application No. PCT/AU2021/051037 filed Sep. 8, 2021 which designated the U.S. and claims priority to U.S. Provisional Application No. 63/075,375 filed Sep. 8, 2020, the entire contents of each of which are hereby incorporated by reference.

2 BACKGROUND OF THE TECHNOLOGY

2.1 Field of the Technology

The present technology relates to one or more of the screening, diagnosis, monitoring, treatment, prevention and amelioration of respiratory-related disorders. The present technology also relates to medical devices or apparatus, and their use.

2.2 Description of the Related Art 2.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

A range of therapies have been used to treat or ameliorate such conditions. Furthermore, otherwise healthy individuals may take advantage of such therapies to prevent respiratory disorders from arising. However, these have a number of shortcomings.

2.2.2 Therapies

Various respiratory therapies, such as Continuous Positive Airway Pressure (CPAP) therapy, Non-invasive ventilation (NIV), Invasive ventilation (IV), and High Flow Therapy (HFT) have been used to treat one or more of the above respiratory disorders.

2.2.2.1 Respiratory Pressure Therapies

Respiratory pressure therapy is the application of a supply of air to an entrance to the airways at a controlled target pressure that is nominally positive with respect to atmosphere throughout the patient's breathing cycle (in contrast to negative pressure therapies such as the tank ventilator or cuirass).

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

2.2.2.2 Flow Therapies

Not all respiratory therapies aim to deliver a prescribed therapeutic pressure. Some respiratory therapies aim to deliver a prescribed respiratory volume, by delivering an inspiratory flow rate profile over a targeted duration, possibly superimposed on a positive baseline pressure. In other cases, the interface to the patient's airways is 'open' (unsealed) and the respiratory therapy may only supplement the patient's own spontaneous breathing with a flow of conditioned or enriched gas. In one example, High Flow therapy (HFT) is the provision of a continuous, heated, humidified flow of air to an entrance to the airway through an unsealed or open patient interface at a "treatment flow rate" that is held approximately constant throughout the respiratory cycle. The treatment flow rate is nominally set to exceed the patient's peak inspiratory flow rate. HFT has been used to treat OSA, CSR, respiratory failure, COPD, and other respiratory disorders. One mechanism of action is that the high flow rate of air at the airway entrance improves ventilation efficiency by flushing, or washing out, expired $CO_2$ from the patient's anatomical deadspace. Hence, HFT is thus sometimes referred to as a deadspace therapy (DST). Other benefits may include the elevated warmth and humidification (possibly of benefit in secretion management) and the potential for modest elevation of airway pressures. As an alternative to constant flow rate, the treatment flow rate may follow a profile that varies over the respiratory cycle.

Another form of flow therapy is long-term oxygen therapy (LTOT) or supplemental oxygen therapy. Doctors may prescribe a continuous flow of oxygen enriched air at a specified oxygen concentration (from 21%, the oxygen fraction in ambient air, to 100%) at a specified flow rate (e.g., 1 litre per minute (LPM), 2 LPM, 3 LPM, etc.) to be delivered to the patient's airway.

2.2.2.3 Supplementary Oxygen

For certain patients, oxygen therapy may be combined with a respiratory pressure therapy or HFT by adding supplementary oxygen to the pressurised flow of air. When oxygen is added to respiratory pressure therapy, this is referred to as RPT with supplementary oxygen. When oxygen is added to HFT, the resulting therapy is referred to as HFT with supplementary oxygen.

2.2.3 Respiratory Therapy Systems

These respiratory therapies may be provided by a respiratory therapy system or device. Such systems and devices may also be used to screen, diagnose, or monitor a condition without treating it.

A respiratory therapy system may comprise a Respiratory Pressure Therapy Device (RPT device), an air circuit, a humidifier, a patient interface, an oxygen source, and data management.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 $cmH_2O$ relative to ambient pressure. For other forms of therapy, such as the delivery of oxygen, the patient interface may not include a seal sufficient to facilitate delivery to the airways of a supply of gas at a positive pressure of about 10 $cmH_2O$. For flow therapies such as nasal HFT, the patient interface is configured to insufflate the nares but specifically to avoid a complete seal. One example of such a patient interface is a nasal cannula.

2.2.3.1.1 Seal-Forming Structure

Patient interfaces may include a seal-forming structure. Since it is in direct contact with the patient's face, the shape and configuration of the seal-forming structure can have a direct impact the effectiveness and comfort of the patient interface.

A patient interface may be partly characterised according to the design intent of where the seal-forming structure is to engage with the face in use. In one form of patient interface, a seal-forming structure may comprise a first sub-portion to form a seal around the left naris and a second sub-portion to form a seal around the right naris. In one form of patient interface, a seal-forming structure may comprise a single element that surrounds both nares in use. Such single element may be designed to for example overlay an upper lip region and a nasal bridge region of a face. In one form of patient interface a seal-forming structure may comprise an element that surrounds a mouth region in use, e.g. by forming a seal on a lower lip region of a face. In one form of patient interface, a seal-forming structure may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming structure that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

2.2.3.1.2 Positioning and Stabilising

A seal-forming structure of a patient interface used for positive air pressure therapy is subject to the corresponding force of the air pressure to disrupt a seal. Thus a variety of techniques have been used to position the seal-forming structure, and to maintain it in sealing relation with the appropriate portion of the face.

2.2.3.2 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressure-controlled (for respiratory pressure therapies) or flow-controlled (for flow therapies such as HFT). Thus RPT devices may also act as flow therapy devices. Examples of RPT devices include a CPAP device and a ventilator.

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO 3744 in CPAP mode at 10 $cmH_2O$).

| RPT Device name | A-weighted sound pressure level dB(A) | Year (approx.) |
| --- | --- | --- |
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ Humidifier | 31.1 | 2005 |
| S9 AutoSet ™ | 26.5 | 2010 |
| S9 AutoSet ™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

2.2.3.3 Air Circuit

An air circuit is a conduit or a tube constructed and arranged to allow, in use, a flow of air to travel between two components of a respiratory therapy system such as the RPT device and the patient interface. In some cases, there may be separate limbs of the air circuit for inhalation and exhalation. In other cases, a single limb air circuit is used for both inhalation and exhalation.

2.2.3.4 Humidifier

Delivery of a flow of air without humidification may cause drying of airways. The use of a humidifier with an RPT device and the patient interface produces humidified gas that minimizes drying of the nasal mucosa and increases patient airway comfort. In addition, in cooler climates, warm air applied generally to the face area in and about the patient interface is more comfortable than cold air.

A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small. A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore, medical humidifiers may have more stringent safety constraints than industrial humidifiers While a number of medical humidifiers are known, they can suffer from one or more shortcomings. Some medical humidifiers may provide inadequate humidification, some are difficult or inconvenient to use by patients.

2.2.3.5 Data Management

There may be clinical reasons to obtain data to determine whether the patient prescribed with respiratory therapy has been "compliant", e.g. that the patient has used their RPT device according to one or more "compliance rules". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

2.2.3.6 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

2.2.4 Screening, Diagnosis, and Monitoring Systems

Polysomnography (PSG) is a conventional system for diagnosis and monitoring of cardio-pulmonary disorders, and typically involves expert clinical staff to apply the system. PSG typically involves the placement of 15 to 20 contact sensors on a patient in order to record various bodily signals such as electroencephalography (EEG), electrocardiography (ECG), electrooculograpy (EOG), electromyography (EMG), etc. PSG for sleep disordered breathing has involved two nights of observation of a patient in a clinic, one night of pure diagnosis and a second night of titration of treatment parameters by a clinician. PSG is therefore expensive and inconvenient. In particular it is unsuitable for home screening/diagnosis/monitoring of sleep disordered breathing.

Screening and diagnosis generally describe the identification of a condition from its signs and symptoms. Screening typically gives a true/false result indicating whether or not a patient's SDB is severe enough to warrant further investigation, while diagnosis may result in clinically actionable information. Screening and diagnosis tend to be one-off processes, whereas monitoring the progress of a condition can continue indefinitely. Some screening/diagnosis systems are suitable only for screening/diagnosis, whereas some may also be used for monitoring.

Clinical experts may be able to screen, diagnose, or monitor patients adequately based on visual observation of PSG signals. However, there are circumstances where a clinical expert may not be available, or a clinical expert may not be affordable. Different clinical experts may disagree on a patient's condition. In addition, a given clinical expert may apply a different standard at different times.

3 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

One form of the present technology comprises a humidifier for humidifying a flow of pressurized breathable gas to be delivered to a patient.

One form of the present technology comprises a humidifier comprising a chamber, and a tub being removably positionable within the chamber.

One form of the present technology comprises a chamber configured to removably support a humidifier tub and/or and RPT device.

One form of the present technology comprises a humidifier comprising a tub including a heating element for heating an internal cavity of the tub.

One form of the present technology comprises a humidifier including a reservoir configured to be inserted and/or removed from a dock with a single hand.

One form of the present technology comprises a humidifier dock with a device compartment for removably receiving a RPT device and a humidification compartment for removably receiving a reservoir.

Another aspect of one form of the present technology is the RPT device is configured to be at least partially exposed when fully inserted into the device compartment, and the reservoir is configured to be at least partially exposed when fully inserted into the humidification compartment.

Another aspect of one form of the present technology is the reservoir includes a lid configured to be exposed when the reservoir is fully inserted into the humidification compartment. A patient capable of refilling the reservoir while the reservoir is fully inserted into the humidification compartment.

Another form of the present technology comprises a humidifier for humidifying a flow of pressurized breathable gas to be delivered to a patient, the humidifier comprising:
  a dock; and
  a tub configured to contain a supply of water, the tub being removably coupled to the dock.

Another form of the present technology comprises a humidifier for humidifying a flow of pressurized breathable gas to be delivered to a patient, the humidifier comprising:
  a tub configured to contain a supply of water, the tub configured to receive the flow of pressurized breathable gas and output the flow of pressurized breathable gas with increased humidity.

Another form of the present technology comprises a humidifier for humidifying a flow of pressurized breathable gas to be delivered to a patient, the humidifier comprising:
  a dock comprising:
    a device compartment configured to removably receive a RPT device that is configured to supply the flow of pressurized breathable gas, and
    a humidification compartment spaced apart from the device compartment and fluidly connected to the device compartment; and
  a tub configured to contain a supply of water, the tub configured to receive the flow of pressurized breathable gas and output the flow of pressurized breathable gas with increased humidity, the tub comprising:
    a tub base including a cavity configured to contain the supply of water;
    a heater fixed to the tub base and configured to heat the supply of water; and
    a tub lid removably coupled to the tub base and configured to selectively cover an opening to the cavity, wherein the tub base, the heater and the tub lid as a unit are removably positionable within the humidification compartment.

Another form of the present technology comprises a humidifier for humidifying a flow of pressurized breathable gas to be delivered to a patient, the humidifier comprising:
  a dock comprising:
    a device compartment configured to at least partially removably receive an RPT device that is configured to supply the flow of pressurized breathable gas, and
    a humidification compartment connected to the device compartment; and
  a humidification tub configured to contain a supply of water and to be at least partially removably received in the humidification compartment so that, in operational configuration, the humidification tub is arranged to receive the flow of pressurized breathable gas and output the flow of pressurized breathable gas with increased humidity
  a heater fixed to the humidification tub and configured to heat the supply of water.

In some examples: a) the humidification tub is arranged to engage and disengage with the dock along a humidification tub insertion axis in a substantially vertical direction; b) the humidification tub comprises a tub base arranged to be, at least partially, removably received in the humidification compartment; b) the tub base includes a cavity configured to contain the supply of water; c) the humidification tub comprises a tub lid removably coupled to the tub base; and/or d) the heater is attached to the tub base.

In some examples: a) the heater is overmolded to an inner side of the tub base; b) the tub base includes an electrical connector connected to the heater. The electrical connector in the tub base is configured to electrically connect with an electrical connector disposed within the humidification compartment; and/or c) the tub lid is removably coupled to the tub base and configured for single handed operation.

In some examples: a) the tub lid further comprises a water inlet opening that allows filling of the tub base with water; b) a cap is removably coupled to the tub lid in order to selectively cover the water inlet opening; c) the humidification tub is only partially received within the humidification compartment so that the humidification tub extends beyond the space defined by the humidification compartment; d) at least the tub lid is exposed to ambient and uncovered by the dock in use; and/or e) the cap is removable while the tub base is at least partially positioned within the humidification compartment.

In some examples: a) the tub lid includes a shroud configured to be received within the cavity when the tub lid is coupled to the tub base; b) the shroud is spaced apart from the water inlet opening; and/or c) the shroud is oriented with a negatively domed shape with respect to the water inlet opening.

In some examples: a) an outlet is configured to convey the flow of pressurized breathable gas to the patient, the outlet is spaced apart from the device compartment and from the humidification compartment; b) a first fluid conduit extends between the device compartment and the humidification compartment, the first fluid conduit configured to covey pressurized breathable gas from the device compartment to the humidification compartment; c) a second fluid conduit extends between the humidification compartment and the outlet, the second fluid conduit configured to covey pressurized breathable gas from the humidification compartment to the outlet; d) the humidification compartment includes a third fluid conduit in communication with the first fluid conduit and/or the second fluid conduit; and/or e) the outlet is of a tubular shape and defines an axis that is oriented in a direction substantially perpendicular to the direction of the humidification tub insertion axis.

In some examples: a) the tub base includes a tub base opening configured to allow the flow of pressurized breathable gas into and/or out of the cavity; b) the tub base opening includes a passageway configured to receive the third fluid conduit in the operational configuration so that the passageway and the third fluid conduit are coaxial; c) the shroud is positioned adjacent to an opening of the third fluid conduit when the tub lid is coupled to the tub base in the operational configuration; d) at least one of the passageway and the third conduit includes a frustoconical shape; e) the third fluid conduit extends superior to the passageway in an operational configuration f) the third fluid conduit includes a divider that separates the third fluid conduit into an inlet portion and an outlet portion, the divider configured to at least partially isolate the inlet portion from the outlet portion; g) the shroud and the third fluid conduit being so configured that the shroud prevents water from entering the inlet portion and the outlet portion when water is poured into the cavity through the water inlet opening when the humidification tub is into its operational configuration inside the humidification compartment; h) the flow of pressurized breathable gas is configured to enter the cavity through the inlet portion and the flow of pressurized breathable gas is configured to exit the cavity through the outlet portion; i) the divider is configured to extend superior to the passageway of the tub base opening; j) an outer surface adjacent an opening of the third fluid conduit includes a sealing member that is configured to engage an inner surface of the passageway of the tub base opening, the sealing member configured to prevent the flow of pressurized breathable gas between the passageway and the third fluid conduit; and/or k) the sealing member is a silicone lip seal or an O-ring.

In some examples: a) the dock includes a humidification compartment retention feature disposed within the compartment; b) the tub includes a humidification reservoir retention feature located at the tub base exterior to the cavity and configured to reversibly engage with the humidification compartment retention feature; c) the humidification tub is configured to be guided into the operational configuration and/or held into the operational configuration by proper engagement between the humidification compartment retention feature and the humidification reservoir retention feature; d) the humidification compartment retention feature and the humidification reservoir retention features are magnets having opposite polarities; e) each of the humidification compartment retention feature and the humidification reservoir retention feature includes one or more magnets, the arrangement being such that electromagnetic forces between magnets of respective polarity permit only an engagement in the operational configuration; and/or f) the humidification tub is configured to engage with the humidification compartment with a magnetic connection and at least one additional connection selected from the group consisting of a mechanical connection, an electrical, and a pneumatic, wherein the magnetic connection and the additional connection are configured to be effected simultaneously.

In some examples: a) the RPT device is configured to be inserted into the device compartment along an RPT insertion axis and the humidification tub is configured to be inserted into the humidification compartment along a reservoir insertion axis that is parallel to the RPT insertion axis; b) the outlet is oriented in a direction substantially perpendicular to the direction of the RPT insertion axis and the second insertion axis; c) the device compartment is configured to receive only a portion of an engaged RPT device; and/or d) the RPT device is at least partially exposed when completely positioned in the device compartment.

In some examples: a) a medical device comprising: the humidifier; an RPT device configured to supply a flow of pressurized breathable gas, the RPT device being removably positionable within the device compartment of the humidifier; a patient interface configured to seal against the patient's face and deliver the flow of pressurized breathable gas with increased humidity to the patient's airways; and a conduit arranged to fluidly connect the humidifier outlet to the patient interface, so as to deliver the flow of pressurized breathable gas from the humidifier to the patient interface; b) when fully inserted into the device compartment, at least a portion of the RPT device is exposed and configured to be grasped by the patient; and/or c) when fully inserted into the humidification compartment, at least a portion of the humidification tub is exposed and configured to be grasped by the patient.

Another form of the present technology comprises a humidifier for humidifying a flow of pressurized breathable gas to be delivered to a patient, the humidifier comprising:
a dock comprising:
a device compartment,
a humidification compartment spaced apart from the device compartment,
an outlet spaced apart from the device compartment and from the humidification compartment,
a first fluid conduit extending between the device compartment and the humidification compartment, the first fluid conduit configured to covey pressurized breathable gas from the device compartment to the humidification compartment, and
a second fluid conduit extending between the humidification compartment and the outlet, the second fluid conduit configured to covey pressurized breathable gas from the humidification compartment to the outlet; and
a tub configured to contain a supply of water, the tub configured to receive the flow of pressurized breathable gas through the first fluid conduit and output the flow of pressurized breathable gas with increased humidity through the second fluid conduit, the tub comprising:
a tub base including a cavity configured to contain the supply of water, and
a tub lid configured to selectively cover an opening to the cavity;
wherein the device compartment is configured to removably receive a RPT device configured to supply the flow of pressurized breathable gas; and
wherein the tub is removably positionable within the humidification compartment.

Another form of the present technology comprises a humidifier for humidifying a flow of pressurized breathable gas to be delivered to a patient, the humidifier comprising:
a dock comprising:
a dock base having a bottom surface and at least one vertical side wall extending upwardly from the bottom surface, the bottom surface and the at least vertical side wall at least partially forming a compartment,
a compartment inlet configured to convey the flow of pressurized breathable gas into the compartment, and
a humidification compartment retention feature disposed within the compartment; and
a tub configured to contain a supply of water, the tub being removably positionable within the compartment, the tub configured to receive the flow of pressurized breathable gas from the compartment inlet and output the flow of pressurized breathable gas with increased humidity, the tub comprising:
a tub base including a cavity configured to contain the supply of water,
a humidification reservoir retention feature coupled to the tub base exterior to the cavity and configured to removably engage with the humidification compartment retention feature, and
a tub lid removably coupled to the tub base and configured to selectively cover an opening to the cavity;
wherein the tub is configured to be guided into an engaged position by proper engagement between the humidification compartment retention feature and the humidification reservoir retention feature.

Another form of the present technology comprises a humidifier for humidifying a flow of pressurized breathable gas to be delivered to a patient, the humidifier comprising:
a dock comprising:
a dock base having a bottom surface and at least one vertical side wall extending upwardly from the bottom surface, the bottom surface and the at least vertical side wall at least partially forming a compartment, and
a compartment inlet configured to convey the flow of pressurized breathable gas into the compartment, and
a tub configured to contain a supply of water, the tub being removably positionable within the compartment, the tub configured to receive the flow of pressurized breathable gas from the compartment inlet and output the flow of pressurized breathable gas with increased humidity, the tub comprising:
a tub base including a cavity configured to contain the supply of water,
a tub lid removably coupled to the tub base and configured to selectively cover an opening to the cavity, the tub lid including a water inlet passage, and
a cap removably coupled to the tub lid in order to selectively cover the water inlet passage;
wherein the tub lid is exposed to ambient and uncovered by the housing, in use
wherein the cap is removable while the tub base is positioned within the compartment.

Another form of the present technology comprises a humidifier for humidifying a flow of pressurized breathable gas to be delivered to a patient, the humidifier comprising:
a dock comprising:
a device compartment configured to removably receive a RPT device that is configured to supply the flow of pressurized breathable gas, and
a humidification compartment spaced apart from the device compartment and fluidly connected to the device compartment, the humidification compartment including a humidification compartment depth; and
a tub configured to contain a supply of water, the tub configured to receive the flow of pressurized breathable gas and output the flow of pressurized breathable gas with increased humidity, the tub comprising:
a tub base including a cavity configured to contain the supply of water, the tub base including a length;
a tub lid removably coupled to the tub base and configured to selectively cover an opening the cavity;
wherein the tub base and the tub lid as a unit are removably positionable within the humidification compartment;
wherein in use, the tub is configured to be inserted into the humidification compartment along an insertion axis so that the humidification compartment depth and the length are measured parallel to the insertion axis, the length being greater than the humidification compartment depth so that a portion of the tub base is exposed; and
wherein the tub lid is configured to be removed from the tub base along the insertion axis, in use.

Another form of the present technology comprises a humidifier dock for humidifying a flow of pressurized breathable gas to be delivered to a patient, the humidifier dock comprising:
a device compartment configured to at least partially removably receive an RPT device that is configured to supply the flow of pressurized breathable gas; and
a humidification compartment fluidly connected to the device compartment; and
wherein the humidification compartment is configured to at least partially removably receive a humidification tub, the arrangement being such that at least one of the RPT device and the humidification tub is received within the dock in a vertical direction.

In some examples: a) the dock includes the humidification tub; b) the humidification tub is configured to contain a supply of water; and/or c) the humidification is configured to be at least partially removably received in the humidification compartment so that, in operational configuration, the humidification tub is arranged to receive the flow of pressurized breathable gas and output the flow of pressurized breathable gas with increased humidity.

In some examples: a) the tub length is between approximately 25% to approximately 90% greater than the humidification compartment depth; b) the tub length is approximately 66% greater than the humidification compartment depth; c) the humidification compartment includes a fluid passageway extending along the insertion axis; and/or d) the tub base includes a passageway configured to at least partially receive the fluid passageway, in use.

In some examples: a) the dock further includes a humidification compartment retention feature disposed within the humidification compartment; b) the humidification tub further includes a humidification reservoir retention feature located on the humidification tub base exterior to the cavity and configured to removably engage with the first retention feature; c) the humidification tub is configured to be guided into an engaged position by an interaction between the humidification compartment retention feature and the humidification reservoir retention feature; and/or d) each of the humidification compartment retention feature and the humidification reservoir retention feature includes one or more.

In some examples: a) a heater is fixed to the bottom or to a wall of the tub base and configured to heat the supply of water; and/or b) the heater is overmolded to the tub base (to the bottom or to a wall of the tub base).

In some examples: a) the humidification compartment includes a humidification compartment depth; b) the humidification tub includes a tub length; c) in use, the humidification tub is configured to be engageable with the humidification compartment along a vertical insertion axis so that the humidification compartment depth and the tub length are measured parallel to the insertion axis; d) the tub length is greater than the humidification compartment depth so that, when the tub is fully engaged, an upper portion of the tub base extends above the humidification compartment to enable handling by the user; e) the humidification tub includes a base and a lid configured to selectively engage the base; and/or f) the lid is removable from the base when the humidification tub is positioned within the humidification compartment.

In some examples: a) a medical device comprising the humidifier dock; an RPT device having an RPT device length and being configured to supply a flow of pressurized breathable gas, the RPT device being removably positionable within the device compartment; a patient interface configured to seal against patient's airways and deliver the flow of pressurized breathable gas with increased humidity to the patient's airways; and a conduit arranged to fluidly connect the humidifier outlet to the patient interface, so as to deliver the flow of pressurized breathable gas from the humidifier to the patient interface; b) the device compartment is arranged to receive the RPT device in a direction parallel to the insertion axis so that a device compartment depth and the RPT device length are measured parallel to the insertion axis, the RPT device length being greater than the device compartment depth so that a portion of the RPT device is exposed to enable handling by the user; and/or c) the conduit of the patient interface is connected to the dock in a direction substantially perpendicular to the insertion axis.

Another form of the present technology comprises a medical device comprising an RPT device configured to supply a flow of pressurized breathable gas, a humidifier configured to humidify the flow of pressurized breathable gas, and a patient interface configured to deliver the flow of pressurized breathable gas to a patient's airways.

Another form of the present technology comprises a dock for a humidifier for humidifying a flow of pressurized breathable gas to be delivered to a patient, the dock comprising:
a device compartment;
a humidification compartment spaced apart from the device compartment;
wherein the device compartment is configured to receive a portable RPT device; and
wherein the humidification compartment is configured to receive a water reservoir.

Another form of the present technology comprises a system for humidifying a flow of pressurized breathable gas to be delivered to a patient to ameliorate a breathing disorder, the system comprising:
a dock comprising:
a device compartment including a device compartment bottom surface and a device compartment side wall, and
a humidification compartment fluidly connected to the device compartment, the humidification compartment including a humidification compartment bottom surface and a humidification compartment side wall;
an RPT device configured to supply the flow of pressurized breathable gas, the RPT device being removably positionable within the device compartment of the dock, wherein when the RPT device is positioned within the device compartment the device compartment side wall extends partially along the RPT device; and
a humidification tub configured to contain a supply of water and to be at least partially removably received in the humidification compartment so that, in an operational configuration, the humidification tub is arranged to receive the flow of pressurized breathable gas and output the flow of pressurized breathable gas with increased humidity, wherein when the humidification tub is positioned within the device compartment the device compartment side wall extends partially along the humidification tub;
wherein the RPT device is at least partially exposed from the device compartment in an operating position; and
wherein the humidification tub is at least partially exposed from the humidification compartment in an operating position.

In some forms: a) the humidification compartment is spaced apart from the device compartment so that the device compartment side wall is separate from the humidification compartment side wall; b) the device compartment side wall is oriented perpendicularly with respect to the device compartment bottom surface; c) the humidification compartment side wall is oriented perpendicularly with respect to the humidification compartment bottom surface; d) the device compartment side wall is at least partially curved; and/or e) the humidification compartment side wall is at least partially curved.

In some forms: a) the humidification tub is arranged to engage and disengage with the dock along a humidification tub insertion axis oriented substantially perpendicularly with respect to the humidification compartment bottom surface; b) the RPT device is arranged to engage and disengage with the dock along a RPT device insertion axis oriented substantially perpendicularly with respect to the device compartment bottom surface; and/or c) the RPT device and the humidification tub are configured to be inserted into the dock along parallel axes.

In some forms: a) the humidification compartment further includes a humidification compartment retention feature; b) the humidification tub further includes a humidification reservoir retention feature configured to reversibly engage with the humidification compartment retention feature; and/or c) the humidification tub is configured to be guided into the operational configuration and/or held into the operational configuration, by proper engagement between the humidification compartment retention feature and the humidification reservoir retention feature.

In some forms: a) humidification compartment retention feature includes a first magnet and a second magnet having an opposite polarity than the first magnet; b) humidification reservoir retention feature includes a first magnet and a second magnet having an opposite polarity than the first magnet; and/or c) the humidification tub is configured to be guided into the operational configuration and/or held into the operational configuration by aligning the first magnet of the humidification compartment retention feature with the second magnet humidification reservoir retention feature, and by aligning the second magnet of the humidification compartment retention feature with the first magnet humidification reservoir retention feature.

In some forms: a) the humidification compartment further includes a first conductive portion and the humidification tub includes a second conductive portion configured to contact the first conductive portion; b) contact between the first conductive portion and the second conductive portion is configured to provide electrical energy to a heating element on the humidification tub; c) a fluid conduit extends from the humidification compartment bottom surface; d) the humidification tub including a passageway configured to receive the fluid conduit when the humidification tub is received in the humidification compartment; and/or e) the fluid conduit includes a first passage and a second passage parallel to the first passage.

In some forms: a) the dock further includes an outlet configured to output the flow of pressurized breathable gas with increased humidity; b) the outlet perpendicular to the device compartment bottom surface and/or the humidification compartment bottom surface; c) a patient interface configured to seal against the patient's face and deliver the flow of pressurized breathable gas with increased humidity to the patient's airways; and/or d) a conduit arranged to fluidly connect the outlet to the patient interface, so as to deliver the flow of pressurized breathable gas from the humidifier to the patient interface.

Another form of the present technology comprises a humidifier for humidifying a flow of pressurized breathable gas to be delivered to a patient, the humidifier comprising:
a dock comprising:
a device compartment configured to at least partially removably receive an RPT device that is configured to supply the flow of pressurized breathable gas,
a humidification compartment,
an outlet,
a first fluid conduit extending between the device compartment and the humidification compartment, the first fluid conduit configured to covey pressurized breathable gas from the device compartment to the humidification compartment,
a second fluid conduit extending between the humidification compartment and the outlet, the second fluid conduit configured to covey pressurized breathable gas from the humidification compartment to the outlet, and
a third fluid conduit in communication with the first fluid conduit and/or the second fluid conduit;
a humidification tub configured to contain a supply of water and to be at least partially removably received in the humidification compartment so that, in an operational configuration, the humidification tub is arranged to receive the flow of pressurized breathable gas through the first fluid conduit and output the flow of pressurized breathable gas with increased humidity through the second fluid conduit to the outlet;
wherein the humidification tub includes a passageway configured to receive the third fluid conduit in the operational configuration.

In some forms: a) the third fluid conduit extends substantially perpendicularly out of the humidification compartment; b) the third fluid compartment includes a divider forming a first pathway and a second pathway; c) the first pathway configured to convey the flow of pressurized breathable gas from the first fluid conduit into the humidification tub; d) the second pathway configured to convey the flow of pressurized breathable gas with increased humidity to the second fluid conduit; and/or e) the divider extends beyond an end of the third fluid conduit.

In some forms: a) the third fluid conduit extends superior to the passageway in the operational configuration; b) at least one of the passageway and the third fluid conduit includes a frustoconical shape; c) the outlet is oriented substantially perpendicularly with respect to the third conduit; d) the first fluid conduit extends substantially perpendicularly into the device compartment; e) the device compartment includes a first side wall and the humidification compartment includes a second side wall spaced apart from the first side wall.

Another form of the present technology comprises a medical device comprising:
the humidifier of any one of the previous forms;
an RPT device configured to supply a flow of pressurized breathable gas, the RPT device being removably positionable within the device compartment of the humidifier; and
a patient interface configured to seal against the patient's face and deliver the flow of pressurized breathable gas with increased humidity to the patient's airways;
a conduit arranged to fluidly connect the outlet to the patient interface, so as to deliver the flow of pressurized breathable gas from the humidifier to the patient interface.

In some forms: a) when fully inserted into the device compartment, at least a portion of the RPT device is exposed and configured to be grasped by the patient; and/or b) when fully inserted into the humidification compartment, at least a portion of the humidification tub is exposed and configured to be grasped by the patient.

An aspect of one form of the present technology is a portable RPT device that may be carried by a person, e.g., around the home of the person.

An aspect of one form of the present technology is a portable humidifier that may be carried by a person, e.g., around the home of the person.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Respiratory Therapy Systems

FIG. 1A shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

4.2 Respiratory System and Facial Anatomy

FIG. 2A shows an overview of a human respiratory system including the nasal and oral cavities, the larynx, vocal folds, oesophagus, trachea, bronchus, lung, alveolar sacs, heart and diaphragm.

4.3 Patient Interface

FIG. 3A shows a patient interface in the form of a nasal mask in accordance with one form of the present technology.

FIG. 3B shows a schematic of a cross-section through a structure at a point. An outward normal at the point is indicated. The curvature at the point has a positive sign, and a relatively large magnitude when compared to the magnitude of the curvature shown in FIG. 3C.

FIG. 3C shows a schematic of a cross-section through a structure at a point. An outward normal at the point is indicated. The curvature at the point has a positive sign, and a relatively small magnitude when compared to the magnitude of the curvature shown in FIG. 3B.

FIG. 3D shows a schematic of a cross-section through a structure at a point. An outward normal at the point is indicated. The curvature at the point has a value of zero.

FIG. 3E shows a schematic of a cross-section through a structure at a point. An outward normal at the point is indicated. The curvature at the point has a negative sign, and a relatively small magnitude when compared to the magnitude of the curvature shown in FIG. 3F.

FIG. 3F shows a schematic of a cross-section through a structure at a point. An outward normal at the point is indicated. The curvature at the point has a negative sign, and a relatively large magnitude when compared to the magnitude of the curvature shown in FIG. 3E.

FIG. 3G shows a cushion for a mask that includes two pillows. An exterior surface of the cushion is indicated. An edge of the surface is indicated. Dome and saddle regions are indicated.

FIG. 3H shows a cushion for a mask. An exterior surface of the cushion is indicated. An edge of the surface is indicated. A path on the surface between points A and B is indicated. A straight line distance between A and B is indicated. Two saddle regions and a dome region are indicated.

4.4 RPT Device

FIG. 4A shows an RPT device in accordance with one form of the present technology.

FIG. 4B is a schematic diagram of the pneumatic path of an RPT device in accordance with one form of the present technology. The directions of upstream and downstream are indicated with reference to the blower and the patient interface. The blower is defined to be upstream of the patient interface and the patient interface is defined to be downstream of the blower, regardless of the actual flow direction at any particular moment. Items which are located within the pneumatic path between the blower and the patient interface are downstream of the blower and upstream of the patient interface.

4.5 Humidifier

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Respiratory Therapy Systems

In one form, the present technology comprises a respiratory therapy system for treating a respiratory disorder. The respiratory therapy system may comprise an RPT device 4000 for supplying a flow of air to the patient 1000 via an air circuit 4170 and a patient interface 3000 or 3800.

5.3 Patient Interface

Figure 1A:
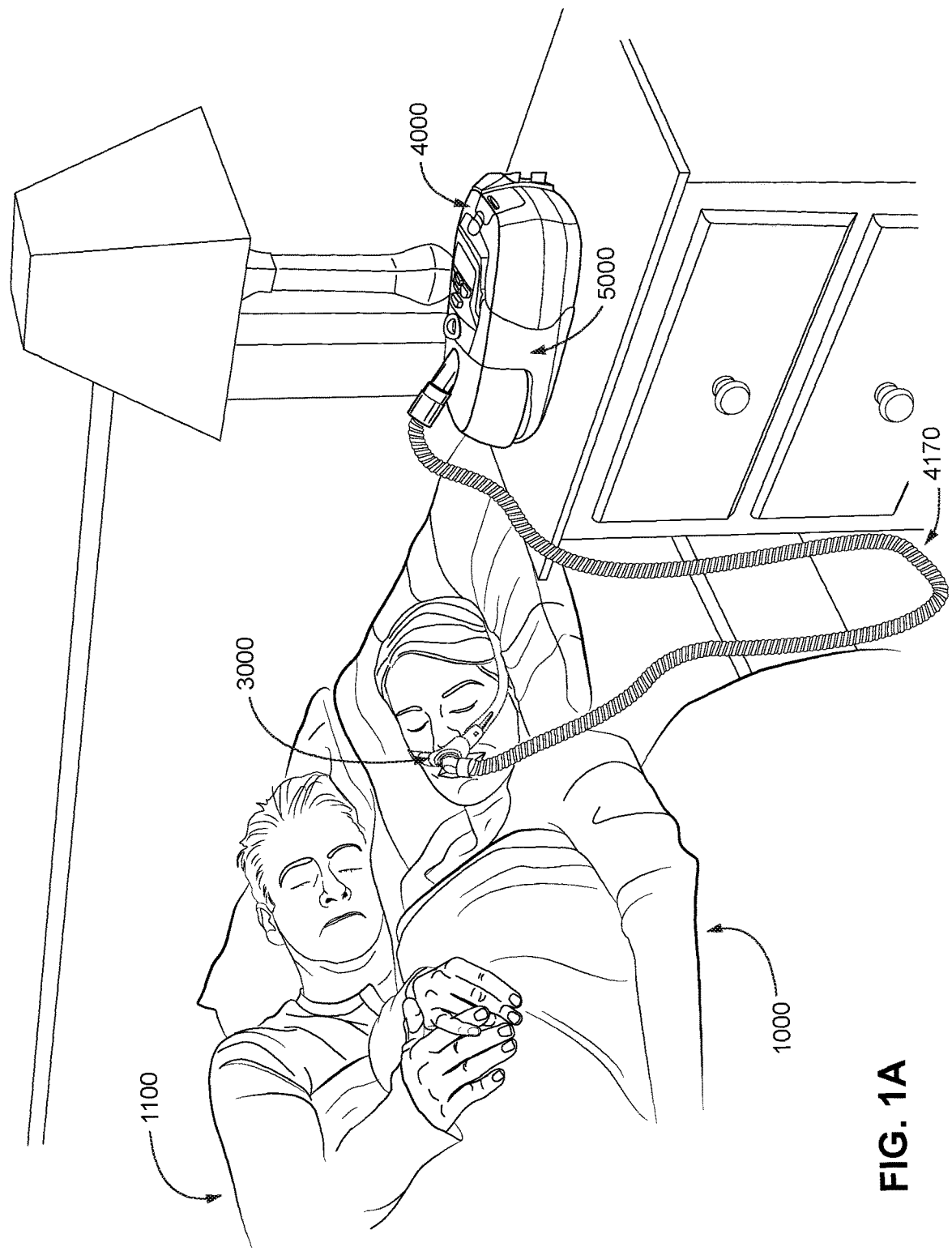
Figure 1B:
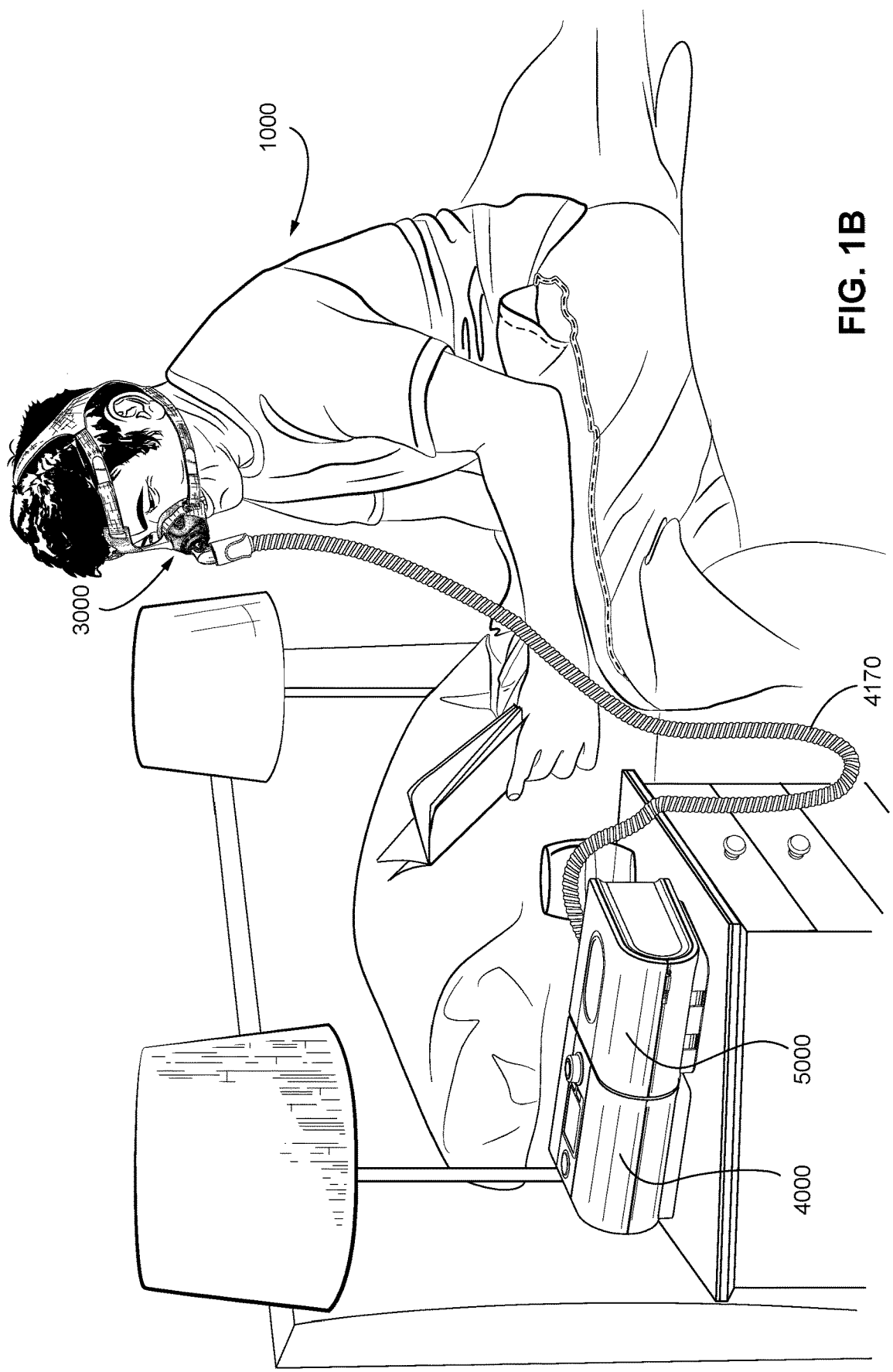
Figure 1C:
Figure 2A:
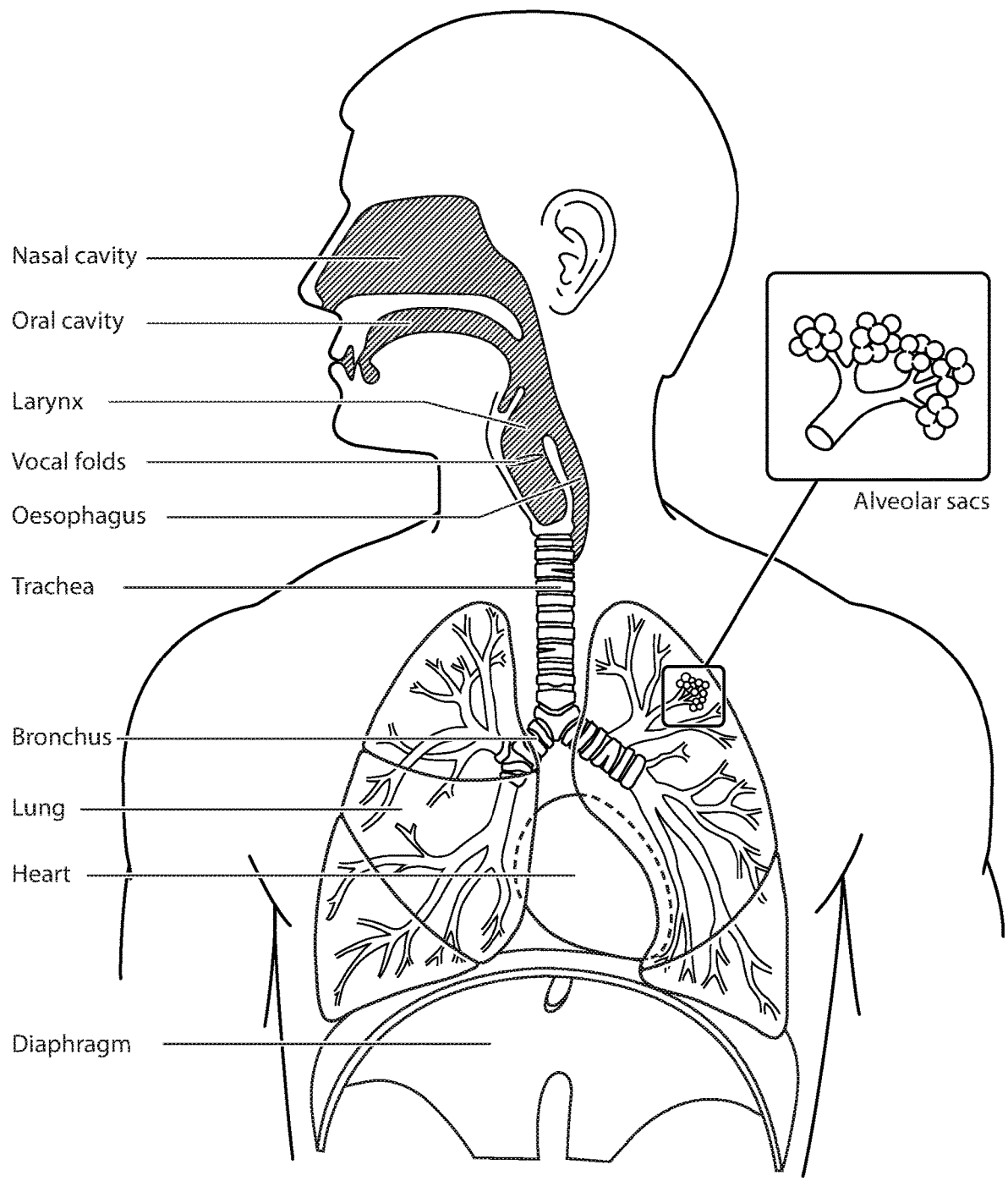
Figure 3A:
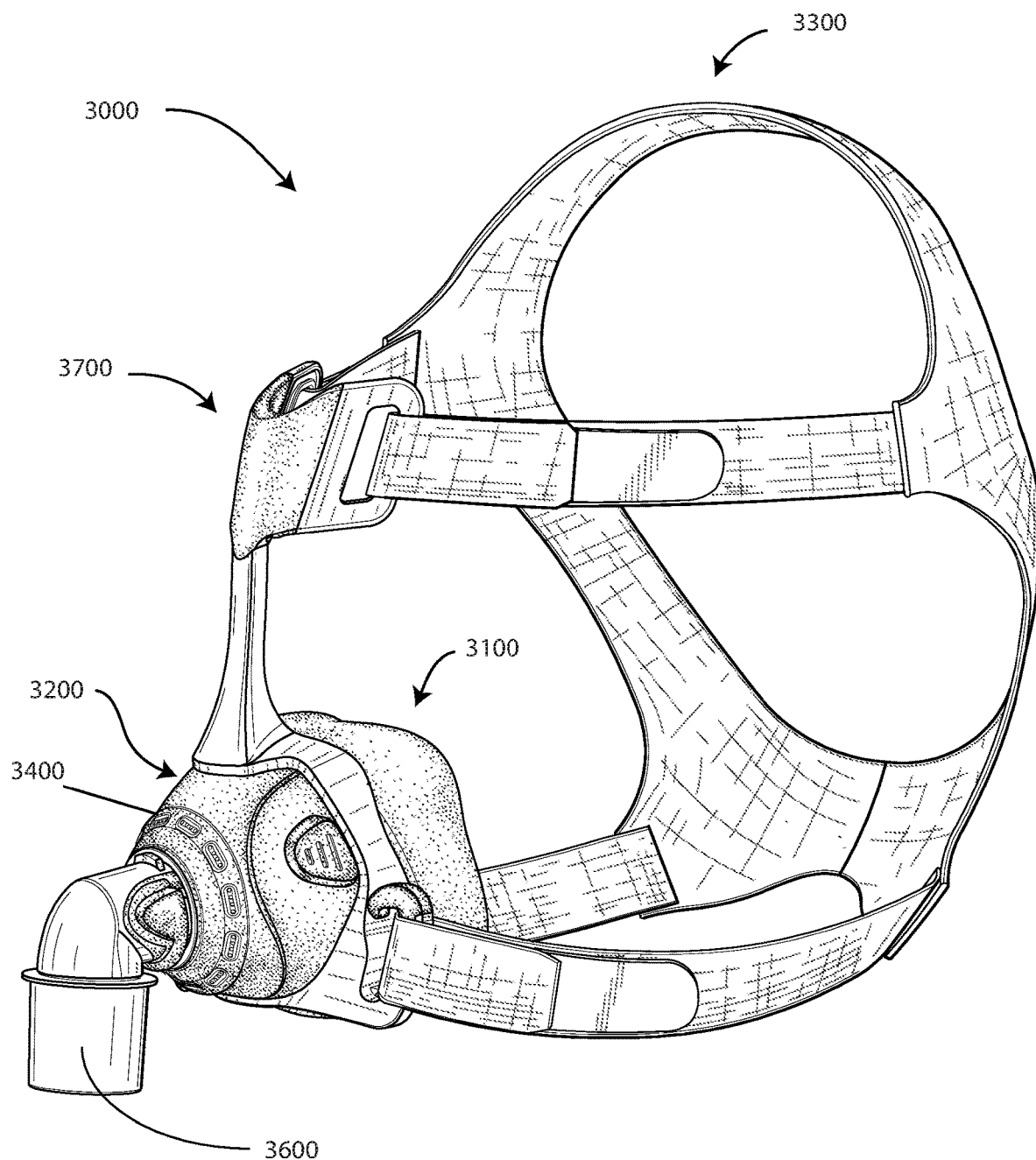
Figure 3H:
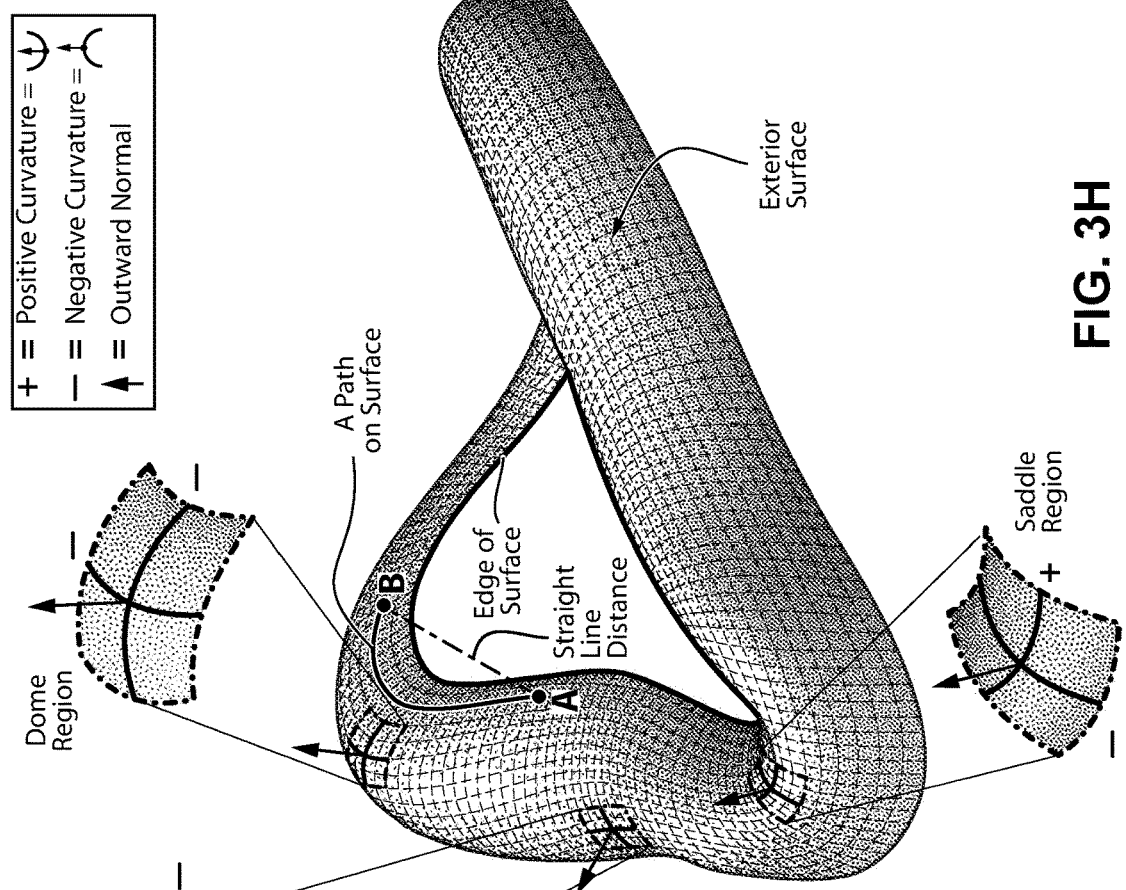
Figure 3G:
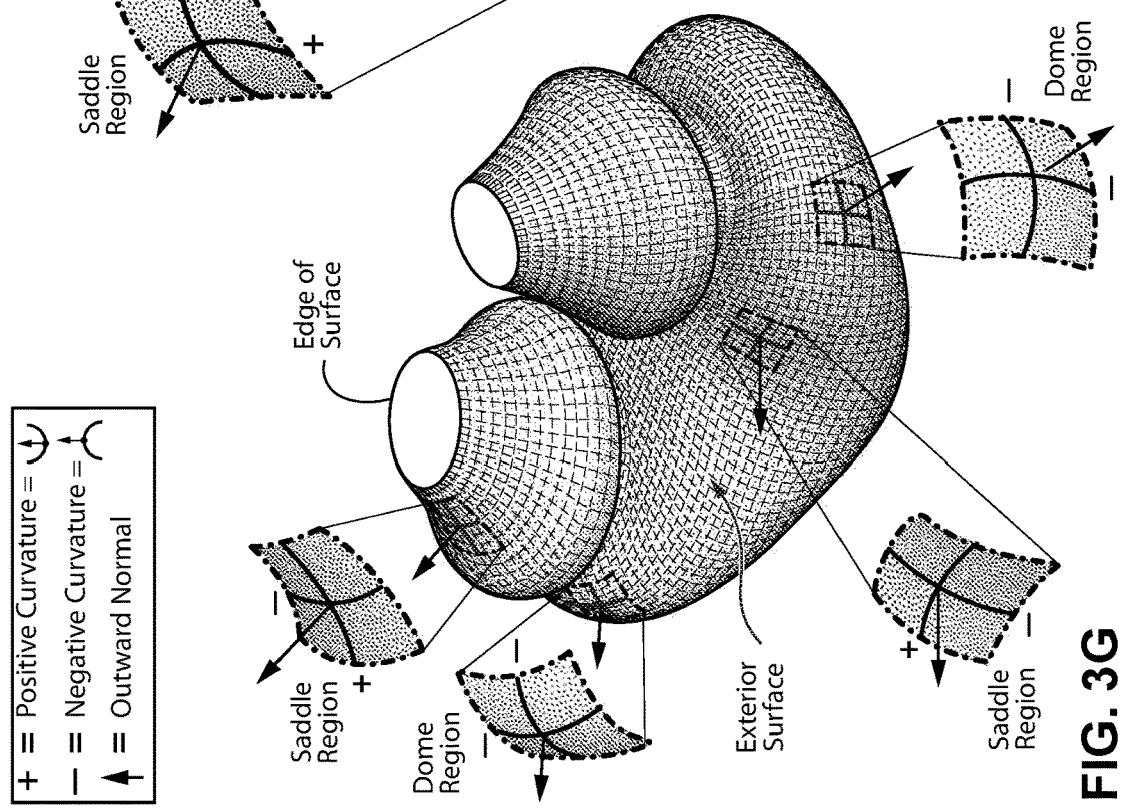

As shown in FIG. 3A, a non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to maintain positive pressure at the entrance(s) to the airways of the patient 1000. The sealed patient interface 3000 is therefore suitable for delivery of positive pressure therapy.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 $cmH_2O$ with respect to ambient.

The patient interface 3000 in accordance with one form of the present technology is constructed and arranged to be able to provide a supply of air at a positive pressure of at least 10 $cmH_2O$ with respect to ambient.

The patient interface 3000 in accordance with one form of the present technology is constructed and arranged to be able to provide a supply of air at a positive pressure of at least 20 $cmH_2O$ with respect to ambient.

5.3.1 Seal-Forming Structure

In one form of the present technology, a seal-forming structure 3100 of FIG. 3A provides a target seal-forming region, and may additionally provide a cushioning function. The target seal-forming region is a region on the seal-forming structure 3100 where sealing may occur. The region where sealing actually occurs—the actual sealing surface—may change within a given treatment session, from day to day, and from patient to patient, depending on a range of factors including for example, where the patient interface was placed on the face, tension in the positioning and stabilising structure and the shape of a patient's face.

In one form the target seal-forming region is located on an outside surface of the seal-forming structure 3100.

In certain forms of the present technology, the seal-forming structure 3100 is constructed from a biocompatible material, e.g. silicone rubber.

A seal-forming structure 3100 in accordance with the present technology may be constructed from a soft, flexible, resilient material such as silicone.

In certain forms of the present technology, a system is provided comprising more than one a seal-forming structure 3100, each being configured to correspond to a different size and/or shape range. For example, the system may comprise one form of a seal-forming structure 3100 suitable for a large sized head, but not a small sized head and another suitable for a small sized head, but not a large sized head. Vent In one form, the patient interface 3000 includes a vent 3400 constructed and arranged to allow for the washout of exhaled gases, e.g. carbon dioxide.

In certain forms the vent 3400 is configured to allow a continuous vent flow from an interior of the plenum chamber 3200 to ambient whilst the pressure within the plenum chamber is positive with respect to ambient. The vent 3400 is configured such that the vent flow rate has a magnitude sufficient to reduce rebreathing of exhaled $CO_2$ by the patient while maintaining the therapeutic pressure in the plenum chamber in use.

One form of vent 3400 in accordance with the present technology comprises a plurality of holes, for example, about 20 to about 80 holes, or about 40 to about 60 holes, or about 45 to about 55 holes.

The vent 3400 may be located in the plenum chamber 3200. Alternatively, the vent 3400 is located in a decoupling structure, e.g., a swivel.

5.3.2 Decoupling Structure(s)

In one form the patient interface 3000 includes at least one decoupling structure, for example, a swivel, a ball and socket, and/or an elbow.

5.3.3 Connection Port

Connection port 3600 allows for connection to the air circuit 4170.

5.3.4 Forehead Support

In one form, the patient interface 3000 includes a forehead support 3700.

5.3.5 Anti-Asphyxia Valve

In one form, the patient interface 3000 includes an anti-asphyxia valve.

5.3.6 Ports

In one form of the present technology, a patient interface 3000 includes one or more ports that allow access to the volume within the plenum chamber 3200. In one form this allows a clinician to supply supplementary oxygen. In one form, this allows for the direct measurement of a property of gases within the plenum chamber 3200, such as the pressure.

5.4 RPT Device

Figure 4A:
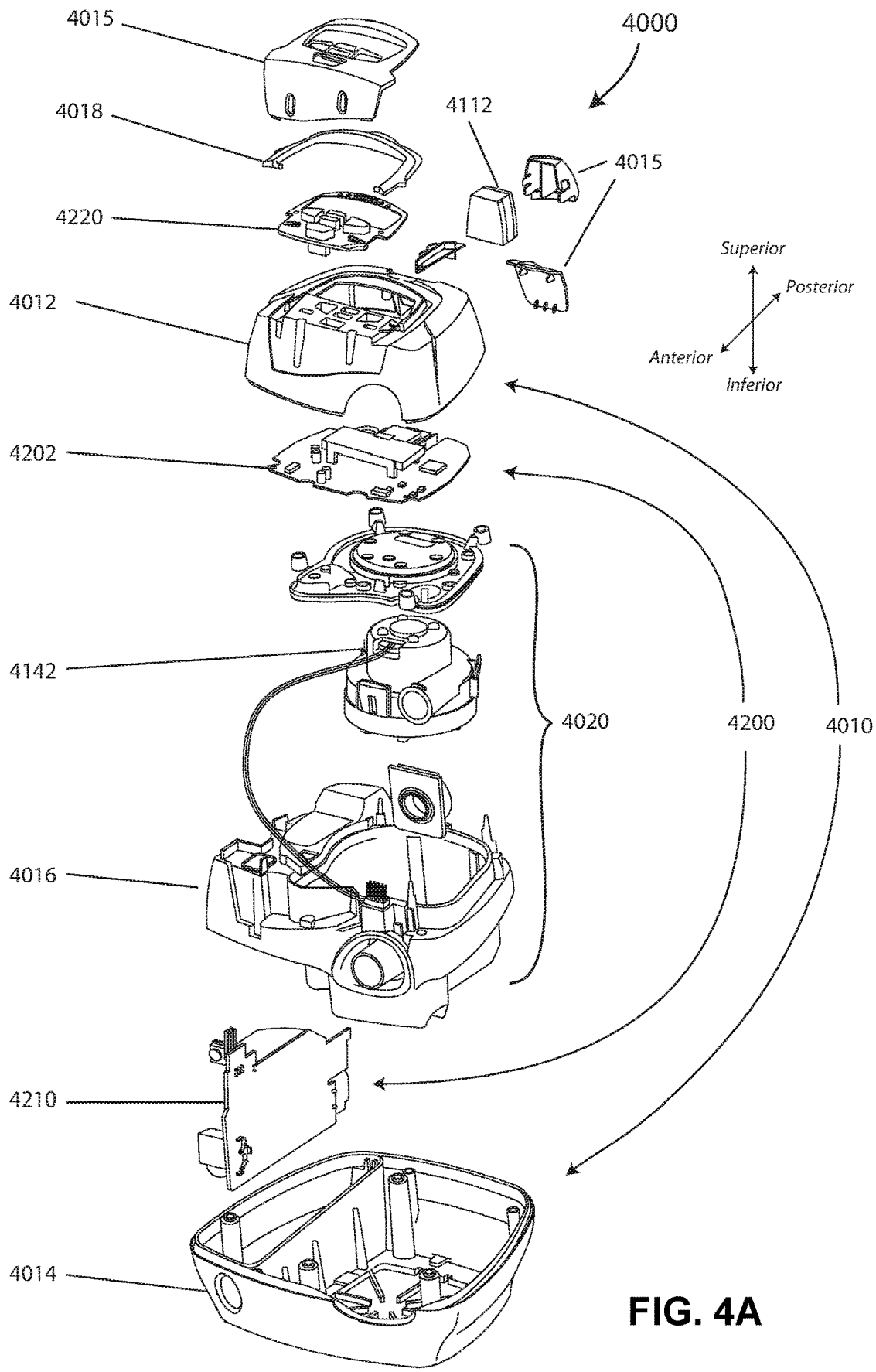
Figure 4B:
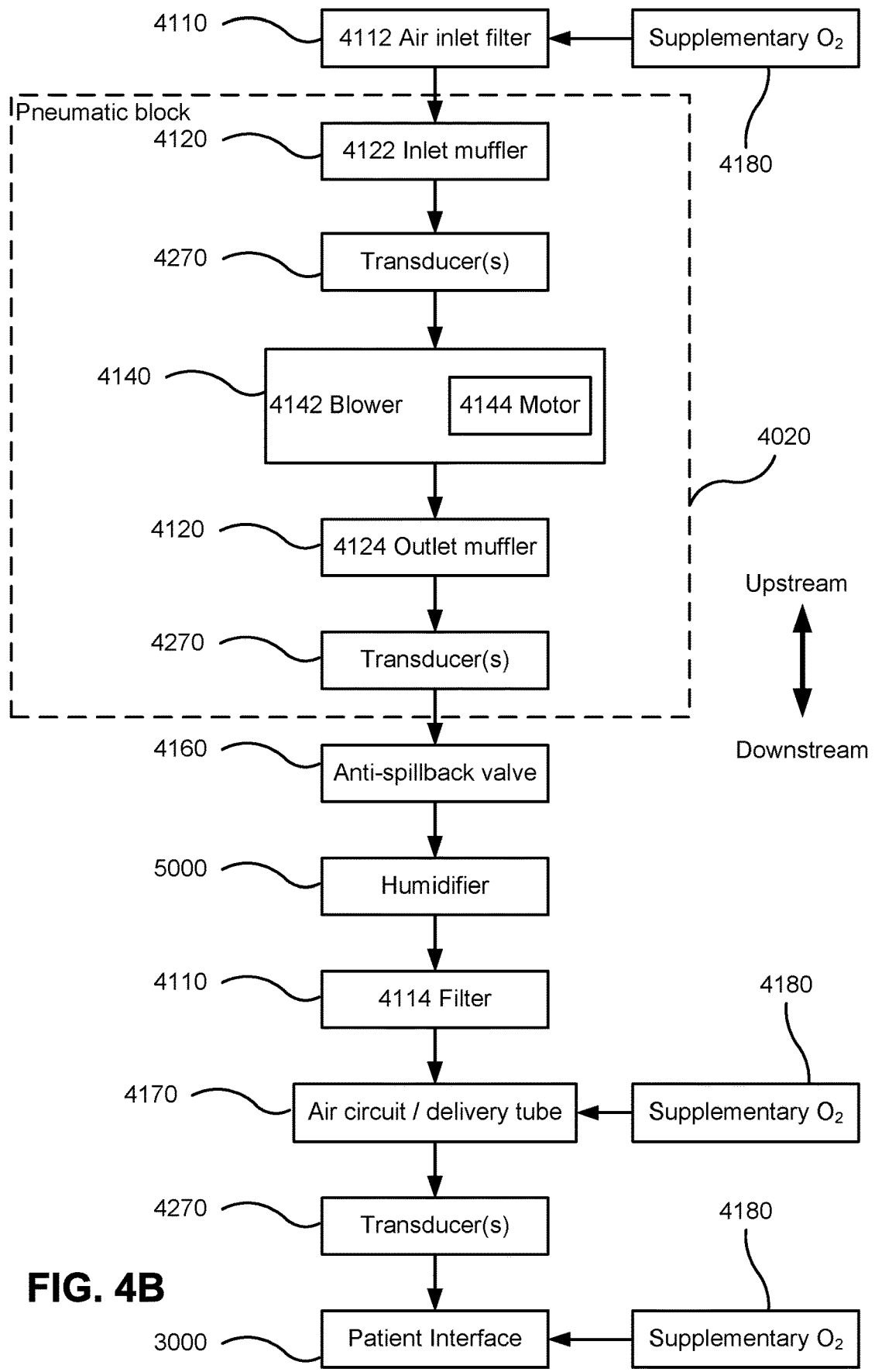

As shown in FIGS. 4A and 4B, an RPT device 4000 in accordance with one aspect of the present technology comprises mechanical, pneumatic, and/or electrical components and is configured to execute one or more algorithms, such as any of the methods, in whole or in part, described herein. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 $cmH_2O$, or at least $10 cmH_2O$, or at least 20 $cmH_2O$.

The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors and flow rate sensors.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a pressure generator 4140, one or more protection circuits, memory, transducers 4270. Electrical components 4200 may be mounted on a single Printed Circuit Board Assembly (PCBA) 4202. In an alternative form, the RPT device 4000 may include more than one PCBA 4202.

5.4.1 RPT Device Mechanical & Pneumatic Components

An RPT device may comprise one or more of the following components in an integral unit. In an alternative form, one or more of the following components may be located as respective separate units.

In some forms, the RPT device may be portable.

In some forms, the RPT device may be modular. For example, the RPT device may be removably coupled with other systems (e.g., an external battery, a humidifier, etc.). The RPT device may be operable as an individual unit (e.g., without another modular system) or when connected with one of the other systems. In some forms, a dock may be used to connect the various modular systems together. In other words, when usable alone, the RPT device may be operational without being connected to the dock. The RPT device may be coupled to the dock only when usable with one of the other systems.

5.4.1.1 Air Filter(s)

An RPT device in accordance with one form of the present technology may include an air filter 4110, or a plurality of air filters 4110.

In one form, an inlet air filter 4112 is located at the beginning of the pneumatic path upstream of a pressure generator 4140.

In one form, an outlet air filter 4114, for example an antibacterial filter, is located between an outlet of the pneumatic block 4020 and a patient interface 3000.

5.4.1.2 Muffler(s)

An RPT device in accordance with one form of the present technology may include a muffler 4120, or a plurality of mufflers 4120.

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface 3000.

5.4.1.3 Pressure Generator

In one form of the present technology, a pressure generator 4140 for producing a flow, or a supply, of air at positive pressure is a controllable blower 4142. For example, the blower 4142 may include a brushless DC motor 4144 with one or more impellers. The impellers may be located in a volute. The blower may be capable of delivering a supply of air, for example at a rate of up to about 120 litres/minute, at a positive pressure in a range from about 4 cmH$_2$O to about 20 cmH$_2$O, or in other forms up to about 30 cmH$_2$O when delivering respiratory pressure therapy. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

The pressure generator 4140 may be under the control of the therapy device controller.

In other forms, a pressure generator 4140 may be a piston-driven pump, a pressure regulator connected to a high pressure source (e.g. compressed air reservoir), or a bellows.

5.4.1.4 Transducer(s)

Transducers may be internal of the RPT device, or external of the RPT device. External transducers may be located for example on or form part of the air circuit, e.g., the patient interface. External transducers may be in the form of non-contact sensors such as a Doppler radar movement sensor that transmit or transfer data to the RPT device.

In one form of the present technology, one or more transducers 4270 are located upstream and/or downstream of the pressure generator 4140. The one or more transducers 4270 may be constructed and arranged to generate signals representing properties of the flow of air such as a flow rate, a pressure or a temperature at that point in the pneumatic path.

In one form of the present technology, one or more transducers 4270 may be located proximate to the patient interface 3000 or 3800.

In one form, a signal from a transducer 4270 may be filtered, such as by low-pass, high-pass or band-pass filtering.

5.4.1.5 Anti-Spill Back Valve

In one form of the present technology, an anti-spill back valve 4160 is located between the humidifier 5000 and the pneumatic block 4020. The anti-spill back valve is constructed and arranged to reduce the risk that water will flow upstream from the humidifier 5000, for example to the motor 4144.

5.4.2 RPT Device Electrical Components

5.4.2.1 Power Supply

A power supply 4210 may be located internal or external of the external housing 4010 of the RPT device 4000.

In one form of the present technology, power supply 4210 provides electrical power to the RPT device 4000 only. In another form of the present technology, power supply 4210 provides electrical power to both RPT device 4000 and humidifier 5000.

5.4.2.2 Input Devices

In one form of the present technology, an RPT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to a central controller.

In one form, the input device 4220 may be constructed and arranged to allow a person to select a value and/or a menu option.

5.5 Air Circuit

An air circuit 4170 in accordance with an aspect of the present technology is a conduit or a tube constructed and arranged to allow, in use, a flow of air to travel between two components such as RPT device 4000 and the patient interface 3000.

In particular, the air circuit 4170 may be in fluid connection with the outlet of the pneumatic block 4020 and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller. One example of an air circuit 4170 comprising a heated wire circuit is described in U.S. Pat. No. 8,733,349, which is incorporated herewithin in its entirety by reference.

5.5.1 Supplementary Gas Delivery

In one form of the present technology, supplementary gas, e.g. oxygen, 4180 is delivered to one or more points in the pneumatic path, such as upstream of the pneumatic block 4020, to the air circuit 4170, and/or to the patient interface 3000.

5.6 Humidifier

5.6.1 Humidifier Overview

Figure 5A:
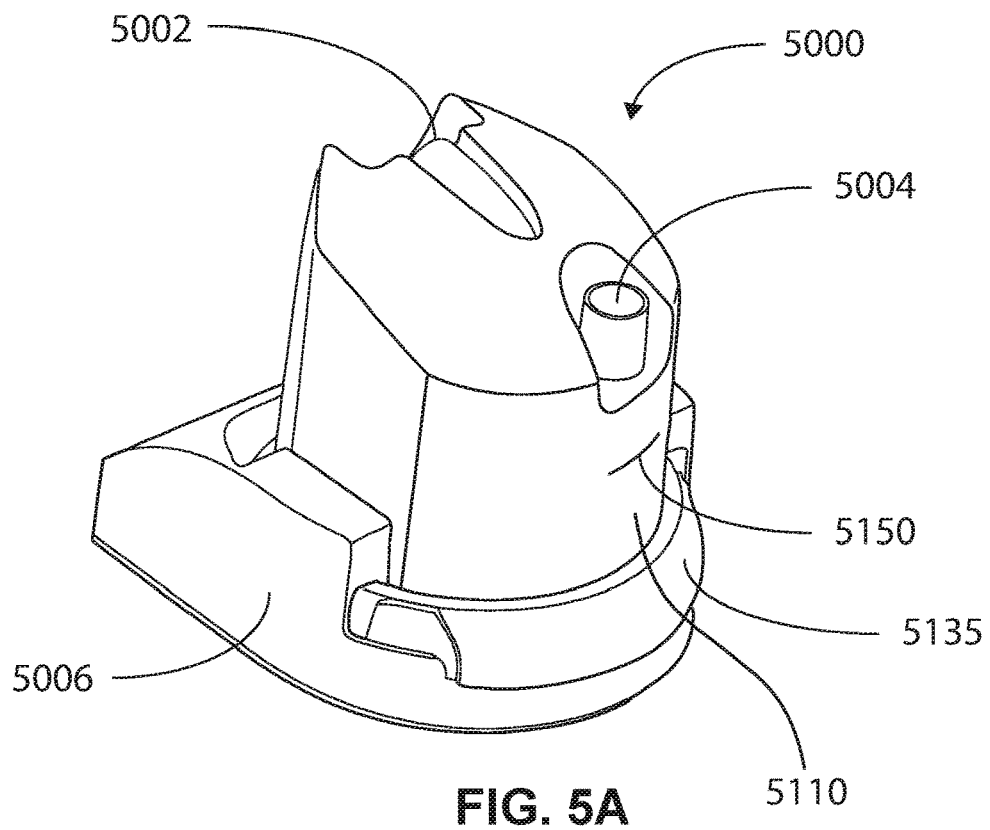
FIG. 5A shows an isometric view of a humidifier in accordance with one form of the present technology.

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

Figure 5B:
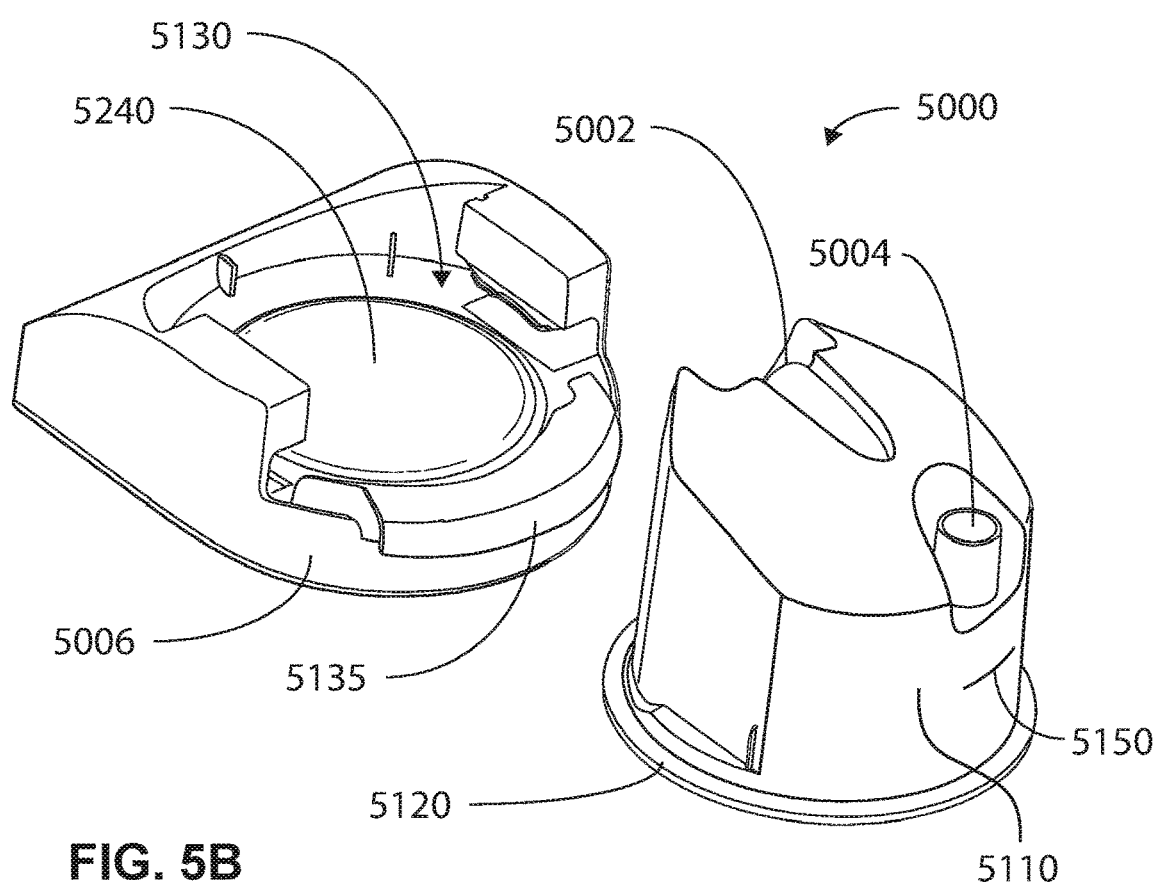
FIG. 5B shows an isometric view of a humidifier in accordance with one form of the present technology, showing a humidifier reservoir 5110 removed from the humidifier reservoir dock 5130.

The humidifier 5000 may comprise a humidification tub or humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

5.6.2 Humidifier Components
5.6.2.1 Water Reservoir

According to one arrangement, the humidifier 5000 may comprise a water reservoir 5110 configured to hold, or retain, a volume of liquid (e.g. water) to be evaporated for humidification of the flow of air. The water reservoir 5110 may be configured to hold a predetermined maximum volume of water in order to provide adequate humidification for at least the duration of a respiratory therapy session, such as one evening of sleep. Typically, the reservoir 5110 is configured to hold several hundred millilitres of water, e.g. 300 millilitres (ml), 325 ml, 350 ml or 400 ml. In other forms, the humidifier 5000 may be configured to receive a supply of water from an external water source such as a building's water supply system.

According to one aspect, the water reservoir 5110 is configured to add humidity to a flow of air from the RPT device 4000 as the flow of air travels therethrough. In one form, the water reservoir 5110 may be configured to encourage the flow of air to travel in a tortuous path through the reservoir 5110 while in contact with the volume of water therein.

According to one form, the reservoir 5110 may be removable from the humidifier 5000, for example in a lateral direction as shown in FIG. 5A and FIG. 5B.

The reservoir 5110 may also be configured to discourage egress of liquid therefrom, such as when the reservoir 5110 is displaced and/or rotated from its normal, working orientation, such as through any apertures and/or in between its sub-components. As the flow of air to be humidified by the humidifier 5000 is typically pressurised, the reservoir 5110 may also be configured to prevent losses in pneumatic pressure through leak and/or flow impedance.

Figure 5C:
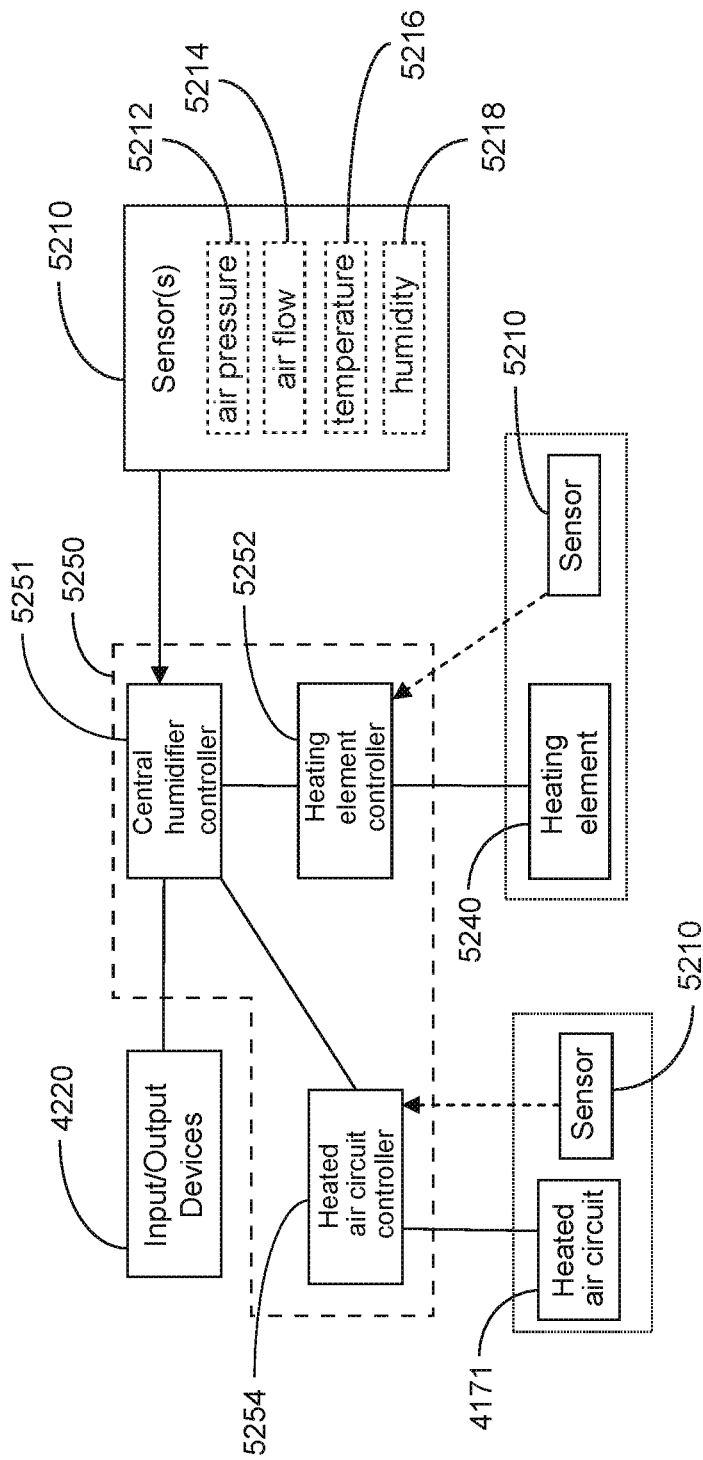
FIG. 5C shows a schematic of a humidifier in accordance with one form of the present technology.
Figure 5D:
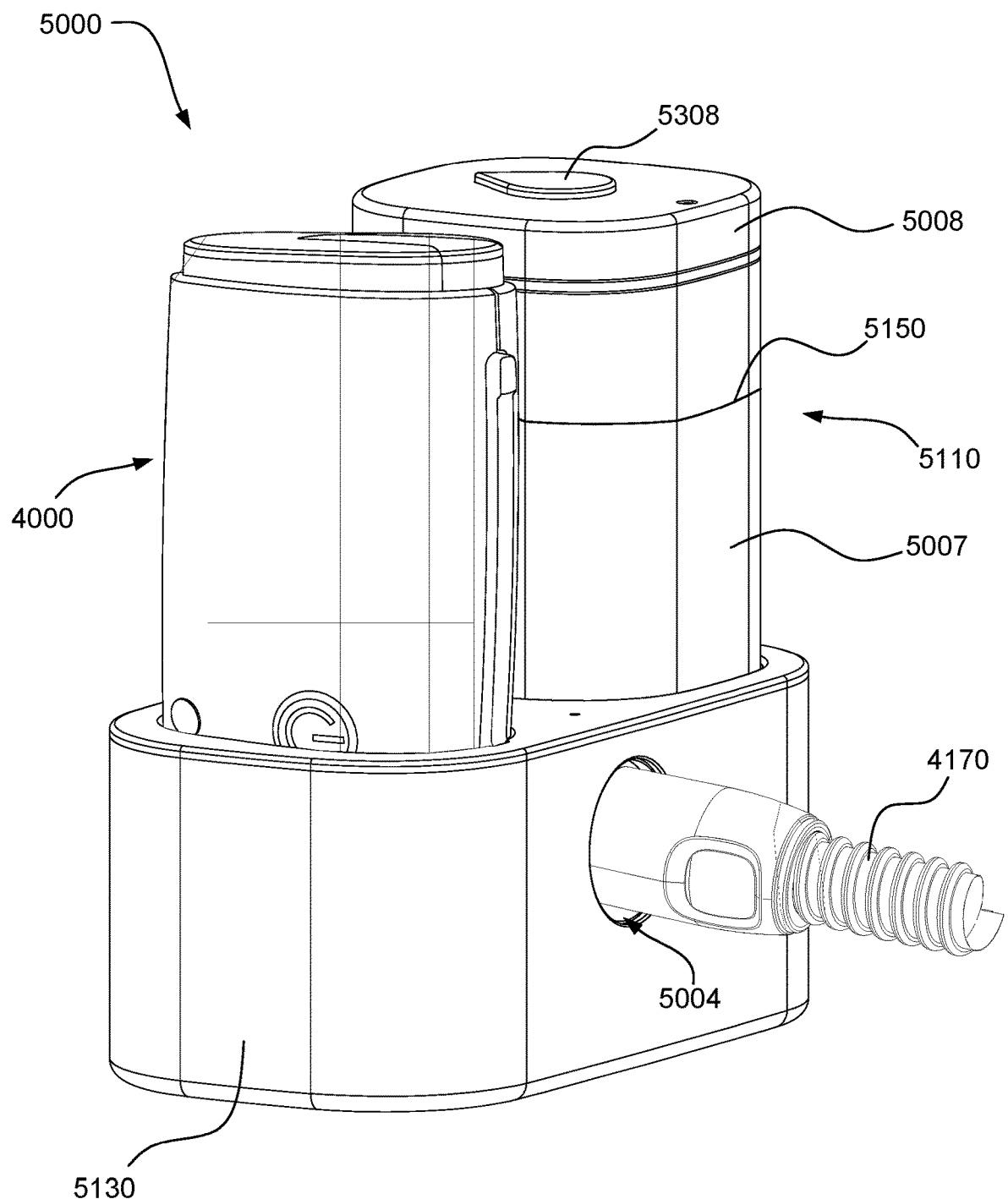
FIG. 5D shows a perspective view of a humidifier base supporting an RPT device and a water reservoir.
Figure 5E:
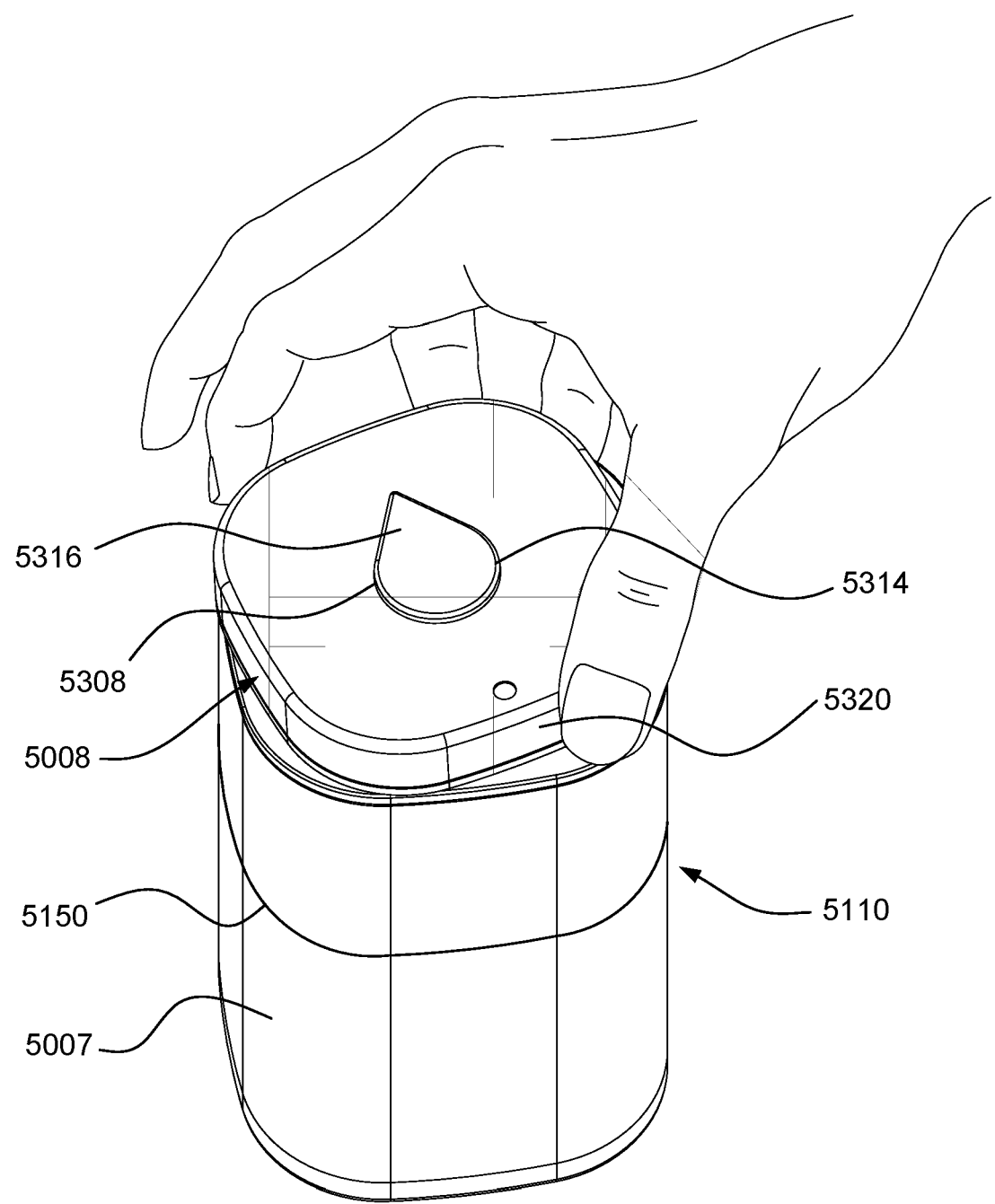
FIG. 5E shows a perspective view of the water reservoir of FIG. 5D, having a base and a lid coupled to one another.
Figure 5F:
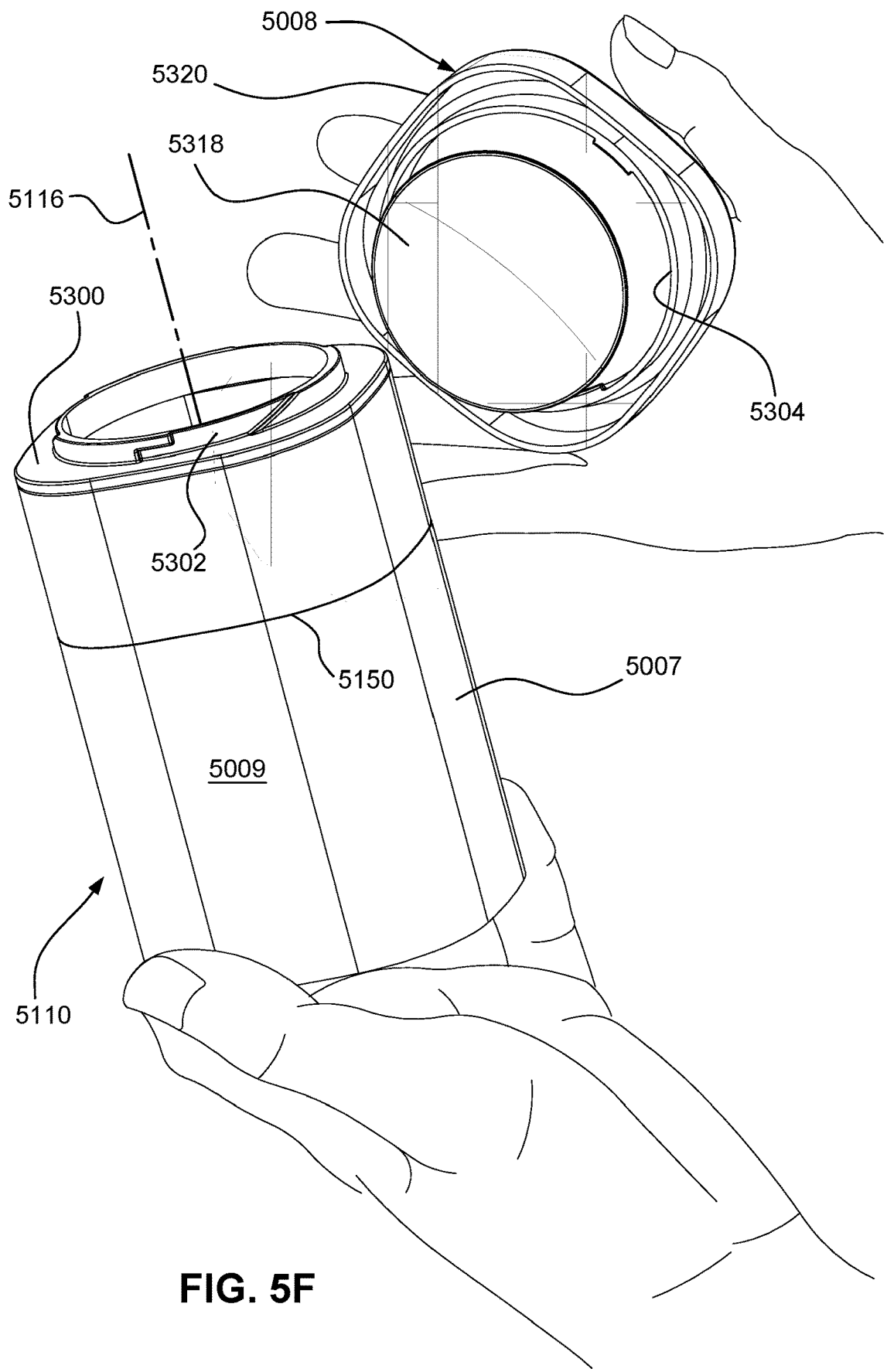
FIG. 5F shows a perspective view of the water reservoir of FIGS. 5D and 5E, with the lid uncoupled from the base.
Figure 5G:
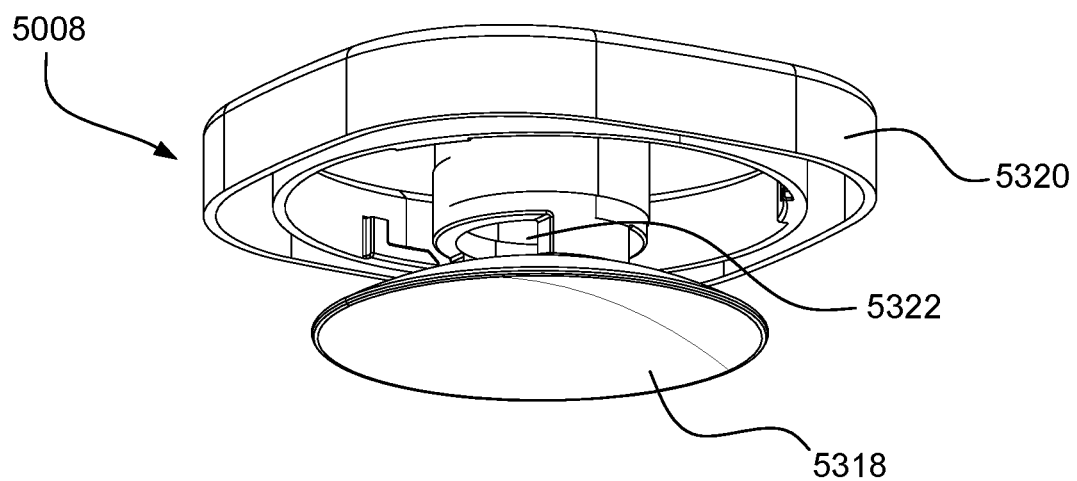
FIG. 5G shows a lower perspective view of the lid of the water reservoir of FIGS. 5D to 5F.
Figure 5H:
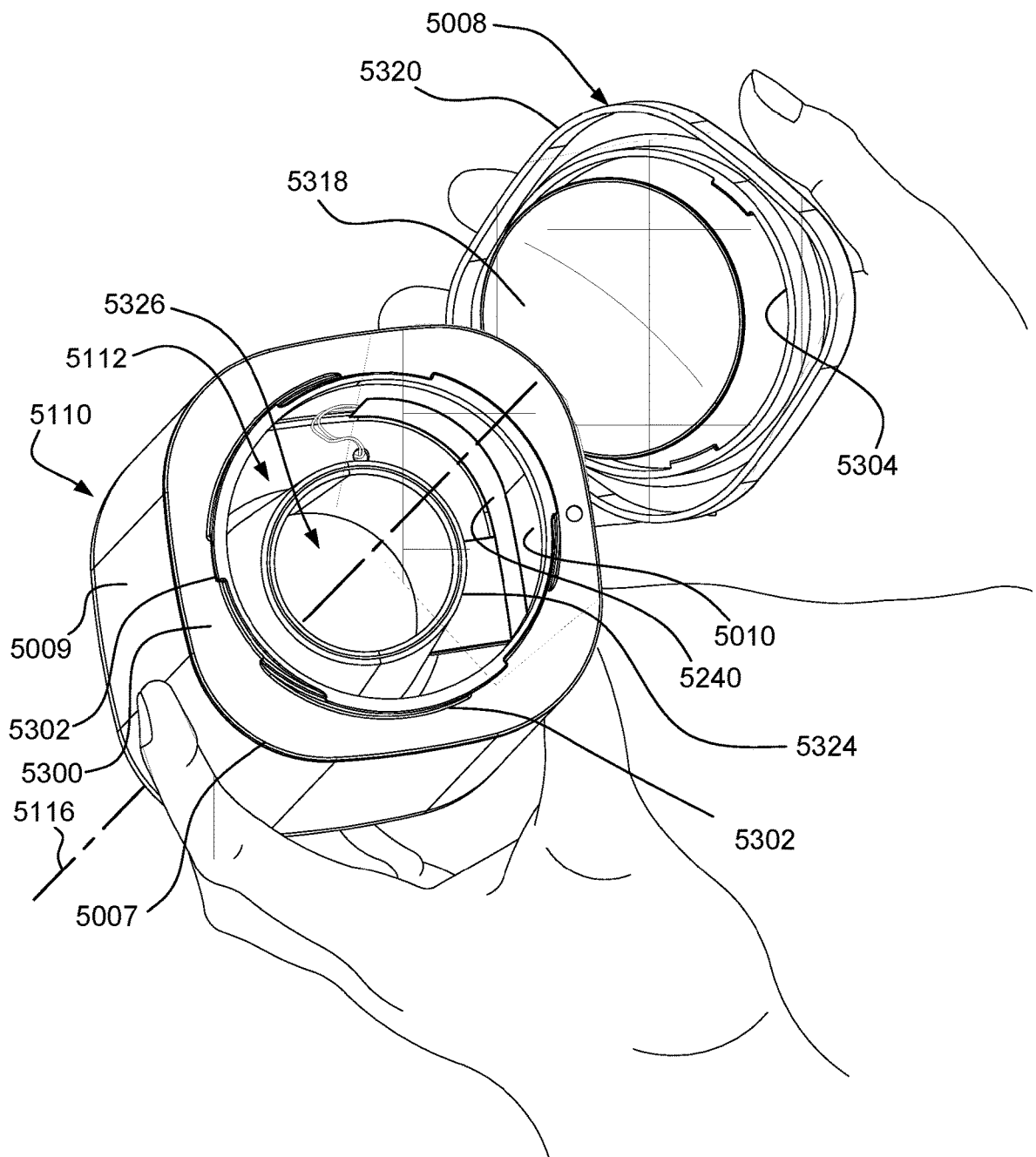
FIG. 5H shows a top view of the base of the water reservoir of FIGS. 5D to 5F, with the lid removed.
Figure 5I:
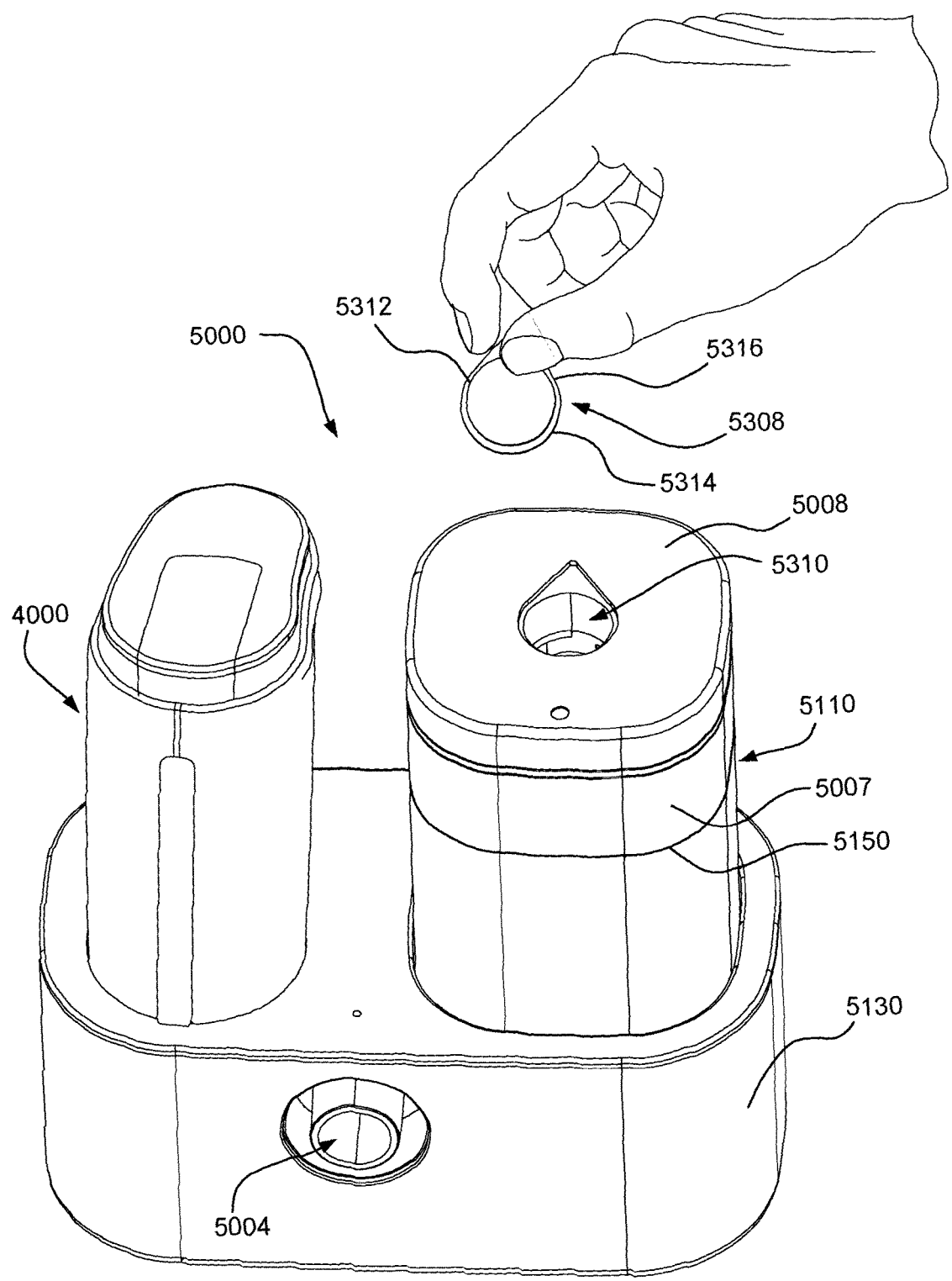
FIG. 5I shows a perspective view of the water RPT device and the reservoir of FIG. 5D, with the lid, coupled to the base, and a cap uncoupled from the reservoir lid exposing a water inlet passage in communication with the base.
Figure 5J:
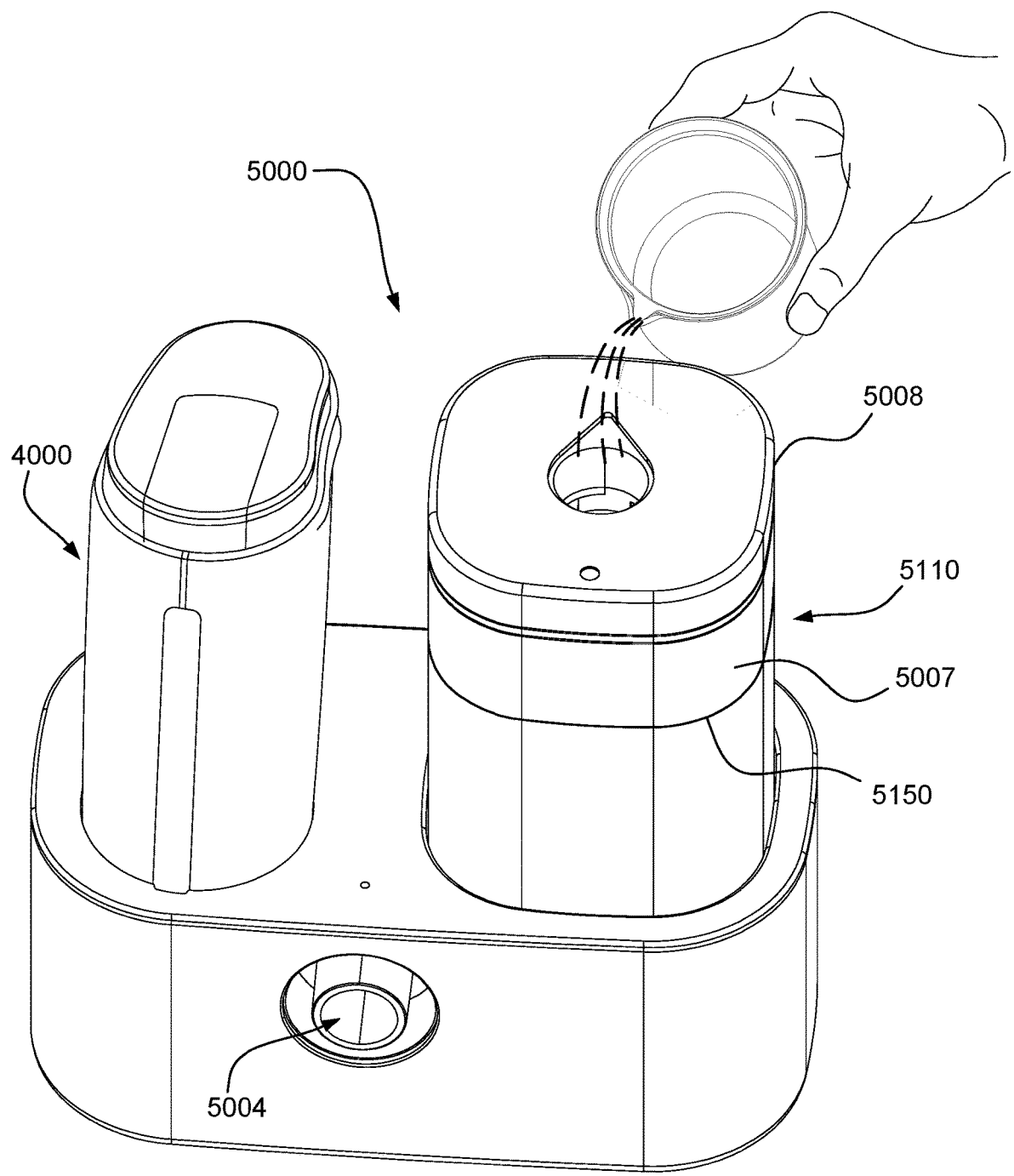
FIG. 5J shows a perspective view of the water reservoir of FIG. 5I, illustrating a patient adding water to the water reservoir through the water inlet passage.
Figure 5K:
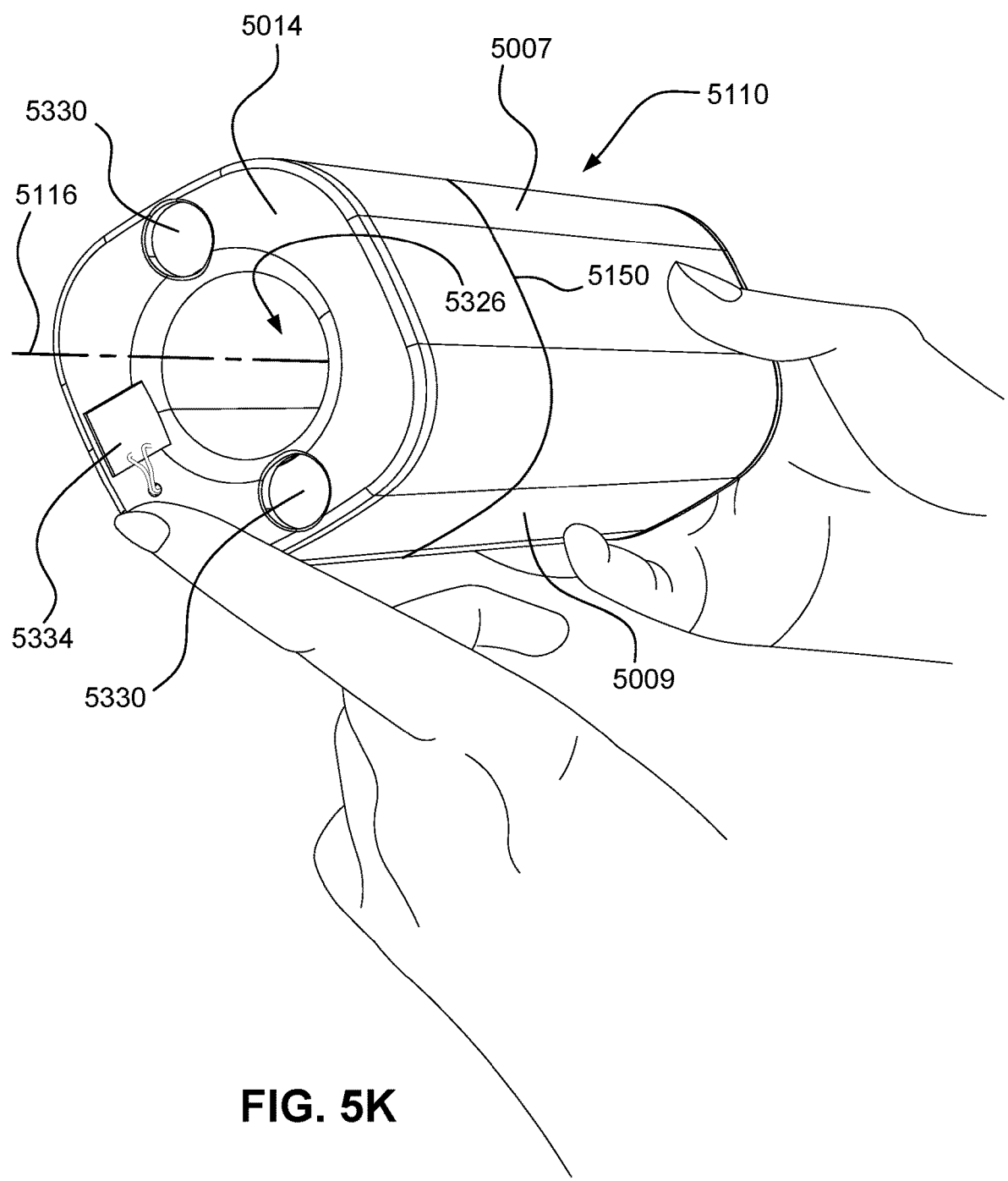
FIG. 5K shows a bottom perspective view of the water reservoir of FIGS. 5D to 5J.
Figure 5L:
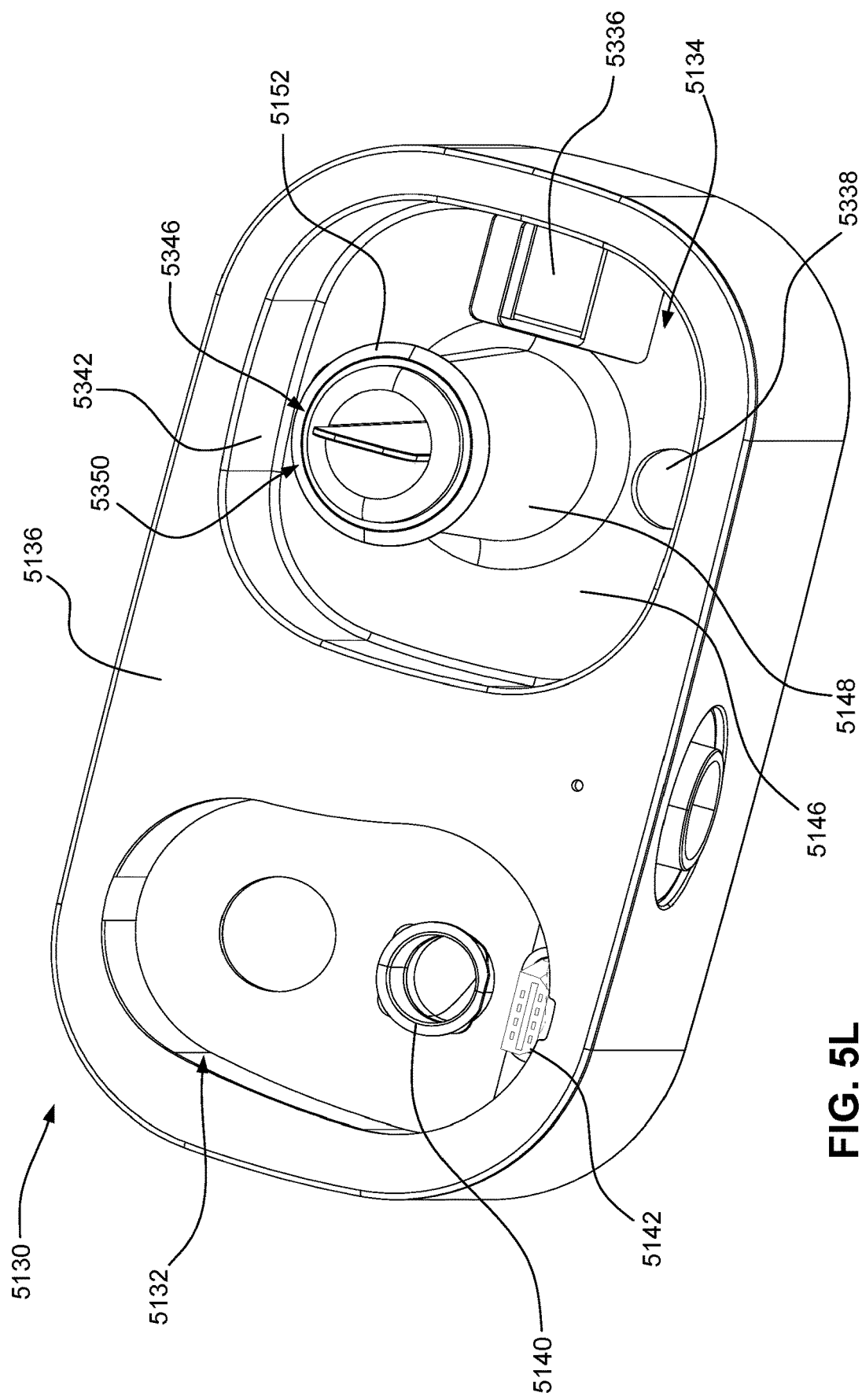
FIG. 5L shows a top perspective view of the humidifier base of FIG. 5D, with the RPT device and the water reservoir removed.
Figure 5M:
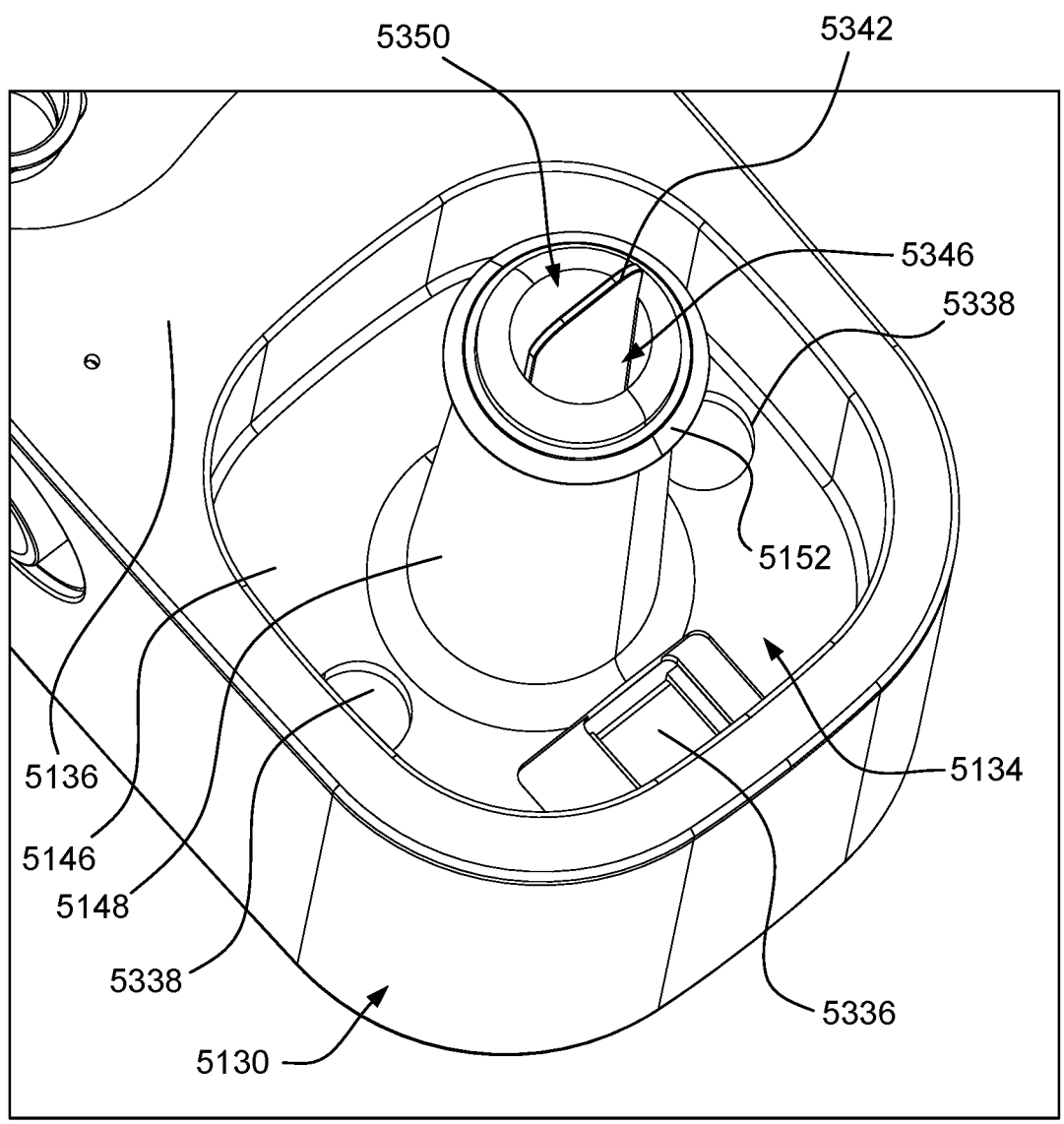
FIG. 5M shows an enlarged top perspective view of the humidifier-receiving portion of the humidifier base of FIG. 5L.
Figure 5N:
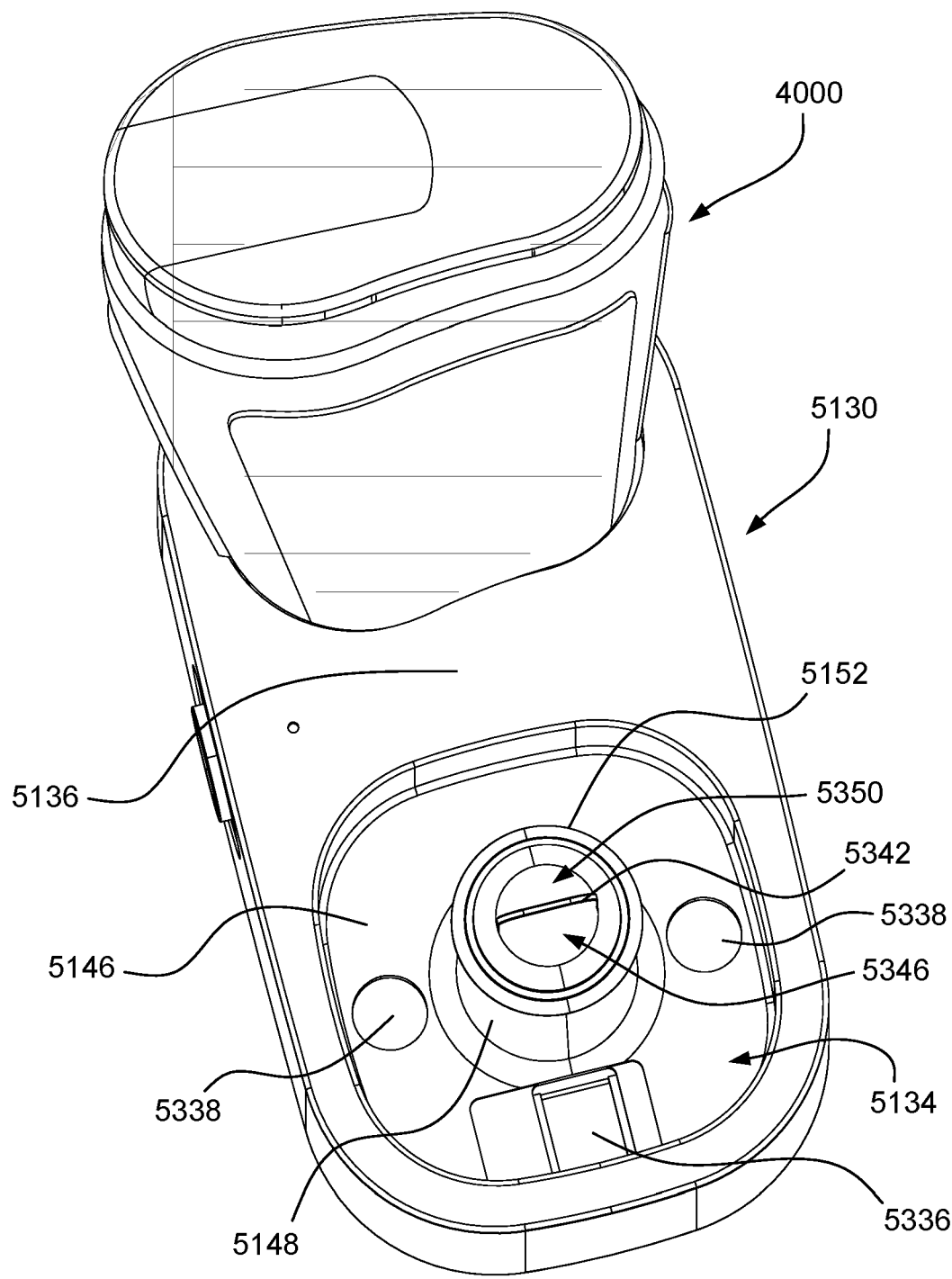
FIG. 5N shows an alternative top perspective view of the humidifier base of FIG. 5L, with the water reservoir removed, but the RPT device engaged with the base.
Figure 5O:
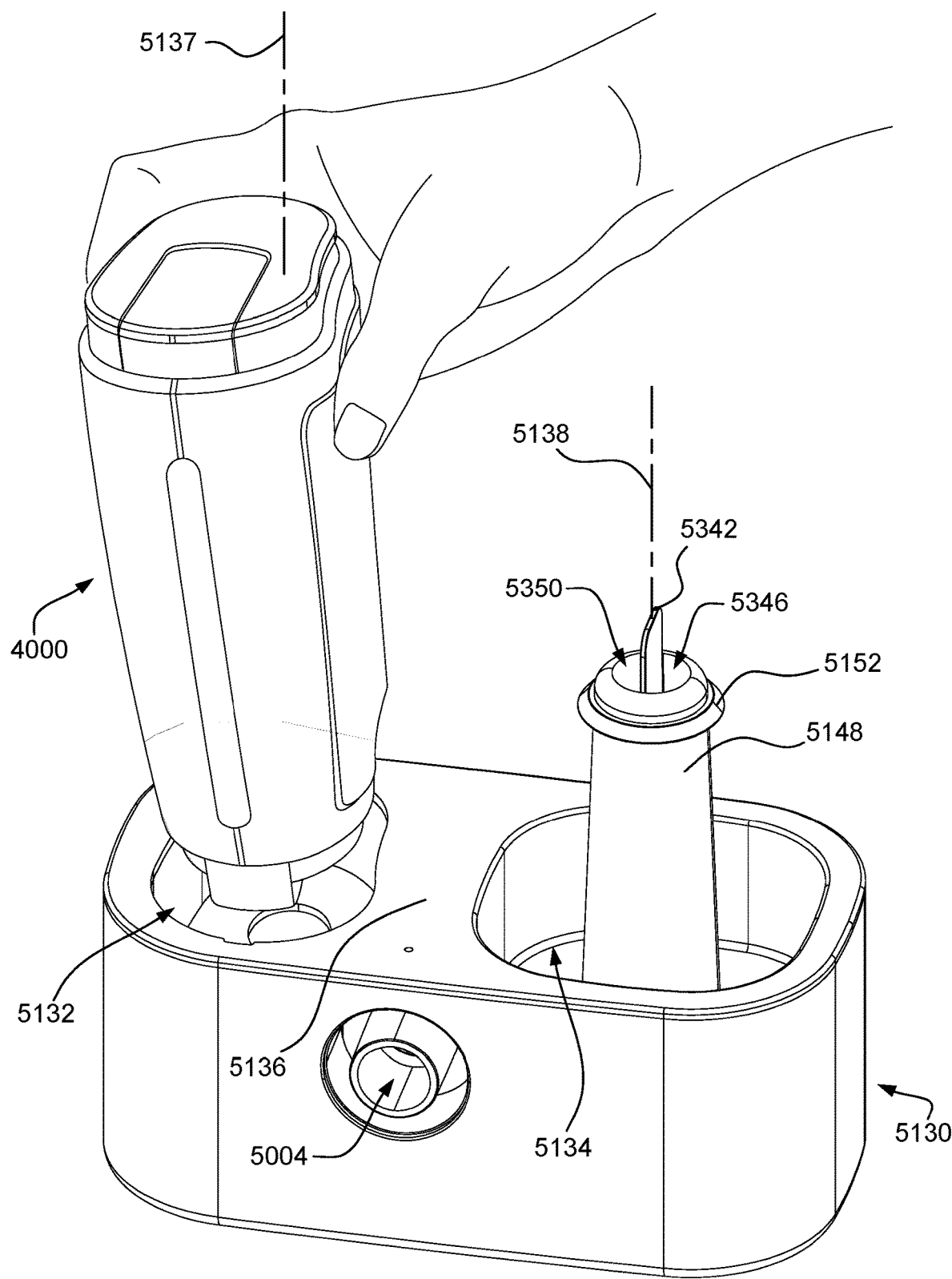
FIG. 5O shows a perspective view of the humidifier base of FIG. 5L, illustrating the RPT device being inserted into the humidifier base.
Figure 5P:
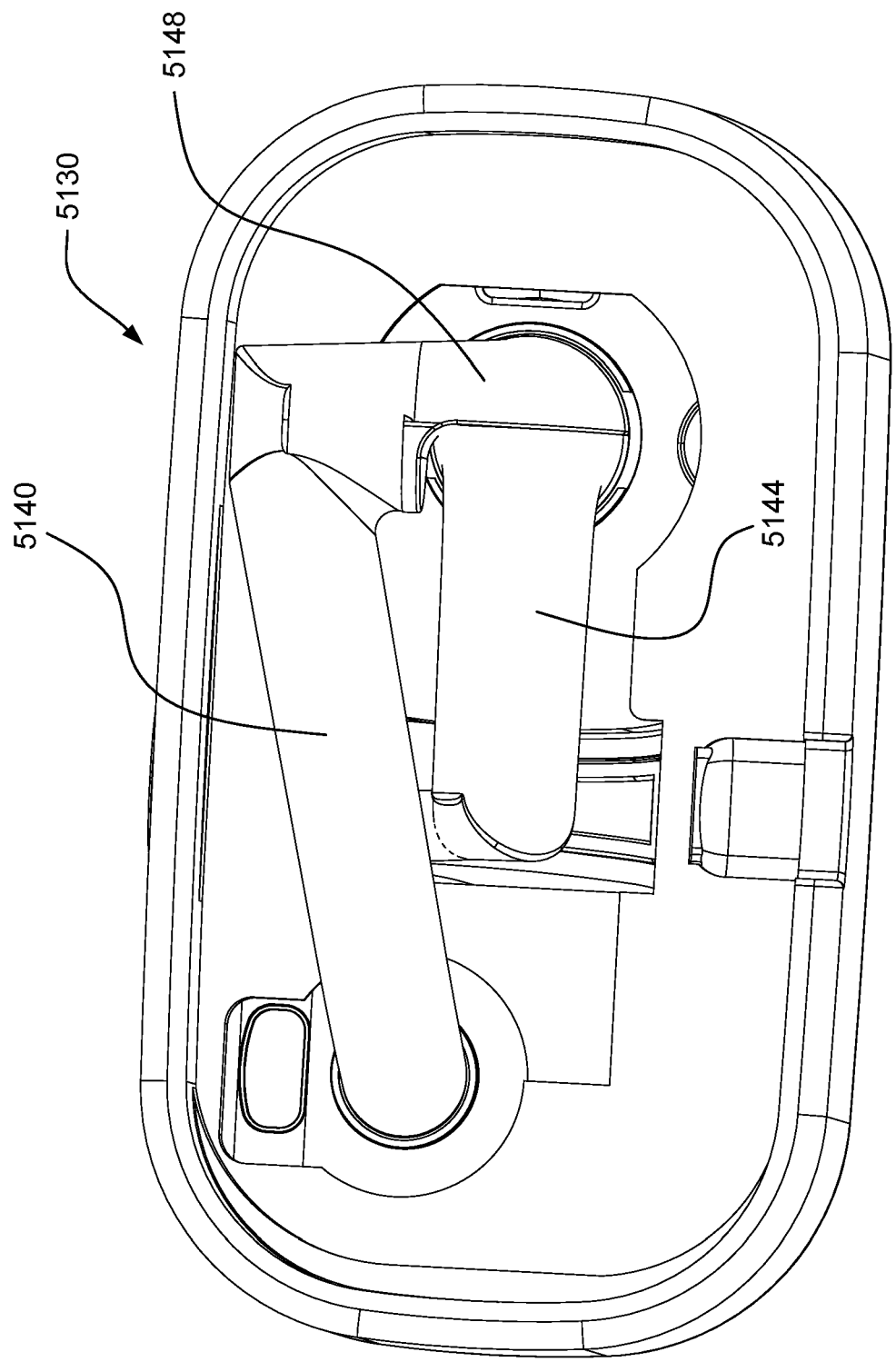
FIG. 5P shows a bottom perspective view of the humidifier base of FIG. 5L.
Figure 5Q:
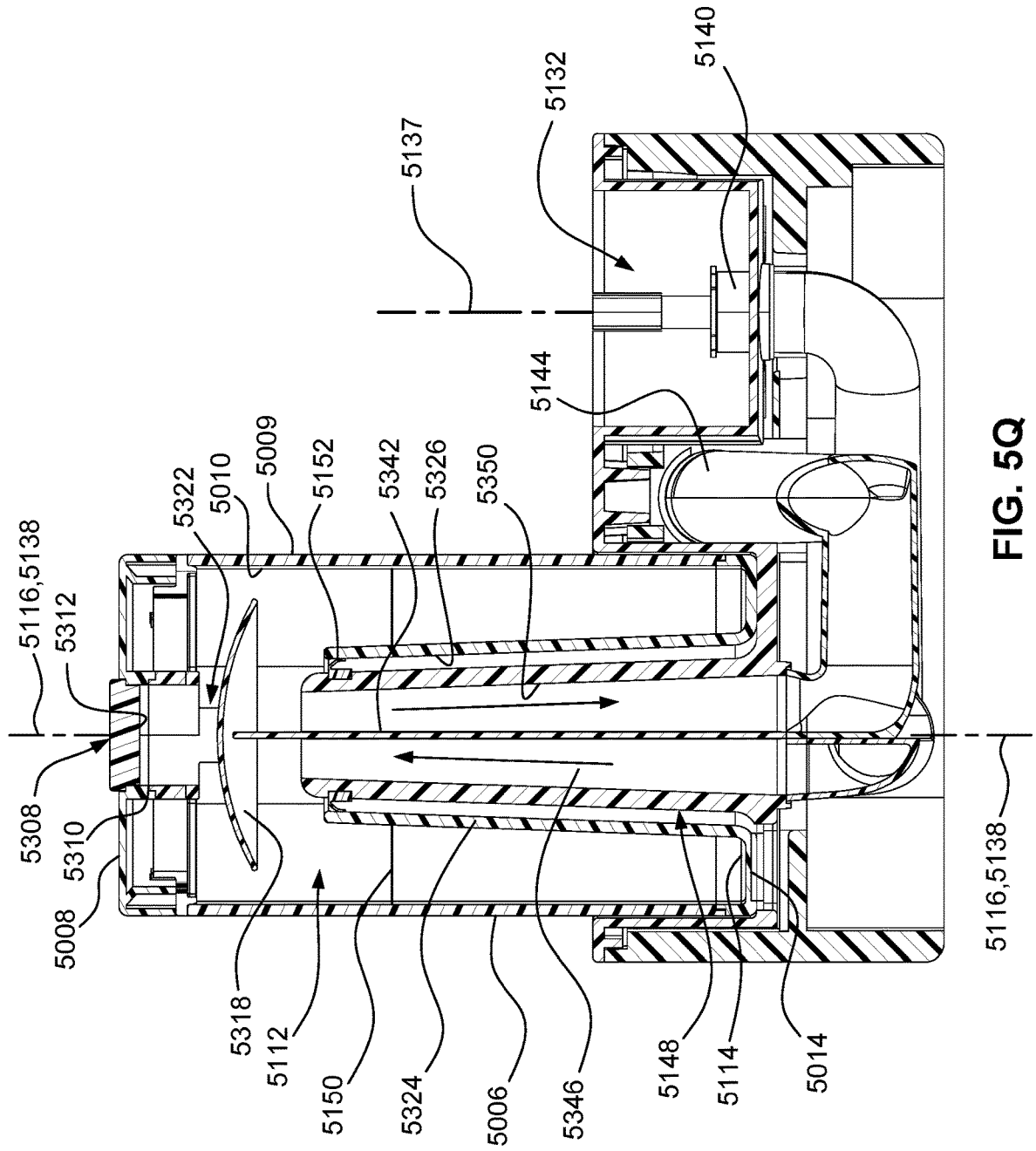
FIG. 5Q shows a front elevation cross-sectional view of the humidifier base of FIG. 5D, as well as the RPT device and the water reservoir engaged with the humidifier base.

As shown in FIGS. 5D-5Q, a humidifier 5000 may be designed not as a separate entity that engages with the RPT device, but in the form of a docking station, such as the humidifier reservoir dock 5130 that is configured to receive the RPT device 4000 and the water reservoir 5110. Such a configuration allows the water reservoir 5110 to be designed with an ergonomic shape and/or configuration, which may make the water reservoir 5110 easier to pick up, or otherwise handle.

In some forms, the ergonomic shape may allow a patient to comfortably pick up, or otherwise handle, the water reservoir 5110 with one hand. For example, the water reservoir 5110 may replicate a water bottle, or other portable water container, that a patient would routinely hold with one hand. The patient may be able to grasp the water reservoir 5110 so that is fits comfortably in one hand, and a second hand is not needed for carrying or supporting the water reservoir 5110.

The shape of the water reservoir 5110 may be rounded and include easy to grip dimensions. For example, the water reservoir 5110 may have a cylindrical shape or a rectangular prismatic shape (e.g., planar outer surfaces 5009 with rounded edges), which may be comfortably received within the patient's hand. This shape may fit comfortably within the patient's hand with limited or no discomfort (e.g., from jagged edges).

In one form, the water reservoir 5110 may have a rounded rectangular prism shape. In other words, at least some of the corners of the water reservoir 5110 may be rounded, while sides of the water reservoir 5110 may be planar (e.g., flat). The planar surfaces may provide the patient with easy to grip surfaces, while the rounded corners limit sharp edges from contacting the patient's hand and causing discomfort.

In certain forms, the water reservoir 5110 may be symmetric about at least one axis (e.g., a reservoir axis 5116). The symmetric shape may be easier for the patient to grasp in their hand, and hold for an extended period of time (e.g., while cleaning and/or refilling the water reservoir 5110).

Additionally, the width of the water reservoir 5110 may be less than the average patient's hand span (i.e., a distance measured from the tip of the patient's thumb to the tip of the patient's pinkie). Furthermore, the width of the water reservoir 5110 may be substantially less than the average patient's hand span, such as less than half of the average patient's hand span. The width may allow the patient to comfortably hold the water reservoir 5110 without straining their hand, or requiring their other hand to support the water reservoir 5110.

In some forms, the width of the water reservoir 5110 may be less than 25 cm. In some examples, the width of the water reservoir 5110 may be equal or less than 20 cm. In some examples, the width of the water reservoir 5110 may be equal or less than 15 cm. In some examples, the width of the water reservoir 5110 may be equal or less than 10 cm.

The ergonomic shape and the vertical orientation, as well as the vertical direction of insertion/extraction, of the water reservoir 5110 may be particularly useful for patients who suffer from ailments aside from respiratory disorders (e.g., like OSA). For example, patients may suffer from arthritis, which may make grasping the water reservoir 5110 difficult, and which may interfere with their ability to refill and/or clean the water reservoir 5110. By constructing the water reservoir 5110 with a small width as described above, patients suffering from an ailment may more easily handle the water reservoir 5110 independently (e.g., without assistance from a bed partner, a clinician, etc.), which may increase compliance (e.g., because the patient is less reliant on someone else).

The ergonomic shape may also permit a single sized water reservoir 5110 to be used by a variety of patients (e.g., one size fits most). In other words, hand span varies throughout different patients, as well as in different genders (e.g., women's average hand span may be less than men's average hand span). By designing the width of the water reservoir 5110 to be less than the average (e.g., less than the average woman's hand span), most patients will be able to grasp the water reservoir 5110 with a single hand.

As shown in FIGS. 5E to 5H, some forms of the humidifier 5000, water reservoir 5110 may include a humidifier reservoir base 5007 and a humidifier lid 5008, which selectively covers an opening to a reservoir cavity 5112 (see e.g., FIG. 5H) that may be configured to hold, or retain, the volume of liquid.

In some forms, the humidifier reservoir base 5007 includes an outer surface 5009 and an inner surface 5010 (or outer surfaces 5009 and inner surfaces 5010). The outer surface 5009 may be exposed to the ambient, and may be grasped by a patient. The inner surface 5010 may be opposite the outer surface 5009 across a thickness of the humidifier reservoir base 5007. The inner surface 5010 may at least partially form a boundary of the reservoir cavity 5112 (e.g., fluid within the reservoir cavity 5112 may directly contact the inner surface 5010).

In some forms, the humidifier lid 5008 may be removably coupled to the humidifier reservoir base 5007. The humidifier lid 5008 may be selectively movable between an open position, where at least a portion of the reservoir cavity 5112 is exposed, and a closed position, where the reservoir cavity 5112 is covered by the humidifier lid 5008.

In certain forms, the humidifier lid 5008 may be in the closed position when it is completely coupled to the humidifier reservoir base 5007. The humidifier lid 5008 may be in the open position when it is partially coupled to the humidifier reservoir base 5007 (e.g., not in a sealing engagement) and/or when the humidifier lid 5008 is completely removed from the humidifier reservoir base 5007.

In certain forms, the humidifier reservoir base 5007 may include a stepped surface 5300 proximate to an opening of the reservoir cavity 5112. Projections 5302 may extend over (e.g., substantially parallel to) the stepped surface 5300. The humidifier lid 5008 may include complimentary projections 5304 spaced along an inner surface, which are configured to selectively engage the projections 5302 of the humidifier reservoir base 5007, so that, upon rotation of the humidifier lid 5008, the lid is fastened to the humidifier reservoir base 5007.

In one form, the shape of the opening to the reservoir cavity 5112 is different than the shape of the outer perimeter of the humidifier reservoir base 5007. For example, as illustrated in FIGS. 5D to 5K, the opening to the reservoir cavity 5112 may be circular in order to more effectively facility relative rotation between the humidifier lid 5008 and the humidifier reservoir base 5007, while the outer perimeter may form a rounded rectangle. The humidifier lid 5008 may have a complementary shape to the humidifier reservoir base 5007 (e.g., the outer perimeter may be a rounded rectangle and the inner perimeter may be a circle). In other examples, the opening to the reservoir cavity 5112, the outer perimeter of the humidifier reservoir base 5007 and/or the humidifier lid 5008 may all have the same shape (circular, rounded rectangle etc.)

In certain forms, the humidifier reservoir base 5007 may be coupled to the humidifier lid 5008 in the closed position with a threaded engagement. In other forms, the humidifier reservoir base 5007 may be coupled to the humidifier lid 5008 in the closed position with a threaded engagement (although other types of engagements, like a bayonet engagement, may also be used). In other words, the projections 5304 of the humidifier lid 5008 may engage the projections 5302 of the humidifier reservoir base 5007, when the humidifier lid 5008 is rotated (e.g., clockwise) with respect to the humidifier reservoir base 5007. The projections 5302 may pull the humidifier lid 5008 (e.g., via the projections 5304) toward the humidifier reservoir base 5007, in order to selectively cover the reservoir cavity 5112.

In one form, the threaded engagement between the humidifier reservoir base 5007 and the humidifier lid 5008 may form a sealing engagement. In other words, in the closed position, a fluid-tight seal may exist between the humidifier reservoir base 5007 and the humidifier lid 5008 as a result of the engagement of the projections 5302, 5304. The fluid-tight seal may limit and/or prevent water from leaking out of the reservoir cavity 5112 (e.g., if the water reservoir 5110 is tilted or even turned upside down).

In one form, a seal (e.g., a thin (e.g. silicone) lip seal or an O-ring) may be disposed around a perimeter of the opening to the reservoir cavity 5112 and/or around an inner perimeter of the humidifier lid 5008. The seal may provide a fluid-tight engagement between the humidifier reservoir base 5007 and the humidifier lid 5008. The seal may also provide an additional form of sealing if the threaded engagement also forms a fluid-tight seal on its own.

In some forms, the patient may be able to disengage the humidifier lid 5008 from the humidifier reservoir base 5007 with a single hand. For example, the weight and/or stability of the humidifier reservoir base 5007 and the ease of engagement between the humidifier lid 5008 and the humidifier reservoir base 5007, may be such that patient may be able to twist the humidifier lid 5008 relative to the humidifier reservoir base 5007 and disengage projections 5302 and 5304, using a single hand—without the need to support the humidifier reservoir base 5007. The single hand operation may be further assisted by a non-circular transverse cross-sectional shape of the humidifier reservoir 5110, which prevents the humidifier reservoir 5110 from rotating within its dedicated humidification compartment 5134 during the opening of the lid. Such a single handed operation can be beneficial for patients who suffer from ailments, like arthritis, as one-handed opening may be easier and provide less discomfort (e.g., as compared to using both hands). Achieving the single-hand manipulation of the lid can at least partially be achieved by ensuring that the force required to decouple the humidifier lid 5008 from the humidifier reservoir base 5007 may be low so that the patient may not be required to strain in order to rotate and remove the humidifier lid 5008. Making the decoupling process easier and more comfortable (e.g., single-handed operation) may lead to an increased use of the RPT device and an improved compliance rate for some patients.

As shown in FIGS. 5E-FJ, some forms of the humidifier 5000 may include a plug or cap 5308, which may be removably coupled to the humidifier lid 5008 in order to selectively cover a water inlet opening 5310.

In some forms, the cap 5308 may be constructed from a resilient material. This may include rubber, synthetic rubber, or any similar material. The resilient material may allow the cap 5308 to seal against the water inlet opening 5310. For example, the cap 5308 may selectively limit or prevent the ingress and/or egress of fluids through the water inlet opening 5310. In other forms, the cap 5308 may be constructed from a stiffened, rigid, and/or semi-rigid material, which may be capable of sealing against the water inlet opening 5310. A combination between a more rigid material and a resilient material may also be used, with the resilient material being used to effect the seal with the opening of the humidifier lid 5008.

As best shown in FIG. 5I, in some forms, the cap 5308 may have a lower portion 5312 and a body 5314. The lower portion 5312 may extend away from the body 5314, and include a shape that substantially corresponds to the shape of the water inlet opening 5310 (e.g., substantially cylindrical).

In certain forms, the cap 5308 may also include a user engagement portion 5316, which may be an extension of the body 5314. For example, the body 5314 and the user engagement portion 5316 may be formed within the same plane, while the lower portion 5312 extends away from the body 5314 in a direction substantially perpendicular to that plane. The body 5314 and the user engagement portion 5316 may together form a "teardrop" shape. In other words, the body 5314 may have a substantially circular shape, and the user engagement portion 5316 may have a substantially triangular shape, which may be merged with the substantially circular shape.

In certain forms, the cap 5308 may seal with the water inlet opening 5310 via a press fit, a friction fit, and/or a snap fit. For example, the lower portion 5312 may be slightly wider (e.g., have a greater diameter) than the water inlet opening 5310.

In one form, the resilient material may deform in order to fit within the smaller diameter of the water inlet opening 5310. Once inside, the lower portion 5312 may at least partially expand to its original shape. The expanding material may contact the inner surface 5010 of the water inlet opening 5310 and create a seal that may limit fluids from exiting and/or entering the reservoir cavity 5112 though the water inlet opening 5310.

In one form, the wider diameter of the lower portion 5312 may be removably positioned around the outside of the water inlet opening 5310. For example, the resilient material of the lower portion 5312 may deform and expand in order to fit outside of the water inlet opening 5310. The resilient material may attempt to contract around the water inlet opening 5310, and create a seal that may limit fluids from exiting and/or entering the reservoir cavity 5112 though the water inlet opening 5310.

As shown in FIG. 5I, the cap 5308 may be removed with one hand. Additionally, the cap 5308 may be structured and configured so that a significant force may not be required in order to remove the cap 5308 from the humidifier lid 5008, and expose the water inlet opening 5310. As described above, this may be helpful for patients who have arthritis, or any other similar ailment.

In some forms, the patient may grasp the cap 5308 by the user engagement portion 5316, which may be a free and/or otherwise configured for handling (i.e. enlarged and/or spaced apart from a surface of the humidifier lid 5008) end of the cap 5308. This may allow a patient to grasp their fingers around the user engagement portion 5316 and pull the cap 5308 free from the humidifier lid 5008 without sufficient difficulty. Additionally, the user engagement portion 5316 may be constructed from a resilient material (e.g., along with the remainder of the cap 5308), which may permit the patient to bend the user engagement portion 5316 as they grasp the cap 5308. This may provide additional leverage, and make removal of the cap 5308 easier for the patient.

As shown in FIG. 5J, once the cap 5308 is removed, the patient may add more water (or other liquid) to the water reservoir 5110 through the water inlet opening 5310. The diameter of the water inlet opening 5310 may be sufficiently large in order to permit the patient to easily pour, or otherwise add, liquid through the water inlet opening 5310.

In some forms, the water inlet opening 5310 may have a diameter of at least about 1 cm. In some forms, the water inlet opening 5310 may have a diameter of at least about 2 cm. In some forms, the water inlet opening 5310 may have a diameter of at least about 3 cm. In some forms, the water inlet opening 5310 may have a diameter of at least about 4 cm. In some forms, the water inlet opening 5310 may have a diameter of at least about 5 cm.

In the above described example, the water inlet opening 5310 permits the patient to fill the water reservoir 5110 in situ—without having to remove the humidifier lid 5008 from the humidifier reservoir base 5007. Removing the cap 5308 from the humidifier lid 5008 may be easier and/or faster than removing the humidifier lid 5008 from the humidifier reservoir base 5007 (e.g., the patient may not need to disengage and reengage the water reservoir 5110 to the reservoir dock 5130). This may therefore make refilling the water reservoir 5110 easier for a patient.

As shown in FIGS. 5F-5H, the humidifier lid 5008 may further include a shroud 5318. As will explained later in the text, the shroud 5318 assists the operation of the humidification platform by redirecting the airflow, whilst at the same time shields the inlet/outlet conduit partitions 5346 and 5350 (FIG. 5O) from water poured through water inlet opening 5310, thus allowing the reservoir 5110 to be filled without removing it from the dock.

In some forms, the shroud 5318 includes a perimeter with a shape complimentary to the shape of the opening to the reservoir cavity 5112. For example, an outer perimeter of the shroud 5318 may be substantially circular.

In some forms, the humidifier lid 5008 may include an upper portion 5320 that the patient may grasp in order to rotate the humidifier lid 5008. The shroud 5318 may be spaced apart from the upper portion 5320. For example, when the humidifier lid 5008 is coupled to the humidifier reservoir base 5007, the shroud 5318 may be offset from the upper portion 5320 in the inferior direction. In other words, the shroud 5318 may be disposed within the reservoir cavity 5112 when the humidifier lid 5008 is coupled to the humidifier reservoir base 5007 (e.g., in the closed position).

In some forms, the shroud 5318 may have a curvature. For example, the shroud 5318 may have a domed shape curvature. As shown in FIGS. 5F and 5G, the shroud 5318 may have a positively domed curvature, so that when positioned within the reservoir cavity 5112, the shroud 5318 has a positively domed curvature with respect to the humidifier reservoir base 5007 (i.e., it has a concave surface facing the humidifier reservoir base 5007) and a negatively domed curvature with respect to the upper portion 5320.

In certain forms, the shroud 5318 may have a uniform curvature across its surface area. For example, the shroud 5318 may be symmetric about multiple axes (e.g. if the shroud is part of a spherical surface).

In some forms, the shroud 5318 may be coupled to a wall of the water inlet opening 5310. One end of the wall of the water inlet opening 5310 may be coupled to the upper portion 5320, and the other end may be coupled to the shroud 5318, thereby spacing the shroud 5318 apart from the upper portion 5320 (e.g., by the length of the water inlet opening 5310). As shown in FIGS. 5G and 5Q, the water inlet opening 5310 may form a passage that extends through a thickness of the humidifier lid 5008, so that water inlet opening 5310 may include a distinct inlet and outlet separated by the length of the passage (e.g., the thickness of the humidifier lid 5008).

In some forms, the shroud 5318 may define a surface configured to block liquid poured into the water inlet opening 5310 from directly entering the humidifier reservoir base 5007. As illustrated in FIG. 5G, the outlet 5322 may be disposed adjacent to the shroud 5318 (e.g., at an apex of the curvature of the shroud 5318). The shroud 5318 may engage with the water inlet opening 5310, so as to form an outlet 5322. The outlet 5322 including a circumferential opening that may extend around at least a portion of the perimeter of the water inlet opening 5310, with at least a portion of the upper boundary of the outlet 5322 being defined by the wall of the water inlet opening 5310, whilst at least a portion of the lower boundary of the outlet 5322 is defined by the upper surface of shroud 5318. Fluid may exit the outlet 5322 in a direction substantially perpendicular to the direction that the fluid enters the water inlet opening 5310.

In some forms, the humidifier lid 5008 may be constructed from a thin membrane with a substantially small thickness. The water inlet opening 5310 may not include a passageway (e.g., as described above and shown in FIGS. 5G and 5Q), and instead may include a single opening, which serves as both an inlet and an outlet for the humidifier lid 5008 (e.g., the inlet is not discernible from the outlet because of the substantially small thickness of the humidifier lid 5008). The water inlet opening 5310 may not include a wall since it includes a substantially small thickness, so the shroud 5318 may be coupled to another region of the humidifier lid 5008.

In some forms, the convex curvature of the shroud 5318 may direct the fluid exiting the outlet 5322 downwardly toward the bottom of the humidifier reservoir base 5007. Therefore, the curvature may assist gravity in directing the fluid into the humidifier reservoir base 5007. Additionally, the shroud 5318 may direct the fluid radially away from a reservoir axis 5116 of the reservoir 5110 toward the outer surface 5009 (also referred to as a side wall or a side surface) of humidifier reservoir base 5007 (e.g., toward the planar outer side surfaces 5009).

As shown in FIG. 5H, the reservoir cavity 5112 of the reservoir 5110 may include a generally open volume of space. For example, the outermost boundary of the reservoir cavity 5112 may extend to the inner surfaces 5010 of the humidifier reservoir base 5007.

In some forms, a column 5324 may be disposed within the reservoir cavity 5112. The column 5324 may extend at least partially along the height of the humidifier reservoir base 5007 along the superior-inferior direction, when the humidifier 5000 is in use.

In some forms, the column 5324 may be disposed concentrically and extend along the reservoir axis 5116 of the reservoir cavity 5112.

In some forms, the column 5324 may have a generally symmetrical shape. For example, the column 5324 may have a cylindrical shape, or a frustoconical shape. The reservoir cavity 5112 as a whole may also have a generally symmetrical shape.

In some forms, the column 5324 may be hollow and include a passageway 5326. The shape of the passageway 5326 may be substantially the same as the shape of the column 5324. In other words, the outer surface and the inner surface of the column 5324 may be substantially the same shape.

In certain forms, the diameter of the passageway 5326 may be substantially equivalent to the diameter of the water inlet opening 5310. The apex of the shroud 5318 may also be concentric with the center of the passageway 5326, so that the shroud 5318 may be symmetric about the passageway 5326.

In certain forms, the shroud 5318 may be wider than the diameter of at least the outlet opening of the passageway 5326 (see e.g., FIG. 5Q) that faces the shroud 5318, when in use. In examples where the shroud 5318 and the passageway 5326 are concentric, outer edges of the shroud 5318 may extend entirely beyond the passageway 5326. Liquid exiting the outlet 5322 may be directed by the shroud 5318 to flow outside of the passageway 5326. In other words, the shroud 5318 may limit liquid from flowing into the passageway 5326, and may instead direct the liquid to flow into the space of the reservoir cavity 5112 that surrounds the column 5324.

In some forms, the passageway 5326 may be open on both ends. For example, both the inferior-most portion of the column 5324 and the superior-most portion of the column 5324 include an opening to the passageway 5326. The inferior-most opening to the passageway 5326 may extend through a bottom surface 5014 of the humidifier reservoir base 5007.

In certain forms, at least one of the inferior-most opening and the superior-most opening to the passageway 5326 includes rounded edges. For example, the inferior-most opening to the passageway 5326 may include rounded edges. In other words, an edge forming a transition between the bottom surface 5014 and the passageway 5326 may be rounded. In some example, this may provide a smooth surface and may assist with inserting an object into the passageway 5326.

In some forms, at least one retention feature 5330 may be located at the bottom surface 5014 of the humidifier reservoir base 5007. The at least one retention feature 5330 may be a discrete element that is connected to the humidifier reservoir base 5007, or the at least one retention feature 5330 may be integrally formed with the humidifier reservoir base 5007. As shown in FIG. 5K, some forms of the humidifier reservoir base 5007 may include a pair of retention features 5330 (although any number of retention features 5330 may be used). In the illustrated example, the retention features 5330 are symmetrically spaced on the bottom surface 5014. For example, the retention features 5330 may be disposed on opposite sides of the passageway 5326 (e.g., approximately 180° apart). The retention features 5330 may be radially outside of the passageway 5326 in order to not obstruct or block the passageway 5326.

In some forms, the pair of retention features 5330 may be magnets, or constructed from a magnetic material. As will be discussed later in the text, the feature(s) 5330 may be used to lock, or otherwise removably secure, the humidifier reservoir base 5007 to the housing or humidifier reservoir dock 5130.

5.6.2.2 Conductive Portion

According to one arrangement, the reservoir 5110 may comprise a thermally conductive portion 5120 configured to allow efficient transfer of heat from an external heating element 5240 to the volume of liquid in the reservoir 5110. In one form, the conductive portion 5120 may be arranged as a plate, although other shapes may also be suitable. All or a part of the conductive portion 5120 may be made of a thermally conductive material such as aluminium (e.g. approximately 2 mm thick, such as about 1 mm, about 1.5 mm, about 2.5 mm or about 3 mm), another heat conducting metal or some plastics. In some cases, suitable heat conductivity may be achieved with less conductive materials of suitable geometry.

In some forms, the water reservoir 5110 may not include a conductive portion heated by way of an external heated element. Instead, the heating element 5240 may be coupled internally to the water reservoir 5110. Specifically, the base or the wall of humidifier reservoir base 5007 of the water reservoir 5110 may include the heating element 5240 so that the liquid in the water reservoir 5110 may be directly heated by the humidifier reservoir base 5007. In one example, the heating element 5240 may include a heated wire integrated into, or a printed circuit board (PCB) in-moulded into, an inner surface (a bottom surface 5014 or an outer side surface 5009) of the humidifier reservoir base 5007.

For that purpose, the water reservoir 5110 may include an electrically conductive portion 5334 that may be electrically connected to the heated element and that can be arranged to, upon engagement of the water reservoir 5110 with the humidifier reservoir dock 5130, electrically connect with a corresponding electrically conductive portion 5336 of the humidifier reservoir dock 5130. Connection between these conductive portions 5334, 5336 may provide power to the heating element 5240. The connection may also be used for transmitting signals from any sensors within the water reservoir 5110 to a controller located at the humidifier reservoir dock 5130. In some instances, the sensor signals can be passed on further from the humidifier reservoir dock 5130 and onto the RPT device 4000.

As shown in FIG. 5K, some forms of the water reservoir 5110 may include the electrically conductive portion 5334 on a bottom surface 5014 of the humidifier reservoir base 5007. Wires may extend through the material of base 5007, between the heating element 5240 and the electrically conductive portion 5334. In other forms, the electrically conductive portion 5334 may be disposed on another surface (e.g., an outer side surface 5009) of the humidifier reservoir base 5007.

In some forms, the electrically conductive portion 5334 may extend around a portion of the perimeter of the humidifier reservoir base 5007. In other words, the electrically conductive portion 5334 may be asymmetrically disposed on the humidifier reservoir base 5007.

In certain forms, the electrically conductive portion 5334 may be used in order to assist with positioning the water reservoir 5110 in the humidifier reservoir dock 5130. For example, the asymmetrical positioning of the electrically conductive portion 5334 means that there may be only one orientation of the water reservoir 5110 relative to the humidifier reservoir dock 5130 that will complete an electrical connection. This may assist the patient in properly orienting the water reservoir 5110, which may be otherwise symmetrical and/or difficult to otherwise distinguish its proper orientation (e.g., in the dark).

In some forms, the electrically conductive portion 5334 may be spaced apart from the retention features 5330 of the humidification reservoir 5110. In the illustrated example, the electrically conductive portion 5334 may be approximately 90° apart from each of the first retention features 5330.

In certain forms, the electrically conductive portion 5334 may include an electrical pad arranged so that the electrically conductive portion 5336 may connect to the electrically conductive portion 5334, while the retention features 5330 of the humidification reservoir 5110 are engaged (e.g. the electrical pad may extend a similar distance from the bottom surface 5014 as the retention features 5330).

5.6.2.3 Humidifier Reservoir Dock

In some forms, the humidifier 5000 may comprise a humidifier reservoir dock 5130 (see e.g., FIGS. 5B and 5L) configured to receive the humidifier reservoir 5110.

In some arrangements (see e.g., FIG. 5B), the humidifier reservoir dock 5130 may comprise a locking feature such as a locking lever 5135 configured to retain the reservoir 5110 in the humidifier reservoir dock 5130. The locking lever 5135 may be exposed while humidifier reservoir dock 5130 receives the humidifier reservoir 5110. The locking lever 5135 may limit the humidifier reservoir 5110 from moving out of the humidifier reservoir dock 5130 in the superior and/or lateral (e.g., left/right) directions. A user may actuate the locking lever 5135 (e.g., by pressing in the inferior direction) in order to enable movement of the humidifier reservoir 5110 out of the humidifier reservoir dock 5130. The locking lever 5135 may be biased into a locked position (e.g., position that limits movement of the humidifier reservoir 5110), so the patient may require two hands in order to remove the humidifier reservoir 5110 (e.g., one to keep the locking lever 5135 in an unlocked position and one to remove the humidifier reservoir 5110).

In some forms, as best shown in FIG. 5L, the humidifier reservoir dock 5130 may include a first compartment or device compartment 5132 and a second compartment or humidification compartment 5134. The device compartment 5132 and the humidification compartment 5134 may be spaced apart and/or isolated from one another by a central wall 5136. In the illustrated example, the device and humidification compartments 5132, 5134 are completely formed within the humidifier reservoir dock 5130. In other words, the entire perimeter of each compartment 5132, 5134 is entirely within the volume of the humidifier reservoir dock 5130. The device and humidification compartments 5132, 5134 may be at least partially recessed within the humidifier reservoir dock 5130 (e.g., a bottom surface of each compartment 5132, 5134 is more inferior than the central wall 5136). When inserted into the respective compartment 5132, 5134, both the RPT device 4000 and the humidifier reservoir 5110 are at least partially exposed (e.g., having at least part of a surface not within the respective compartment 5132, 5134 and covered by the humidifier reservoir dock 5130). In other words, a length of the RPT device 4000 and/or a length of the humidifier reservoir 5110 may be greater than a depth of the respective compartment 5132, 5134. This may assist with removal of the RPT device 4000 and/or the reservoir 51100 since a surface is always exposed for the patient to grab (e.g., with one hand).

The RPT device 4000 may have a length that extends substantially parallel to an RPT insertion axis 5137 for positioning the RPT device 4000 into the device compartment 5132 (see e.g., FIG. 5O). Both the RPT insertion axis 5137 and the RPT device 4000 are vertically oriented when the humidifier reservoir dock system is in an operational configuration. Because of that, the length of the RPT device in this case may also be referred to as a "height". In some examples, between approximately 25% to approximately 90% of the length of the RPT device 4000 may be exposed when the RPT device 4000 is inserted into the device compartment 5132. In some examples, between approximately 40% to approximately 80% of the length of the RPT device 4000 may be exposed when the RPT device 4000 is inserted into the device compartment 5132. In some examples, between approximately 50% to approximately 75% of the length of the RPT device 4000 may be exposed when the RPT device 4000 is inserted into the device compartment 5132. In some examples, approximately 66% of the length of the RPT device 4000 may be exposed when the RPT device 4000 is inserted into the device compartment 5132.

The humidifier reservoir 5110 may have a length (also height) that in operational configuration also extends vertically and parallel to a reservoir insertion axis 5138 for positioning the humidifier reservoir 5110 into the humidification compartment 5134. In some examples, between approximately 25% to approximately 90% of the length of the humidifier reservoir 5110 may be exposed when the humidifier reservoir 5110 is inserted into the humidification compartment 5134. In some examples, between approximately 40% to approximately 80% of the length of the humidifier reservoir 5110 may be exposed when the humidifier reservoir 5110 is inserted into the humidification compartment 5134. In some examples, between approximately 50% to approximately 75% of the length of the humidifier reservoir 5110 may be exposed when the humidifier reservoir 5110 is inserted into the humidification compartment 5134. In some examples, approximately 66% of the length of the humidifier reservoir 5110 may be exposed when the humidifier reservoir 5110 is inserted into the humidification compartment 5134.

In some forms, the device compartment 5132 and the humidification compartment 5134 have different shapes. For example, the device compartment 5132 may include a substantially elliptical opening, and the humidification compartment 5134 may include a substantially rectangular opening. The shapes of both compartments 5132, 5134 may have rounded corners. The different shapes may assist a patient in properly identifying each compartment 5132, 5134 (e.g., in the dark). In some forms, the device compartment 5132 and the humidification compartment 5134 may also have different depths.

5.6.2.3.1 Device Compartment

In some forms, the shape (e.g., elliptical) of the device compartment 5132 may be asymmetrical. For example, the elliptical shape may have a larger radius on one side than on the other side. This may assist a patient in properly identifying a particular side of the device compartment 5132.

In some forms, the RPT device 4000 may be removably positioned within the device compartment 5132. As described above, the RPT device 4000 may be operable without the humidifier 5000. In other words, the RPT device 4000 may deliver a flow of pressurized breathable gas to a patient without being positioned within the device compartment 5132 (or otherwise connected to the humidifier reservoir dock 5130). However, the RPT device 4000 may be disposed within the device compartment if a clinician prescribes or a patient desires a humidifier flow of pressurized breathable gas.

In some forms, the device compartment 5132 may include an opening to a first fluid conduit 5140. The opening to the first fluid conduit 5140 may be disposed in a position that corresponds to an outlet on the RPT device (e.g. proximate to the outlet air filter 4114). In other words, the first fluid conduit 5140 may or may not be centered in the device compartment 5132, in order to align with the outlet of the RPT device 4000.

In some forms, the first fluid conduit 5140 may receive a flow of pressurized air from the RPT device 4000. For example, the first fluid conduit 5140 may receive dry, un-humidified air from the RPT device 4000.

In some forms (see e.g., FIG. 5P), the first fluid conduit 5140 may extend toward the humidification compartment 5134, and may convey the flow of dry, un-humidified air to the humidification compartment 5134. The first fluid conduit 5140 may fluidly connect the device and humidification compartments 5132, 5134 to one another.

In some forms, the RPT device 4000 may be portable and run on a battery (e.g., a rechargeable battery). The device compartment 5132 may include a charging connector 5142 that may connect with the RPT device 4000 when the RPT device 4000 is positioned within the device compartment 5132. The charging connector 5142 may provide electrical power in order to recharge the battery of the RPT device 4000 and/or power the motor of the RPT device 4000. The opening of the first fluid conduit 5140 and the charging connector 5142 may be so arranged that, upon insertion of the RPT device 4000 into the device compartment 5132, the air outlet of the RPT device 4000 may engage pneumatically the opening of the first fluid conduit 5140 substantially simultaneously to the electromechanical engagement of the charging connector 5142 with a respective electrical connector of the RPT device 4000. Alternatively, the pneumatic and the electromechanical engagements may be effected sequentially. The charging connector 5142 may also assist in supporting the RPT device 4000 within the device compartment 5132 in a proper orientation (e.g., so that the outlet of the RPT device 4000 is aligned with the opening to the first fluid conduit 5140). Thus, in addition to the shape of the device compartment 5132 and the location of the of the opening to the first fluid conduit 5140, the charging connector 5142 may provide yet further guidance to the user as to the proper alignment and orientation of the RPT device 4000, when inserted into the device compartment 5132. Specific alignment/guiding marks may also be provided on both the device compartment 5132 and the RPT device 4000.

In some forms, the RPT device 4000 may be inserted and/or removed from the device compartment 5132 using a single hand (see e.g., FIG. 5O). A retention force between the RPT device 4000 and the device compartment 5132 (e.g., via the charging connector 5142) may be small, so that a patient using a single hand may engage/disengage the RPT device 4000 from the device compartment 5132. This may assist patients, with ailments like arthritis, in more easily removing and/or handling the RPT device 4000. Additionally, as discussed earlier in the text, the depth of the device compartment 5132 is shallower than a height of the RPT device 4000 (see e.g., FIG. 5D), so that a section of RPT device 4000 is exposed from the device compartment 5132, allowing it to be conveniently grasped by a patient.

In addition, whilst the partial insertion and the electromechanical engagement between the electrical contacts do provide mechanical support for the RPT device when inserted within the device compartment 5132, the device compartment 5132 may comprise further mechanical features to support the engaged RPT device, such as groove and tongue engagement features, locking clips etc.

5.6.2.3.2 Humidification Compartment

In some forms, the shape (e.g., substantially rectangular) of the humidification compartment 5134 may be symmetrical. For example, the humidification compartment 5134 may have a circular or substantially squared shape. Even when square-shaped, the humidification compartment 5134 may still have rounded corners. The shape of the humidification compartment 5134 may therefore be symmetrical about multiple (e.g., four) axes.

In some forms, the humidifier reservoir 5110 may be removably positioned within the humidification compartment 5134, which may have a complimentary (e.g. substantially the same) shape as the humidification compartment 5134. Since the device compartment 5132 has a different shape than the humidification compartment 5134, the patient may be prevented from improperly inserting the humidifier reservoir 5110 into the device compartment 5132. The humidifier reservoir 5110 may be supported in the humidification compartment (e.g., in an upright (vertical) orientation) in order to limit liquid in the reservoir cavity 5112 from spilling (e.g., if the humidifier lid 5008 and/or the cap 5308 are not properly sealed).

In some forms, the humidification compartment 5134 may include at least one retention feature 5338 that may be located at the lower surface 5146 (e.g., a recessed surface) of the humidification compartment 5134. The retention feature(s) 5338 may engage corresponding retention feature 5330 to lock, or otherwise removably secure, the humidifier reservoir base 5007 within humidifier reservoir dock 5130.

In some forms, the humidification compartment 5134 includes a pair of retention features 5338 (although any number of retention features 5338 may be used). In the illustrated example, the two retention features 5338 can be symmetrically spaced on the lower surface 5146. For example, the retention features 5338 of the humidification compartment 5134 may be disposed on opposite sides of the lower surface 5146 (e.g., approximately 180° apart).

In some forms, both pairs of corresponding retention features 5330 and 5338 may be magnets, or constructed from a magnetic material. Each of the pair of retention magnetic features 5338 may have an opposite polarity to its respective engaging retention feature 5330, in order to facilitate the retention engagement. As far as the polarity of each retention features 5338 with respect to each other is concerned, they may be chosen to have an opposite polarity to each other (e.g., one has a positive polarity and one has a negative polarity). In another form, all of the retention features 5338 have the same polarity (e.g., all positive or all negative).

In certain forms, the attributes of retention features 5330, 5338 of the humidification reservoir and the humidification compartment 5134, respectively, may be chosen so as to perform more than one functions. For example, the polarities of the retention features 5330, 5338 of the humidification reservoir 5110 and the humidification compartment 5134, respectively, may assist the patient in properly orienting the humidifier reservoir 5110 within the humidification compartment 5134. For example, the retention features 5330 can include at least one magnet with a positive polarity, and at least one magnet with a negative polarity. Similarly, the retention features 5338 may include at least one magnet with a positive polarity, and at least one magnet with a negative polarity. Thus, there may be limited orientations (e.g., only a single orientation) that the humidifier reservoir 5110 may be inserted into the humidification compartment 5134. For example, like polarities may repel one another, and the patient may feel the repulsion as a tactile response, which may alert them to the improper orientation. Additionally, the magnetic forces may pull the retention features 5330 toward the retention features 5338 of the humidification compartment of the opposite polarity, thereby guiding the patient toward the proper alignment. This may be especially useful when the patient is attempting to insert the humidifier reservoir 5110 into the humidification compartment 5134 in an environment with low visibility (e.g., in the dark). When the retention features 5330, 5338 are properly aligned, the patient may feel a tactile response of the humidifier reservoir 5110 being pulled toward the lower surface 5146 (e.g., via the magnetic attraction).

Additionally, if the patient orients the humidifier reservoir 5110 so that the retention features 5338 of the humidification compartment 5134 are aligned with neither of the retention features 5330 of the humidification reservoir 5110, the lack of a tactile response (e.g., neither magnetic repulsion nor magnetic attraction) may alert the patient that the humidifier reservoir 5110 needs to be rotated (e.g., either clockwise or counter-clockwise) in order to properly align the retention features 5330, 5338.

The aligning/guiding function of the magnetic retention features 5330 and 5338 can be extended even further if each of the humidifier reservoir 5110 and the humidification compartment 5134 have a larger number of magnets (e.g., four magnets). These magnets can be suitably aligned (e.g., four magnets may be aligned with the four side walls of the humidifier reservoir 5110). If only one of the magnetic retention features 5330 of the humidifier reservoir 5110 is of a different polarity (e.g., a positive polarity), and only one magnetic retention feature 5338 of the opposite polarity (in this case—a negative polarity) is correspondingly located on the humidification compartment 5134 (e.g., and the remaining magnets there being positive), the arrangement would be such that it will allow engagement of the humidifier reservoir 5110 with the humidification compartment 5134 in only a single (e.g., correct) orientation. In this case, it can be said that the magnets have not only a locking, but also a guiding function.

The aligning/guiding function can be extended yet further by locating the magnetic retention feature 5338 not at the bottom, as shown in FIG. 5L, but around the top opening of the compartment 5134, not shown. In this way the magnetic retention feature 5338 will be close to the bottom of the humidifier reservoir 5110 at the time of the initial engagement between the humidifier reservoir 5110 with the humidification compartment 5134. This will allow the magnets of the two components to interact at a very early stage of engagement of the components and indicate to a user if this is the correct orientation of engagement. This may serve as a poke yoke feature preventing engagement in the wrong orientation of the humidifier reservoir 5110 with respect to the humidification compartment 5134. An alternative mechanically-based poke yoke feature (such as tongue and groove) or using a non-symmetrically shaped cross-section for the humidifier reservoir 5110, may be used instead.

Thus, the retention features 5330, 5338 also help with aligning the engagement between the humidifier reservoir 5110 and the humidification compartment 5134. On the other hand, if all of the retention features 5330 and/or 5338 have the same polarity (e.g., all positive or all negative), the tub may be placed in any orientation and still engage the magnets.

In some forms, the electrically conductive portion 5336 may be disposed on the lower surface 5146. The electrically conductive portion 5336 may be located between the pair of retention features 5338 (e.g., about 90° apart), at approximately the same spacing as between the electrically conductive portion 5334 and the retention features 5330. The electrically conductive portion 5336 may be oriented in alignment with the polarities of the retention features 5338 so that there may be only one orientation that the humidifier reservoir 5110 may be inserted into the humidification compartment 5134 to be properly mechanically coupled (e.g., via magnetic force) and electrically coupled (e.g., via contact between the conductive portions 5334, 5336).

In certain forms, the magnetic force between the retention features 5330, 5338 may be relatively low. For example, it may be relatively easy to disengage the humidifier reservoir 5110 from the humidification compartment 5134. This may assist patients with certain ailments (e.g., arthritis) in grasping and removing the humidifier reservoir 5110 with a single hand.

Instead of, or in addition to, being located at the bottom of the humidifier reservoir base 5007 and the humidification compartment 5134 (see e.g., FIG. 5L and its corresponding discussion in the text below), the retention features 5330 and 5338 may also be located on the respective outer side surfaces 5009 of the humidifier reservoir base 5007 and the humidification compartment 5134. Locating one or more retention features 5330 on one of more outer side surfaces 5009 closer to the stepped surface 5300 of the humidifier reservoir 5110 may provide a faster engagement.

The feature(s) 5330 and 5338 may, in addition or instead of being used as retention features, also be used to assist the user with positioning/orienting the humidifier reservoir 5110, when inserting the reservoir into the humidifier reservoir dock 5130. For that purpose, the feature(s) 5330 and 5338 may be disposed in an asymmetric orientation in order to limit the number of orientations that the humidifier reservoir 5110 may be properly inserted into the humidification compartment 5134, and be in an operational configuration. In some forms, there may be a single orientation of the humidifier reservoir 5110 that achieves the operational configuration. Additionally, locating one or more of the retention features 5330 on one of more outer side surfaces 5009 (as described above) may allow the retention feature(s) 5330 to be larger, and provide a stronger tactile feedback.

As shown in FIGS. 5O and 5P, the humidifier reservoir dock 5130 may include a second fluid conduit 5144 that extends between the humidification compartment 5134 and the humidifier outlet 5004. The first fluid conduit 5140 may thus convey dry air from the RPT device 4000 in the device compartment, to the humidification compartment 5134, and the second fluid conduit 5144 may convey humidifier air out of the humidification compartment 5134 and to the patient (i.e., via the humidifier outlet 5004).

As shown in FIGS. 5L to 5O, the humidification compartment 5134 may include a third fluid conduit 5148, which may extend upwardly (when in use) from the lower surface 5146 of the humidification compartment 5134. For example, the third fluid conduit 5148 may extend substantially perpendicular with respect to the lower surface 5146. In other words, the third fluid conduit 5148 may extend substantially along the superior-inferior direction when the humidifier 5000 is in use. Additionally, the top end of third fluid conduit 5148 may be the most superior, or one of the most superior, points on the humidifier reservoir dock 5130.

In some forms, the third fluid conduit 5148 may be disposed in a center of the humidification compartment 5134. In other words, the third fluid conduit 5148 may be concentric with the lower surface 5146 of the humidification compartment 5134.

In some forms, the third fluid conduit 5148 may have a generally symmetrical shape. For example, the third fluid conduit 5148 may have a cylindrical shape, or a frustoconical shape. The third fluid conduit 5148 may also have substantially the same outer shape as the column 5324 of the humidifier reservoir 5110.

In some forms, a sealing member 5152 may be positioned on an outer surface of the third fluid conduit 5148, to pneumatically seal the humidifier reservoir 5110, upon insertion. For example, the sealing member 5152 may be disposed proximate to a superior end of the third fluid conduit 5148. In the illustrated examples, the sealing member 5152 is a thin (e.g. silicone) lip seal, which requires low force to achieve seal. However, the sealing member may be in another form, such as an O-ring constructed from a resilient material. The sealing member 5152 may comprise a compression seal, whereby, upon insertion of the of the passageway 5326 over the third fluid conduit 5148, the two opposing walls may cause the sealing member 5152 to compress, thereby forming a pneumatic seal between the passageway 5326 and the third fluid conduit 5148. Alternatively, the sealing member 5152 may comprise a lip seal, whereby the seal comprises a relatively thin wall that is so arranged that the pressure inside the humidifier reservoir 5110 acts upon a surface of the wall to press further the wall into its sealing configuration and strengthen the seal.

In some forms, the sealing member may limit or prevent fluid flow (e.g., pressurized air) through the passageway 5326 when the third fluid conduit 5148 is inserted into the passageway 5326.

The upright configuration of the humidifier reservoir dock 5130 allows the removal of the conduits 5140 and 5148 from humidifier reservoir 5110 and including them into the base of the humidifier reservoir dock 5130 instead, where they are out of side. This may simplify the manufacturing of the humidifier reservoir 5110, reduce the number of seals used (compared to some prior art RPT devices), reduce the cost and improve the overall aesthetics of the entire system.

Upon inserting the humidifier reservoir 5110 into compartment 5134, a number of engagements take place, including; the full mechanical supporting engagement (related to the supporting engagement between the inner side wall of the humidification compartment 5134 with the outer surfaces 5009 of the humidifier reservoir 5110), a magnetic supporting engagement (effected by the engagement of magnetic retention portions 5330 and 5338), the pneumatic sealing engagement (at the sealing member 5152) and the electrical coupling between the conductive portion 5334 and 5336. At least two or more of these engagements may be effected substantially simultaneously. Alternatively, at least some of these engagements may happen sequentially—with one or more of these being effected at a different time than the rest.

In some forms, the third fluid conduit 5148 may include a divider 5342, which may be shaped as a substantially flat plate. The divider 5342 may extend along the entire length of the third fluid conduit 5148. In some examples, the divider 5342 may extend upwardly beyond the third fluid conduit 5148. In other words, the divider 5342 may extend more superior than an opening to the third fluid conduit 5148, and may be the most superior portion of the humidifier reservoir dock 5130, when in operational configuration.

In some forms, the divider 5342 may partition the third fluid conduit 5148 into a first or inlet portion 5346 and a second or outlet portion 5350. The inlet portion 5346 and the outlet portion 5350 may each be fluid conduits configured to convey a fluid.

In some forms, the divider 5342 may separate the inlet and outlet portions 5346, 5350 so that they are substantially isolated from one another. For example, fluid in the inlet portion 5346 may be isolated from fluid in the second portion 5350, so that fluid in either portion 5346, 5350 are limited from mixing within the third fluid conduit 5148.

In certain forms, the divider 5342 may partition the third fluid conduit 5148 so that each portion 5346, 5350 has substantially the same volume. In other words, the divider 5342 may be disposed in a center of the third fluid conduit 5148, and an opening to each portion 5346, 5350 is substantially semi-circular.

In some forms, the retention features 5338 may be radially outside of the third fluid conduit 5148, and do not obstruct or block the third fluid conduit 5148. Similarly, the electrically conductive portion 5336 may also be disposed radially outside of the third fluid conduit 5148.

As shown in FIGS. 5P and 5Q, the third fluid conduit 5148 may be in fluid communication with the first fluid conduit 5140 and the second fluid conduit 5144. For example, the fluid from the first fluid conduit 5140 may be conveyed into the inlet portion 5346, and fluid from the second portion 5350 may be conveyed to the second fluid conduit 5144. Thus, the inlet portion 5346 may convey fluid in the superior direction, and the second portion 5350 may convey fluid in the inferior direction.

5.6.2.4 Water Level Indicator

The humidifier reservoir 5110 may comprise a water level indicator 5150 as shown in FIG. 5A-5B. In some forms, the water level indicator 5150 may provide one or more indications to a user such as the patient 1000 or a care giver regarding a quantity of the volume of water in the humidifier reservoir 5110. The one or more indications provided by the water level indicator 5150 may include an indication of a maximum, predetermined volume of water, any portions thereof, such as 25%, 50% or 75% or volumes such as 200 ml, 300 ml or 400 ml.

In some forms, the water level indicator 5150 may be below the maximum height of the column 5324. In other words, when the humidifier reservoir 5110 is its operational vertical orientation, the water level indicator 5150 is inferior to the superior-most entry to the passageway 5326. This way, the maximum liquid level in the water reservoir 5110 will not cause the liquid to enter passageway 5326.

5.6.2.5 Humidifier Transducer(s)

The humidifier 5000 may comprise one or more humidifier transducers (sensors) 5210 instead of, or in addition to, transducers 4270 described above. Humidifier transducers 5210 may include one or more of an air pressure sensor or transducer 5212, an air flow rate transducer 5214, a temperature sensor 5216, or a humidity sensor 5218 as shown in FIG. 5C. A humidifier transducer 5210 may produce one or more output signals which may be communicated to a controller such as the central controller and/or the humidifier controller 5250. In some forms, a humidifier transducer may be located externally to the humidifier 5000 (such as in the air circuit 4170) while communicating the output signal to the controller.

5.6.2.5.1 Pressure Transducer

One or more pressure transducers 5212 may be provided to the humidifier 5000 in addition to, or instead of, a pressure sensor provided in the RPT device 4000.

5.6.2.5.2 Flow Rate Transducer

One or more flow rate transducers 5214 may be provided to the humidifier 5000 in addition to, or instead of, a flow rate sensor provided in the RPT device 4000.

5.6.2.5.3 Temperature Transducer

The humidifier 5000 may comprise one or more temperature transducers 5216. The one or more temperature transducers 5216 may be configured to measure one or more temperatures such as of the heating element 5240 and/or of the flow of air downstream of the humidifier outlet 5004. In some forms, the humidifier 5000 may further comprise a temperature sensor 5216 to detect the temperature of the ambient air.

5.6.2.5.4 Humidity Transducer

In one form, the humidifier 5000 may comprise one or more humidity sensors 5218 to detect a humidity of a gas, such as the ambient air. The humidity sensor 5218 may be placed towards the humidifier outlet 5004 in some forms to measure a humidity of the gas delivered from the humidifier 5000. The humidity sensor may be an absolute humidity sensor or a relative humidity sensor.

5.6.2.6 Heating Element

A heating element 5240 may be provided to the humidifier 5000 in some cases to provide a heat input to one or more of the volume of water in the humidifier reservoir 5110 and/or to the flow of air. The heating element 5240 may comprise a heat generating component such as an electrically resistive heating track. One suitable example of a heating element 5240 is a layered heating element such as one described in the PCT Patent Application Publication No. WO 2012/171072, which is incorporated herewith by reference in its entirety.

In some forms, the heating element 5240 may be provided in the humidifier reservoir base 5007 where heat may be provided to the humidifier reservoir 5110 primarily by conduction as shown in FIG. 5B.

As shown in FIG. 5H, some forms of the humidifier 5000 may include a heating element 5240 inside the water reservoir 5110, so that heat is provided directly to the fluid in the water reservoir 5110.

In some forms, the heating element 5240 is disposed within the humidifier reservoir base 5007, and may be coupled to a wall (e.g., an inner surface 5010, an inner bottom wall 5114 (FIG. 5Q), etc.) of the humidifier reservoir base 5007. For example, the heating element 5240 may be molded into a wall of the humidifier reservoir base 5007. The heating element 5240 may or may not be in direct contact with the fluid within the water reservoir 5110 (e.g., the heating element 5240 may be between the outer and inner surfaces 5009, 5010). The material used to construct the wall of the water reservoir 5110 may have a relatively high thermal conductivity in order to more efficiently conduct heat through the inner surface 5010 of the humidifier reservoir base 5007.

In some forms, the heating element 5240 may be coupled to the wall of the humidifier reservoir base 5007, and disposed within the water reservoir 5110. In other words, the heating element 5240 may be coupled (e.g., via overmolding, an adhesive, etc.) to an inner surface 5010 of the humidifier reservoir base 5007. Convective heat transfer may be the primary means of transferring heat from the heating element 5240 to the fluid in the water reservoir 5110. The humidifier reservoir base 5007 may be constructed from a material with a relatively low thermal conductivity (e.g., as compared to the example above) in order to increase the efficiency of the heating element 5240 (e.g., so that limited heat is lost through the humidifier reservoir base 5007 instead of convecting to the fluid).

In certain forms, the heating element 5240 may extend only around a portion of the perimeter of the humidifier reservoir base 5007 or be disposed at least partially around the passageway 5326 on the bottom surface 5014, in order to minimise any feelings of heat discomfort when a user is holding the water reservoir 5110. In examples where the humidifier reservoir base 5007 is constructed from a high thermal conductivity, positioning the heating element 5240 around only a portion of the perimeter may limit a section of the humidifier reservoir base 5007 from becoming too hot for the patient to touch.

In some forms, wires, flexible printed circuit (FPC) or other conductor arrangement may extend through a wall of the humidifier reservoir base 5007 in order to reach the electrically conductive portion 5334. The heating element 5240 can therefore be electrically connected to the electrically conductive portion 5334, and may receive electrical power when the electrically conductive portion 5334 contacts the electrically conductive portion 5336.

5.6.2.7 Humidifier Controller

According to one arrangement of the present technology, a humidifier 5000 may comprise a humidifier controller 5250 as shown in FIG. 5C. In one form, the humidifier controller 5250 may be a part of the central controller. In another form, the humidifier controller 5250 may be a separate controller, which may be in communication with the central controller.

In one form, the humidifier controller 5250 may receive as inputs measures of properties (such as temperature, humidity, pressure and/or flow rate), for example of the flow of air, the water in the reservoir 5110 and/or the humidifier 5000. The humidifier controller 5250 may also be configured to execute or implement humidifier algorithms and/or deliver one or more output signals.

As shown in FIG. 5C, the humidifier controller 5250 may comprise one or more controllers, such as a central humidifier controller 5251, a heated air circuit controller 5254 configured to control the temperature of a heated air circuit 4171 and/or a heating element controller 5252 configured to control the temperature of a heating element 5240.

5.6.2.8 Humidifier Operation

As described previously, the patient may insert the RPT device 4000 and the humidifier reservoir 5110 into their respective compartment 5132, 5134. Both the RPT device 4000 and the humidifier reservoir 5110 may be inserted using a single hand. In addition, the insertion axes 5137, 5138 for both the RPT device 4000 and the humidifier reservoir 5110 may be substantially parallel to each other and substantially vertically oriented (perpendicular to a horizontal plain on which the humidifier reservoir dock 5130 is located in its operational configuration).

In some forms, the humidifier reservoir 5110 may be inserted into the humidification compartment 5134 by inserting the third fluid conduit 5148 into inferior opening of the passageway 5326. The passageway 5326 may have a larger diameter than the third fluid conduit 5148, and the curved edges of the passageway 5326 may assist the passageway 5326 in receiving the third fluid conduit 5148.

In some forms, the frustoconical shape of the passageway 5326 may cause the narrowing of the passageway 5326 in the superior direction. The narrowing diameter of the passageway 5326 may cause the sealing member 5152 to frictionally engage the inner surface of the passageway 5326, when the humidifier reservoir 5110 is fully inserted. For example, this sealing member 5152 may engage the passageway proximate a superior opening of the passageway 5326. Walls of the passageway 5326 may cause the sealing member 5152 to compress, thereby forming a pneumatic seal. Once the humidifier lid 5008 is connected to the humidifier reservoir base 5007 (e.g., either before or after the walls of the passageway 5326 engage the sealing member 5152), the reservoir cavity 5112 may be enclosed and/or pressurized within the overall volume of the humidifier 5000.

In some forms, the retention features 5330, 5338 may engage one another as described above in order to guide the humidifier reservoir 5110 into a proper orientation and to keep it there, once engaged. The retention force has to be sufficient to maintain the humidifier reservoir 5110 in place during operation. Some of the forces that the retaining force has to overcome can include; the repelling force created when the RPT device is turned on, the pressurised air is passed onto the humidifier reservoir 5110 and the operational pressure is applied to the humidifier reservoir 5110 (and in particular to the shroud 5318); the repelling force applied by any pogo pins, if any are used in the electrical contact between humidifier reservoir 5110 and the humidifier reservoir dock 5130 etc. However, if the engagement force between the retention features 5330, 5338 is sufficiently low, it may be relatively easy for a patient to disengage the retention features 5330 from the retention features 5338 and lift the humidifier reservoir 5110 in the superior direction with one hand. Thus, the retention forces between retention features 5330, 5338 (e.g. power of the magnets that can be used as such retention features) can provide a calibrated engagement force which, whilst still providing the necessary support for the humidifier reservoir 5110 in the engaged configuration, may also assist patients with conditions like arthritis, to easily remove the humidifier reservoir 5110 from the humidifier reservoir dock 5130 (e.g., in order to clean the different pieces). Similar calibrated retention features, whilst not strictly necessary and not indicated in the drawings, may also be used for retaining the RPT device 4000 into its device compartment 5132.

Both the RPT device and the humidifier reservoir 5110 are held essentially in a vertical orientation and are moved into superior-inferior direction during insertion into or removal from their respective compartment 5132, 5134. Once inserted, the humidifier reservoir 5110 may be held upright (e.g., oriented along the superior-inferior direction) by its engagement with compartment 5134 and with the third fluid conduit 5148. In other words, when the third fluid conduit 5148 is received within the passageway 5326, the humidifier reservoir 5110 is limited from pivoting toward the support surface (e.g., about a horizontal axis toward a table) because the third fluid conduit 5148 substantially fills the passageway 5326.

In some forms, the third fluid conduit 5148 may extend more superior than the superior opening to the passageway 5326 after being fully inserted into the passageway 5326. Additionally, the divider 5342 also extends more superior than the superior opening to the passageway 5326.

In certain forms, the divider 5342 may be adjacent to the shroud 5318. As shown in FIG. 5Q, the superior-most point of the divider 5342 is positioned adjacent to the shroud 5318 and the shroud 5318 has a positively domed shape relative to the divider 5342. In other forms, the divider 5342 may contact the shroud 5318.

In use, the RPT device 4000 may generate a flow of pressurized breathable gas, and may convey that gas to an entrance of the first fluid conduit 5140. The first fluid conduit 5140 may communicate with the humidification compartment 5134, and may convey the gas from the device compartment 5132 toward the humidification compartment 5134. The divider 5342 may block fluid from entering the second portion 5350, and instead may direct fluid into the inlet portion 5346 of the third fluid conduit 5148. The gas may travel in the superior direction through the inlet portion 5346, and may exit the third fluid conduit 5148 proximate to the shroud 5318. The divider 5342 may limit gas from immediately exiting the reservoir cavity 5112 (e.g., through the second portion 5350), and may instead direct the gas to contact the shroud 5318. The curvature of the shroud 5318 may direct the gas toward a bottom of the humidifier reservoir base 5007 (e.g., toward the heated liquid), where moisture may be added to the gas. A low pressure may exist at an entrance to the second portion 5350, and the now humidified gas may exit the reservoir cavity 5112 through the second portion 5350. The divider 5342 and the positive pressure in the inlet portion 5346 may prevent the humidified air in the second portion 5350 from returning to the reservoir cavity 5112 through the inlet portion 5346. The second portion may convey the humidified air to the second fluid conduit 5144, which may in turn convey the humidified air to the humidifier outlet 5004. A conduit of the air circuit 4170 and patient interface 3000 may be used to pass on the humidified gas to the patient.

In some forms, the humidifier outlet 5004 may be disposed on any of the side surfaces of the humidifier reservoir dock 5130. The flow of pressurized breathable gas may exit the humidifier outlet 5004 in a direction substantially perpendicular to the insertion axes for the RPT device 4000 and the humidifier reservoir 5110. Additionally, a decoupling structure, such as an elbow) may not be needed since the humidifier outlet 5004 is perpendicular to a structure (e.g., a table, night stand, etc.) supporting the humidifier 5000. Alternatively, the humidifier outlet 5004 may be disposed on a top surface of the humidifier reservoir dock 5130.

The shape, the size and the vertical orientation of both the RPT device 400 and the water reservoir 5110, have several positive effects on the patient's ability to handle the water reservoir 5110. Firstly, their transverse cross-sectional dimensions can be made more suitable for comfortable holding of the water reservoir 5110, if it does not require excessive stretch of the user's palm. At the same time, it is believed that handling of vertically oriented objects, such as handles or small boxes, is easier for a user as it requires less dexterity and wrist bending/twisting. This is believed to be especially applicable to older users whose wrist movements are often affected by arthritic pain. Furthermore, the fact that both the RPT device 4000 and the water reservoir 5110 are inserted into/extracted from the humidifier reservoir dock 5130 in a vertical direction, may reduce the overall friction of each of these components with the humidifier reservoir dock 5130. This, combined with the fact that during extraction, the gravitational force acts to retain the humidifier reservoir dock 5130 in place, may also contribute to convenient one-hand manipulation of the water reservoir 5110.

It is envisaged that the system may be such that only one of the RPT device 400 and the water reservoir 5110 may be arranged for vertical insertion and extraction. For example, in some arrangements only the water reservoir 5110 may be arranged for vertical insertion and extraction.

5.7 Aspects of the Invention

The present technology may also be described by the following list of aspects:

A1. A humidifier dock for humidifying a flow of pressurized breathable gas to be delivered to a patient, the humidifier dock comprising: a device compartment configured to at least partially removably receive an RPT device that is configured to supply the flow of pressurized breathable gas, and a humidification compartment fluidly connected to the device compartment; wherein the humidification compartment is configured to removably receive, at least partially, a humidification tub, the arrangement being such that at least one of the RPT device and the humidification tub is received within the dock in a vertical direction.

A2. The humidifier dock according to aspect A1, the dock further comprising the humidification tub, the humidification tub being configured to contain a supply of water and to be removably received, at least partially, in the humidification compartment so that, in operational configuration, the humidification tub is arranged to receive the flow of pressurized breathable gas and output the flow of pressurized breathable gas with increased humidity.

A3. The humidifier dock according to any one of aspects A1 to A2, wherein the humidification compartment includes a humidification compartment depth; the humidification tub includes a tub length; wherein in use, the humidification tub is configured to be engageable with the humidification compartment along a vertical insertion axis so that the humidification compartment depth and the tub length are measured parallel to the insertion axis, wherein the tub length is greater than the humidification compartment depth so that, when the humidification tub is fully engaged, an upper portion of the humidification tub extends above the humidification compartment to enable handling by the patient.

A4. The humidifier dock according to aspect A3, wherein the tub length is between approximately 25% to approximately 90% greater than the humidification compartment depth.

A5. The humidifier dock according to aspect A4, wherein the tub length is approximately 66% greater than the humidification compartment depth.

A6. The humidifier dock according to any one of aspects A1 to A5, wherein the humidification compartment includes a fluid passageway extending along the insertion axis.

A7. The humidifier dock according to aspect A6, wherein the humidification tub includes a passageway configured to at least partially receive the fluid passageway, in use.

A8. The humidifier dock according to any one of aspects A1 to A7, wherein the dock further includes a humidification compartment retention feature disposed within the humidification compartment; the humidification tub further includes a humidification reservoir retention feature located exterior to a cavity of the humidification tub, the humidification reservoir retention feature configured to removably engage with the humidification compartment retention feature.

A9. The humidification dock according aspect A8, wherein the humidification tub is configured to be guided into an engaged position by an interaction between the humidification compartment retention feature and the humidification reservoir retention feature.

A10. The humidifier dock according to any one of aspects A8 to A9, wherein the each of the humidification compartment retention feature and the humidification reservoir retention features include one or more magnets.

A11. The humidifier dock according to any one of aspects A1 to A10, further comprising a heater fixed to the humidification tub and configured to heat the supply of water.

A12. The humidifier dock according to aspect A11, wherein the heater is overmolded to the humidification tub.

A13. The humidifier dock according to any one of aspects A1 to A12, wherein the humidification tub includes a base and a lid configured to selectively engage the base, the lid being removable from the base when the humidification tub is positioned within the humidification compartment.

A14. A medical device comprising the humidifier dock according to any one of aspects A1 to A13; an RPT device having RPT device length and being configured to supply a flow of pressurized breathable gas, the RPT device being removably positionable within the device compartment; a patient interface configured to seal against patient's airways and deliver the flow of pressurized breathable gas with increased humidity to the patient's airways; and a conduit arranged to fluidly connect a humidifier outlet to the patient interface, so as to deliver the flow of pressurized breathable gas from the humidifier to the patient interface.

A15. The medical device according to aspect A14, when including the aspects of any one of aspects A3 to A13, wherein the device compartment is arranged to receive the RPT device in a direction parallel to the insertion axis so that a device compartment depth and the RPT device length are measured parallel to the insertion axis, the RPT device length being greater than the device compartment depth so that a portion of RPT device is exposed to enable handling by the user.

A16. The medical device according to any one of aspects A14 to A15 when including the aspects of any one of aspects A3 to A13, wherein the conduit is connected to the dock in a direction substantially perpendicular to the insertion axis.

B1. A system for humidifying a flow of pressurized breathable gas to be delivered to a patient to ameliorate a breathing disorder, the system comprising: a dock comprising: a device compartment including a device compartment bottom surface and a device compartment side wall, and, a humidification compartment fluidly connected to the device compartment, the humidification compartment including a humidification compartment bottom surface and a humidification compartment side wall; an RPT device configured to supply the flow of pressurized breathable gas, the RPT device being removably positionable within the device compartment of the dock, wherein when the RPT device is positioned within the device compartment the device compartment side wall extends partially along the RPT device; and a humidification tub configured to contain a supply of water and to be at least partially removably received in the humidification compartment so that, in an operational configuration, the humidification tub is arranged to receive the flow of pressurized breathable gas and output the flow of pressurized breathable gas with increased humidity, wherein when the humidification tub is positioned within the device compartment the device compartment side wall extends partially along the humidification tub; wherein the RPT device is at least partially exposed from the device compartment in an operating position; and wherein the humidification tub is at least partially exposed from the humidification compartment in an operating position.

B2. The system of aspect B1, wherein the humidification compartment is spaced apart from the device compartment so that the device compartment side wall is separate from the humidification compartment side wall.

B3. The system of any one of aspects B1 to B2, wherein the device compartment side wall is oriented perpendicularly with respect to the device compartment bottom surface.

B4. The system of any one of aspects B1 to B3, wherein the humidification compartment side wall is oriented perpendicularly with respect to the humidification compartment bottom surface.

B5. The system of any one of aspects B1 to B4, wherein the device compartment side wall is at least partially curved.

B6. The system of any one of aspects B1 to B5, wherein the humidification compartment side wall is at least partially curved.

B7. The system of any one of aspects B1 to B6, wherein the humidification tub is arranged to engage and disengage with the dock along a humidification tub insertion axis oriented substantially perpendicularly with respect to the humidification compartment bottom surface.

B8. The system of any one of aspects B1 to B7, wherein the RPT device is arranged to engage and disengage with the dock along a RPT device insertion axis oriented substantially perpendicularly with respect to the device compartment bottom surface.

B9. The system of any one of aspects B1 to B8, wherein the RPT device and the humidification tub are configured to be inserted into the dock along parallel axes.

B10. The system of any one of aspects B1 to B9, wherein: the humidification compartment further includes a humidification compartment retention feature; the humidification tub further includes a humidification reservoir retention feature configured to reversibly engage with the humidification compartment retention feature; and the humidification tub is configured to be guided into the operational configuration and/or held into the operational configuration, by proper engagement between the humidification compartment retention feature and the humidification reservoir retention feature.

B11. The system of aspect B10, wherein: humidification compartment retention feature includes a first magnet and a second magnet having an opposite polarity than the first magnet; humidification reservoir retention feature includes a first magnet and a second magnet having an opposite polarity than the first magnet; the humidification tub is configured to be guided into the operational configuration and/or held into the operational configuration by aligning the first magnet of the humidification compartment retention feature with the second magnet humidification reservoir retention feature, and by aligning the second magnet of the humidification compartment retention feature with the first magnet humidification reservoir retention feature.

B12. The system of any one of aspects B1 to B11, wherein the humidification compartment further includes a first conductive portion and the humidification tub includes a second conductive portion configured to contact the first conductive portion, wherein contact between the first conductive portion and the second conductive portion is configured to provide electrical energy to a heating element on the humidification tub.

B13. The system of any one of aspects B1 to B12, wherein a fluid conduit extends from the humidification compartment bottom surface, the humidification tub including a passageway configured to receive the fluid conduit when the humidification tub is received in the humidification compartment.

B14. The system of any one of aspects B1 to B13, wherein the fluid conduit includes a first passage and a second passage parallel to the first passage.

B15. The system of any one of aspects B1 to B14, the dock further includes an outlet configured to output the flow of pressurized breathable gas with increased humidity, the outlet perpendicular to the device compartment bottom surface and/or the humidification compartment bottom surface.

B16. The system of aspect B15, further comprising: a patient interface configured to seal against the patient's face and deliver the flow of pressurized breathable gas with increased humidity to the patient's airways; and a conduit arranged to fluidly connect the outlet to the patient interface, so as to deliver the flow of pressurized breathable gas from the humidifier to the patient interface.

C1. A humidifier for humidifying a flow of pressurized breathable gas to be delivered to a patient, the humidifier comprising: a dock comprising: a device compartment configured to at least partially removably receive an RPT device that is configured to supply the flow of pressurized breathable gas, a humidification compartment, an outlet, a first fluid conduit extending between the device compartment and the humidification compartment, the first fluid conduit configured to covey pressurized breathable gas from the device compartment to the humidification compartment, a second fluid conduit extending between the humidification compartment and the outlet, the second fluid conduit configured to covey pressurized breathable gas from the humidification compartment to the outlet, and a third fluid conduit in communication with the first fluid conduit and/or the second fluid conduit; a humidification tub configured to contain a supply of water and to be at least partially removably received in the humidification compartment so that, in an operational configuration, the humidification tub is arranged to receive the flow of pressurized breathable gas through the first fluid conduit and output the flow of pressurized breathable gas with increased humidity through the second fluid conduit to the outlet; wherein the humidification tub includes a passageway configured to receive the third fluid conduit in the operational configuration.

C2. The humidifier of aspect C1, wherein the third fluid conduit extends substantially perpendicularly out of the humidification compartment.

C3. The humidifier of any one of aspects C1 to C2, wherein the third fluid compartment includes a divider forming a first pathway and a second pathway, the first pathway configured to convey the flow of pressurized breathable gas from the first fluid conduit into the humidification tub and the second pathway configured to convey the flow of pressurized breathable gas with increased humidity to the second fluid conduit.

C4. The humidifier aspect C3, wherein the divider extends beyond an end of the third fluid conduit.

C5. The humidifier of any one of aspects C1 to C4, wherein the third fluid conduit extends superior to the passageway in the operational configuration.

C6. The humidifier of any one of aspects C1 to C5, wherein at least one of the passageway and the third fluid conduit includes a frustoconical shape.

C7. The humidifier of any one of aspects C1 to C6, wherein the outlet is oriented substantially perpendicularly with respect to the third conduit.

C8. The humidifier of any one of aspects C1 to C6, wherein the first fluid conduit extends substantially perpendicularly into the device compartment.

C9. The humidifier of any one of aspects C1 to C8, wherein the device compartment includes a first side wall and the humidification compartment includes a second side wall spaced apart from the first side wall.

C10. The humidifier of any one of aspects C1 to C9, wherein the third fluid conduit extends in a different direction than the first fluid conduit and/or the second fluid conduit.

C11. The humidifier of any one of aspects C1 to C10, wherein the first fluid conduit, the second fluid conduit, and the third fluid conduit are each spaced apart from one another.

C12. The humidifier of any one of aspects C1 to C11, wherein the third fluid conduit is configured to block fluid flow through the passageway.

C13. A medical device comprising: the humidifier of any one of aspects C1 to C12; an RPT device configured to supply a flow of pressurized breathable gas, the RPT device being removably positionable within the device compartment of the humidifier; and a patient interface configured to seal against the patient's face and deliver the flow of pressurized breathable gas with increased humidity to the patient's airways; and a conduit arranged to fluidly connect the outlet to the patient interface, so as to deliver the flow of pressurized breathable gas from the humidifier to the patient interface.

C14. The medical device of aspect C13, wherein: when fully inserted into the device compartment, at least a portion of the RPT device is exposed and configured to be grasped by the patient; and when fully inserted into the humidification compartment, at least a portion of the humidification tub is exposed and configured to be grasped by the patient.

5.8 Glossary

For the purposes of the present technology disclosure, in certain forms of the present technology, one or more of the following definitions may apply. In other forms of the present technology, alternative definitions may apply.

5.8.1 General

Air: In certain forms of the present technology, air may be taken to mean atmospheric air, and in other forms of the present technology air may be taken to mean some other combination of breathable gases, e.g. oxygen enriched air.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Device flow rate, $Q_d$, is the flow rate of air leaving the RPT device. Total flow rate, $Q_t$, is the flow rate of air and any supplementary gas reaching the patient interface via the air circuit. Vent flow rate, $Q_v$, is the flow rate of air leaving a vent to allow washout of exhaled gases. Leak flow rate, $Q_l$, is the flow rate of leak from a patient interface system or elsewhere. Respiratory flow rate, $Q_r$, is the flow rate of air that is received into the patient's respiratory system.

Flow therapy: Respiratory therapy comprising the delivery of a flow of air to an entrance to the airways at a controlled flow rate referred to as the treatment flow rate that is typically positive throughout the patient's breathing cycle.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Oxygen enriched air: Air with a concentration of oxygen greater than that of atmospheric air (21%), for example at least about 50% oxygen, at least about 60% oxygen, at least about 70% oxygen, at least about 80% oxygen, at least about 90% oxygen, at least about 95% oxygen, at least about 98% oxygen, or at least about 99% oxygen. "Oxygen enriched air" is sometimes shortened to "oxygen".

Medical Oxygen: Medical oxygen is defined as oxygen enriched air with an oxygen concentration of 80% or greater.

Patient: A person, whether or not they are suffering from a respiratory condition.

Pressure: Force per unit area. Pressure may be expressed in a range of units, including $cmH_2O$, $g$–$f/cm^2$ and hectopascal. 1 $cmH_2O$ is equal to 1 $g$–$f/cm^2$ and is approximately 0.98 hectopascal (1 hectopascal=100 Pa=100 $N/m^2$=1 millibar 0.001 atm). In this specification, unless otherwise stated, pressure is given in units of $cmH_2O$.

The pressure in the patient interface is given the symbol Pm, while the treatment pressure, which represents a target value to be achieved by the interface pressure Pm at the current instant of time, is given the symbol Pt.

Respiratory Pressure Therapy: The application of a supply of air to an entrance to the airways at a treatment pressure that is typically positive with respect to atmosphere.

Ventilator: A mechanical device that provides pressure support to a patient to perform some or all of the work of breathing.

5.8.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

Positive curvature: If the curve at p turns towards the outward normal, the curvature at that point will be taken to be positive (if the imaginary small person leaves the point p they must walk uphill). See FIG. 3B (relatively large positive curvature compared to FIG. 3C) and FIG. 3C (relatively small positive curvature compared to FIG. 3B). Such curves are often referred to as concave.

Zero curvature: If the curve at p is a straight line, the curvature will be taken to be zero (if the imaginary small person leaves the point p, they can walk on a level, neither up nor down). See FIG. 3D.

Negative curvature: If the curve at p turns away from the outward normal, the curvature in that direction at that point will be taken to be negative (if the imaginary small person leaves the point p they must walk downhill). See FIG. 3E (relatively small negative curvature compared to FIG. 3F) and FIG. 3F (relatively large negative curvature compared to FIG. 3E). Such curves are often referred to as convex.

5.8.1.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small. The plane curves in FIGS. 3B to 3F could be examples of such multiple cross-sections at a particular point.

Principal curvatures and directions: The directions of the normal planes where the curvature of the curve takes its maximum and minimum values are called the principal directions. In the examples of FIG. 3B to FIG. 3F, the maximum curvature occurs in FIG. 3B, and the minimum occurs in FIG. 3F, hence FIG. 3B and FIG. 3F are cross sections in the principal directions. The principal curvatures at p are the curvatures in the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical—topological sense, e.g. a continuous space curve from f(0) to f(1) on a surface. In certain forms of the present technology, a 'path' may be described as a route or course, including e.g.

a set of points on a surface. (The path for the imaginary person is where they walk on the surface, and is analogous to a garden path).

Path length: In certain forms of the present technology, 'path length' will be taken to mean the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

5.9 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Furthermore, "approximately", "substantially", "about", or any similar term as used herein means+/−5 to +/−10% of the recited value.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

5.10 Reference Signs List

| | |
|---|---|
| patient | 1000 |
| bed partner | 1100 |
| patient interface | 3000 |
| non-invasive patient interface | 3000 |
| seal-forming structure | 3100 |
| plenum chamber | 3200 |
| chord | 3210 |
| superior point | 3220 |
| inferior point | 3230 |
| positioning and stabilizing structure | 3300 |
| vent | 3400 |
| connection port | 3600 |
| forehead support | 3700 |
| ISO | 3744 |
| RPT device | 4000 |
| external housing | 4010 |
| upper portion | 4012 |
| portion | 4014 |

| | |
|---|---|
| panel | 4015 |
| chassis | 4016 |
| handle | 4018 |
| pneumatic block | 4020 |
| air filter | 4110 |
| inlet air filter | 4112 |
| outlet air filter | 4114 |
| muffler | 4120 |
| inlet muffler | 4122 |
| outlet muffler | 4124 |
| pressure generator | 4140 |
| blower | 4142 |
| motor | 4144 |
| anti-spill back valve | 4160 |
| air circuit | 4170 |
| heated air circuit | 4171 |
| supplementary gas | 4180 |
| electrical components | 4200 |
| single Printed Circuit Board Assembly | 4202 |
| power supply | 4210 |
| input device | 4220 |
| transducer | 4270 |
| humidifier | 5000 |
| humidifier inlet | 5002 |
| humidifier outlet | 5004 |
| humidifier base | 5006 |
| humidifier reservoir base | 5007 |
| humidifier lid | 5008 |
| outer surface | 5009 |
| inner surface | 5010 |
| bottom surface | 5014 |
| reservoir | 5110 |
| reservoir cavity | 5112 |
| inner bottom surface | 5114 |
| reservoir axis | 5116 |
| conductive portion | 5120 |
| humidifier reservoir dock | 5130 |
| device compartment | 5132 |
| humidification compartment | 5134 |
| locking lever | 5135 |
| central wall | 5136 |
| RPT insertion axis | 5137 |
| reservoir insertion axis | 5138 |
| first fluid conduit | 5140 |
| connector | 5142 |
| second fluid conduit | 5144 |
| surface | 5146 |
| third fluid conduit | 5148 |
| water level indicator | 5150 |
| sealing member | 5152 |
| humidifier transducer | 5210 |
| pressure transducers | 5212 |
| flow rate transducers | 5214 |
| temperature transducers | 5216 |
| humidity sensor | 5218 |
| heating element | 5240 |
| humidifier controller | 5250 |
| central humidifier controller | 5251 |
| heating element controller | 5252 |
| air circuit controller | 5254 |
| surface | 5300 |
| projections | 5302 |
| complimentary projections | 5304 |
| cap | 5308 |
| water inlet opening | 5310 |
| portion | 5312 |
| body | 5314 |
| user engagement portion | 5316 |
| shroud | 5318 |
| upper portion | 5320 |
| outlet | 5322 |
| column | 5324 |
| passageway | 5326 |
| humidification reservoir retention feature | 5330 |
| electrically conductive portion | 5334 |
| electrically conductive portion | 5336 |
| humidification compartment retention feature | 5338 |
| divider | 5342 |
| inlet portion | 5346 |
| outlet portion | 5350 |

What is claimed is:

1. A humidifier for humidifying a flow of pressurized breathable gas to be delivered to a patient, the humidifier comprising:
a dock comprising:
a device compartment configured to at least partially removably receive an RPT device that is configured to supply the flow of pressurized breathable gas, and
a humidification compartment fluidly connected to the device compartment,
the dock being structured to convey the flow of pressurized breathable gas through the dock from the device compartment to the humidification compartment; and
a humidification tub configured to contain a supply of water and to be at least partially removably received in the humidification compartment so that, in an operational configuration, the humidification tub is arranged to receive the flow of pressurized breathable gas and output the flow of pressurized breathable gas with increased humidity,
an electrical heater fixed to the humidification tub when in the operational configuration and when not in the operational configuration, and, wherein the electrical heater is configured to heat the supply of water.

2. The humidifier of claim 1, wherein the humidification tub is arranged to engage and disengage with the dock along a humidification tub insertion axis in a substantially vertical direction.

3. The humidifier of claim 1, wherein the device compartment is configured to receive only a portion of an engaged RPT device, so that the RPT device is at least partially exposed when completely positioned in the device compartment in the operational configuration.

4. The humidifier of claim 1, wherein the humidification tub comprises;
a tub base arranged to be, at least partially, removably received in the humidification compartment, the tub base including a cavity configured to contain the supply of water; and
a tub lid removably coupled to the tub base;
wherein the heater is attached to the tub base.

5. The humidifier of claim 4, wherein the heater is overmolded to an inner side of the tub base.

6. The humidifier of claim 4, wherein the tub base includes an electrical connector that is configured to electrically connect with an electrical connector disposed within the humidification compartment.

7. The humidifier of claim 4, wherein the tub lid is removably coupled to the tub base and configured for single handed operation.

8. The humidifier of claim 4, wherein the tub lid further comprises a water inlet opening that allows filling of the tub base with water, and a cap removably coupled to the tub lid in order to selectively cover the water inlet opening.

9. The humidifier of claim 8, wherein the humidification tub is only partly received within the humidification compartment so that the humidification tub extends beyond a space defined by the humidification compartment, at least the tub lid being exposed to ambient and uncovered by the dock in use, and wherein the cap is removable while the tub base is at least partially positioned within the humidification compartment.

10. The humidifier of claim 4, wherein the tub lid includes a shroud configured to be received within the cavity when the tub lid is coupled to the tub base.

11. The humidifier of claim 10, wherein the tub lid further comprises a water inlet opening that allows filling of the tub base with water, and the shroud is spaced apart from the water inlet opening, and is oriented with a negatively domed shape with respect to the water inlet opening.

12. The humidifier of claim 4, wherein the tub base includes a tub base opening configured to allow the flow of pressurized breathable gas into and/or out of the cavity.

13. The humidifier of claim 4, wherein:
the dock further includes a humidification compartment retention feature disposed within the humidification compartment;
the humidification tub further includes a humidification reservoir retention feature located at the tub base exterior to the cavity and configured to reversibly engage with the humidification compartment retention feature; and
the humidification tub is configured to be guided into the operational configuration and/or held into the operational configuration, by proper engagement between the humidification compartment retention feature and the humidification reservoir retention feature.

14. The humidifier of claim 13, wherein each of the humidification compartment retention feature and the humidification reservoir retention feature includes one or more magnets, the humidification compartment retention feature and the humidification reservoir retention feature being arranged such that electromagnetic forces between magnets of respective polarity permit only an engagement in the operational configuration.

15. The humidifier of claim 14, wherein the humidification tub is configured to engage with the humidification compartment with a magnetic connection and at least one additional connection selected from the group consisting of a mechanical connection, an electrical, and a pneumatic, wherein the magnetic connection and the additional connection are configured to be effected simultaneously.

16. The humidifier of claim 1, wherein the dock further comprises a passage configured to convey the flow of pressurized breathable gas through the dock from the device compartment to the humidification compartment.

17. The humidifier of claim 16, wherein the passage includes a first fluid conduit extending between the device compartment and the humidification compartment, the first fluid conduit configured to convey the flow of pressurized breathable gas through the dock from the device compartment to the humidification compartment; and
the dock further comprises:
an outlet configured to convey the flow of pressurized breathable gas to the patient, the outlet being spaced apart from the device compartment and from the humidification compartment; the outlet having a tubular shape and defining an axis that is oriented in a direction substantially perpendicular to a direction of a humidification tub insertion axis, and
a second fluid conduit extending between the humidification compartment and the outlet, the second fluid conduit configured to convey the flow of pressurized breathable gas from the humidification compartment to the outlet.

18. The humidifier of claim 17, wherein the humidification compartment includes a third fluid conduit in communication with the first fluid conduit and/or the second fluid conduit.

19. The humidifier of claim 18, wherein the humidification tub comprises a tub base including a passageway configured to receive the third fluid conduit in the operational configuration so that the passageway and the third fluid conduit are coaxial.

20. The humidifier of claim 19, wherein the third fluid conduit extends superior to the passageway in the operational configuration.

21. The humidifier of claim 20, wherein a shroud is positioned adjacent an opening of the third fluid conduit when a tub lid is coupled to the tub base in the operational configuration.

22. The humidifier of claim 19, wherein at least one of the passageway and the third fluid conduit includes a frusto-conical shape.

23. The humidifier of claim 19, wherein the tub base includes a tub base opening configured to allow the flow of pressurized breathable gas into and/or out of a cavity of the humidification tub; and an outer surface adjacent an opening of the third fluid conduit includes a sealing member that is configured to engage an inner surface of the passageway of the tub base opening, the sealing member configured to prevent the flow of pressurized breathable gas between the passageway and the third fluid conduit.

24. The humidifier of claim 23, wherein the sealing member is a silicone lip seal or an O-ring.

25. The humidifier of claim 18, wherein the outlet is oriented in a direction substantially perpendicular to the direction of the third fluid conduit.

26. The humidifier of claim 25, wherein the third fluid conduit includes a divider that separates the third fluid conduit into an inlet portion and an outlet portion, the divider configured to at least partially isolate the inlet portion from the outlet portion, the humidification tub includes a tub base and a tub lid with a shroud configured to be positioned adjacent an opening of the third fluid conduit when the tub lid is coupled to the tub base in the operational configuration, and the shroud and the third fluid conduit are configured so that the shroud prevents water from entering the inlet portion and the outlet portion when water is poured into the humidification tub when the humidification tub is in the operational configuration inside the humidification compartment.

27. The humidifier of claim 26, wherein the flow of pressurized breathable gas is configured to enter a cavity of the humidification tub through the inlet portion and the flow of pressurized breathable gas is configured to exit the cavity through the outlet portion.

28. The humidifier of claim 27, wherein the tub base includes a tub base opening with a passageway, and the divider is configured to extend superior to the passageway of the tub base opening.

29. A medical device comprising:
the humidifier of claim 1, the humidifier including an outlet configured to convey the flow of pressurized breathable gas to the patient; and
an RPT device configured to supply a flow of pressurized breathable gas, the RPT device being removably positionable within the device compartment of the humidifier.

30. The medical device of claim 29, wherein:
when fully inserted into the device compartment, at least a portion of the RPT device is exposed and configured to be grasped by the patient; and
when fully inserted into the humidification compartment, at least a portion of the humidification tub is exposed and configured to be grasped by the patient.

31. The medical device of claim 29, further comprising:
a patient interface configured to seal against the patient's face and deliver the flow of pressurized breathable gas with increased humidity to the patient's airways; and
a conduit arranged to fluidly connect the outlet to the patient interface, so as to deliver the flow of pressurized breathable gas from the humidifier to the patient interface.

32. A system for humidifying a flow of pressurized breathable gas to be delivered to a patient to ameliorate a breathing disorder, the system comprising:
a dock comprising:
a device compartment including a device compartment bottom surface and a device compartment side wall, and
a humidification compartment fluidly connected to the device compartment, the humidification compartment including a humidification compartment bottom surface and a humidification compartment side wall,
wherein the dock is structured to convey the flow of pressurized breathable gas through the dock from the device compartment to the humidification compartment;
an RPT device configured to supply the flow of pressurized breathable gas, the RPT device being removably positionable within the device compartment of the dock in an upright position with an outlet of the RPT device facing downwards and towards the humidification compartment bottom surface; wherein, when the RPT device is positioned within the device compartment, the device compartment side wall extends partially along the RPT device; and
a humidification tub configured to contain a supply of water and to be at least partially removably received in the humidification compartment so that, in an operational configuration, the humidification tub is arranged to receive the flow of pressurized breathable gas and output the flow of pressurized breathable gas with increased humidity; wherein, when the humidification tub is positioned within the humidification compartment, the humidification compartment side wall extends partially along the humidification tub;
wherein the RPT device is at least partially exposed from the device compartment in an operating position; and
wherein the humidification tub is at least partially exposed from the humidification compartment in an operating position.

33. A humidifier for humidifying a flow of pressurized breathable gas to be delivered to a patient, the humidifier comprising:
a dock comprising:
a device compartment configured to at least partially removably receive an RPT device that is configured to supply the flow of pressurized breathable gas,
a humidification compartment,
an outlet,
a first fluid conduit extending from an opening of the device compartment to the humidification compartment, the first fluid conduit configured to convey pressurized breathable gas from the device compartment to the humidification compartment,
a second fluid conduit extending between the humidification compartment and the outlet, the second fluid conduit configured to convey pressurized breathable gas from the humidification compartment to the outlet, and
a third fluid conduit in communication with the first fluid conduit and/or the second fluid conduit, the third fluid conduit being fixed to and extending from a bottom surface of the humidification compartment;
a humidification tub configured to contain a supply of water and to be at least partially removably received in the humidification compartment so that, in an operational configuration, the humidification tub is arranged to receive the flow of pressurized breathable gas through the first fluid conduit and output the flow of pressurized breathable gas with increased humidity through the second fluid conduit to the outlet;
wherein the humidification tub includes a passageway configured to receive the third fluid conduit in the operational configuration, and only after the humidifier tub has been inserted into the humidification compartment, and
wherein the third fluid conduit is configured to convey the pressurized gas before humidity is added from the first fluid conduit to an interior of the humidification tub, and to convey the pressurized gas with added humidity from the interior of the humidification tub to the second fluid conduit.

* * * * *